United States Patent
Hamm

(10) Patent No.: US 12,285,410 B2
(45) Date of Patent: Apr. 29, 2025

(54) COMBINATION COMPRISING HDAC INHIBITOR AND CD137 AGONIST FOR CANCER THERAPY

(71) Applicant: 4SC AG, Planegg-Martinsried (DE)

(72) Inventor: Svetlana Hamm, Eichenau (DE)

(73) Assignee: 4SC AG, Planegg-Martinsried (DE)

( * ) Notice: Subject to any disclaimer, the term of this patent is extended or adjusted under 35 U.S.C. 154(b) by 1190 days.

(21) Appl. No.: 17/041,703

(22) PCT Filed: Mar. 26, 2019

(86) PCT No.: PCT/EP2019/057528
§ 371 (c)(1),
(2) Date: Sep. 25, 2020

(87) PCT Pub. No.: WO2019/185598
PCT Pub. Date: Oct. 3, 2019

(65) Prior Publication Data
US 2021/0113528 A1    Apr. 22, 2021

(30) Foreign Application Priority Data

Mar. 26, 2018   (EP) .................................. 18163896

(51) Int. Cl.
*A61K 31/4155*   (2006.01)
*A61K 35/17*   (2015.01)
*A61K 35/18*   (2015.01)
*A61K 35/761*   (2015.01)
*A61K 39/395*   (2006.01)
*A61P 35/00*   (2006.01)

(52) U.S. Cl.
CPC .......... *A61K 31/4155* (2013.01); *A61K 35/17* (2013.01); *A61K 35/18* (2013.01); *A61K 35/761* (2013.01); *A61K 39/3955* (2013.01); *A61P 35/00* (2018.01)

(58) Field of Classification Search
None
See application file for complete search history.

(56) References Cited

FOREIGN PATENT DOCUMENTS

WO   2006/097474 A1   9/2006

OTHER PUBLICATIONS

International Search Report dated Jun. 27, 2019 issued in corresponding PCT/EP2019/057528 application (4 pages).
F. Hermann et al., "4SC-202 Plus Anti-PD1: Breaking PD1-Refractoriness to Increase Efficacy of Checkpoint Inhibition in Patients with Advanced Melanoma", Journal of Translational Medicine, vol. 16, No. Supplement 1 (2018) pp. 13-14.
A. Yonezawa et al., "Boosting Cancer Immunotherapy with Anti-CD137 Antibody Therapy", Clin. Caner Res., vol. 21, No. 14 (2015) pp. 3113-3120.

*Primary Examiner* — Samantha L Shterengarts
(74) *Attorney, Agent, or Firm* — Millen, White, Zelano & Branigan, P.C.; Csaba Henter

(57) ABSTRACT

The invention relates to medical uses of an HDAC inhibitor of the below general formula I, wherein R1 to R7 are as described herein, or a salt or solvate thereof in combination with a CD137 agonist for the treatment of cancer.

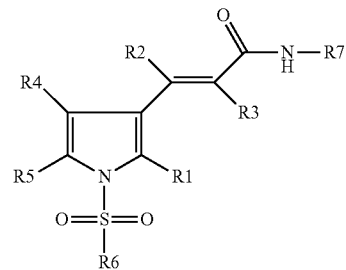

15 Claims, 1 Drawing Sheet

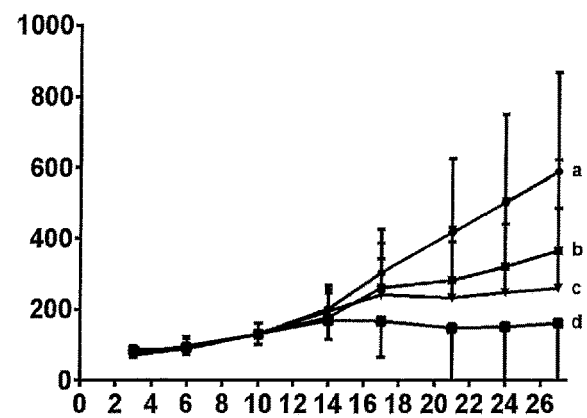
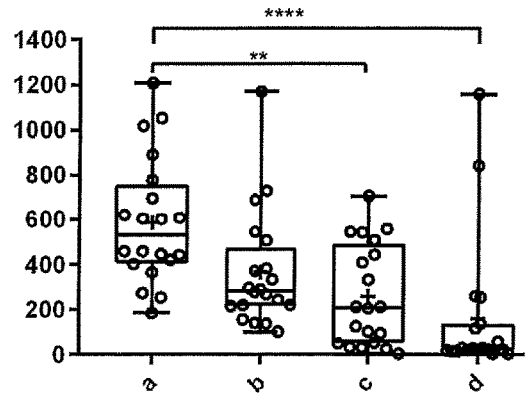
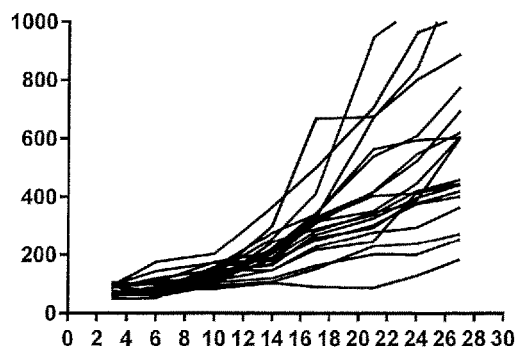
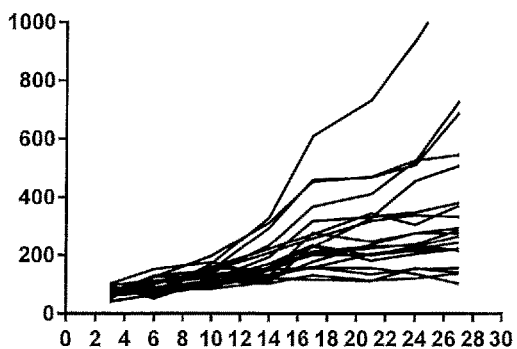
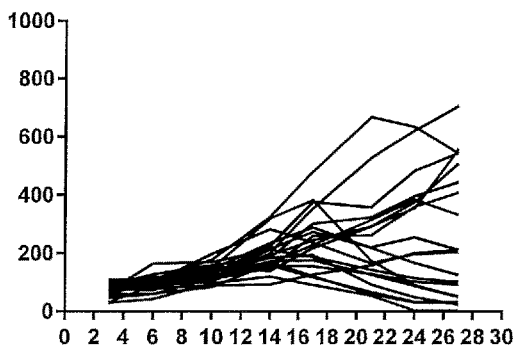
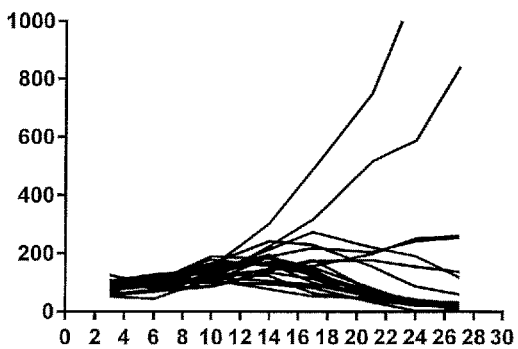

COMBINATION COMPRISING HDAC INHIBITOR AND CD137 AGONIST FOR CANCER THERAPY

FIELD OF APPLICATION OF THE INVENTION

The invention relates to medical applications of an HDAC inhibitor in combination with a CD137 agonist in the treatment of cancer.

KNOWN TECHNICAL BACKGROUND

CD137 is an inducible costimulatory receptor expressed on activated T and natural killer (NK) cells from the family of tumor necrosis factor receptors, and is also known as "tumor necrosis factor receptor superfamily member 9" (TNFRSF9), 4-1BB and "induced by lymphocyte activation" (ILA). CD137 ligation on T cells triggers a signaling cascade that results in upregulation of antiapoptotic molecules, cytokine secretion, and enhanced effector function. In dysfunctional T cells that have a decreased cytotoxic capacity, 4-1BB ligation demonstrates a potent ability to restore effector functions (Chester et al, 2018, Blood, 131, 49-57).

Histone deacetylases (HDACs) are enzymes that catalyze the removal of acetyl groups from specific histone sites in particular at promotor and enhancer regions, which is an essential part of regulation of cellular gene transcription. HDACs also regulate gene expression in an indirect fashion by mediating the acetylation of non-histone proteins such as DNA-binding proteins, transcription factors, signal transducers, DNA repair and chaperon proteins (Ververis K et al., Biologics: Targets and Therapy 7: 47-60, 2013; Vitt D et al., Targeting histone acetylation. In: RSC Drug Discovery Series No. 48: Epigenetics for Drug Discovery. Editor: Nessa Carey. The Royal Society of Chemistry, 2016).

HDAC inhibitors have been described to cause growth arrest with subsequent differentiation or apoptosis of tumor cells, whereas normal cells are not affected. As summarized in a review article by Marks et al. (Nature Reviews Cancer, 2001, Volume 1, page 194-202), HDAC inhibitors cause cell-cycle arrest in G1 and/or G2 phase. Growth-inhibitory effects have been documented in vitro in virtually all transformed cell types, including cell lines that arise from both hematological and epithelial tumors. The growth inhibitory cellular mechanism of the HDAC inhibitors has been described as a specific induction of expression of the cell cycle inhibitor CDKN1A (p21). Additionally, this review article summarizes the induction of growth arrest in tumor-bearing mice by HDAC inhibitors. Efficacy of HDAC inhibitors has been demonstrated in animal models of diverse cancer types such as breast, prostate, lung and stomach cancers, neuroblastoma and leukemia.

Treatments of many cancer types by HDAC inhibitors have been described in the available literature. HDAC inhibition has an effect on the expression of a number of proteins playing pivotal roles in tumor-relevant processes, such as HER2/neu, VEGF, raf-1, cyclin A and B, Bax, Bad, p53, c-myc, Caspase 3, p21 and ERα. According to a review by Villar-Garea et al. (Int. J. Cancer: 112, 171-178 (2004)) cancer is understood to be an epigenetic as well as a genetic disease and the main goal using HDAC inhibitors would be restoration of gene expression of those tumor-suppressor genes that have been transcriptionally silenced by promotor-associated histone deacetylation. Drummond et al. (Annu. Rev. Pharmacol. Toxicol. 2005. 45:495-528) review the molecular mechanism and outcome of histone and non-histone substrates in cancer cells, which are effectors of HDAC, while HDAC also facilitates the acetylation of several key proteins other than histones. According to said review, acetylation is a key posttranslational modification of many proteins responsible for regulating critical intracellular pathways, and many of these substrates are tissue/development specific (EKLF, GATA-1, ERα, MyoD), oncogenic (c-Myb), tumor-suppressing (p53), or even rather ubiquitous (TFIIE, TFIIF, TCF, HNF-4) transcription factors. Modulation of those proteins can lead to induction of cell cycle arrest, differentiation and apoptosis, all of which are desirable mechanisms for treatment of cancer. Kelly et al. (Expert Opin Invest Drugs, 11(12), 2002) provides a further review on HDAC inhibitors in general and their application in cancer therapy.

The official US NIH website http://clinicaltrials.gov lists (status: February 2016) 545 clinical trials for cancer indications treated with HDAC inhibitors, among others various forms of leukemia (e.g. CML, CLL, AML), myelodysplastic syndrome, lymphoma including non-hodgkin's lymphoma, multiple myeloma, plasma cell neoplasm, solid tumors in general, small intestine cancer, mesothelioma, prostate, breast (male and female), lung cancer (including non-small and small cell), neuroendocrine, malignant epithelial neoplasms, pancreas, skin cancer (including melanoma), multiple myeloma, cervix, renal cell, head and neck, gastric, ovarian, liver cancer, colon, rectal, thymoma, fallopian tube, peritoneal, nasopharyngeal, vestibular schwannoma, meningioma, acoustic neuroma, neurofibromatosis type 2, thyroid, urothelial, gliomas, brain, esophagus, astrocytoma, anaplastic oligodendroglioma, giant cell glioblastoma, glioblastoma, gliosarcoma, mixed glioma and brain neoplasm.

4SC-202 (E)-N-(2-aminophenyl)-3-(1-((4-(1-methyl-1H-pyrazol-4-yl)phenyl)sulfonyl)-1H-pyrrol-3-yl)acrylamide is an orally available HDAC inhibitor histone-deacetylase (HDAC) inhibitor.

4SC-202 has been evaluated in a Phase I clinical trial (TOPAS) in 24 heavily pre-treated patients with different types of blood cancer. 4SC-202 was well tolerated with few and/or manageable adverse events. Positive signs of anti-tumor efficacy were observed with one complete remission for 28 months and one partial responder for 8 months. Findings also exhibited disease control in 83% of the patients and long-term stabilization in 50% of patients.

WO 2006/097474 A1 describes certain N-sulphonylpyrrole derivatives and their medical utility.

WO 2009/112522 A1 describes salts of certain N-sulphonylpyrrole derivatives and their medical utility.

BRIEF DESCRIPTION OF THE FIGURES

FIG. 1: Anti-tumoral effect of 4SC-202, or an agonistic anti-CD137 antibody in comparison with the combination of 4SC-202 and the antibody in an immunocompetent syngeneic murine C38 model. In all cases, the x-axis represents time (days), the y-axis represents tumor volume in mm3; a) vehicle, b) 4SC-202, c) CD137 antibody and d) combination of 4SC-202 and CD137 antibody. Dunnett's multiple comparison test was used to analyze the difference between treatment and vehicle group. A) panel a shows the mean of all animals in each group, while panel b shows the box plot for day 27 data of C38 model (tumor volume ($mm^3$) on the y-axis, median and 25/75 percentiles are shown, whiskers indicate min to max, + indicates the mean value. B) Individual curves of animals in each group a-d.

DESCRIPTION OF THE INVENTION

It has now been found unexpectedly that the combination therapy utilizing an HDAC inhibitor of the present invention with a CD137 agonist shows beneficial efficacy compared with monotherapy.

Certain embodiments of the present invention are listed in the following items:
1. Use of an HDAC inhibitor of the below general formula I or a salt or solvate thereof for the manufacture of a medicament for the treatment of cancer in combination with a CD137 agonist,
formula I

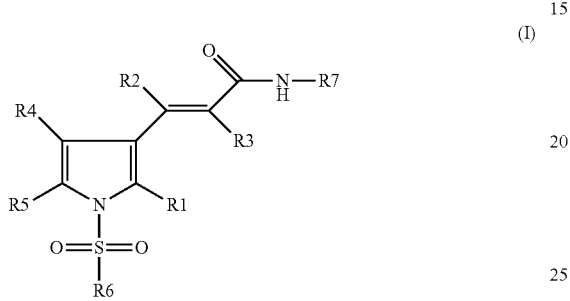

in which
R1, R4 and R5 are independently hydrogen, 1-4C-alkyl, halogen, or 1-4C-alkoxy,
R2 and R3 are independently hydrogen or 1-4C-alkyl,
R6 is -T1-Q1, in which T1 is a bond or 1-4C-alkylene,
either Q1 is substituted by R61 and/or R62, and is Aa1, Hh1, Ha1, Ha2, Ha3, Ha4 or Ah1, or Q1 is unsubstituted, and is Ha2, Ha3 or Ha4,
in which
R61 is 1-4C-alkyl, phenyl-1-4C-alkyl, 1-4C-alkoxy, hydroxyl, trifluoromethyl, cyano, halogen, completely fluorine-substituted 1-4C-alkoxy or 1-4C-alkoxy wherein more than half of the hydrogen atoms are replaced by fluorine atoms, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, —U-T3-N(R613)R614, -T4-Het3, or —V-T5-Het4, in which
T2 is a bond or 1-4C-alkylene,
R611 is hydrogen, 1-4C-alkyl, 3-7C-cycloalkyl, 3-7C-cycloalkylmethyl, hydroxy-2-4C-alkyl, 1-4C-alkoxy-2-4C-alkyl, 1-4C-alkylcarbonyl, or 1-4C-alkylsulphonyl,
R612 is hydrogen or 1-4C-alkyl,
or R611 and R612 together and with inclusion of the nitrogen atom, to which they are bonded, form a heterocyclic ring Het1, in which Het1 is morpholino, thiomorpholino, S-oxo-thiomorpholino, S,S-dioxo-thiomorpholino, piperidino, pyrrolidino, piperazino, or 4N-(1-4C-alkyl)-piperazino,
U is —O— (oxygen) or —C(O)NH—,
T3 is 2-4C-alkylene,
R613 is hydrogen, 1-4C-alkyl, 3-7C-cycloalkyl, 3-7C-cycloalkylmethyl, hydroxy-2-4C-alkyl or 1-4C-alkoxy-2-4C-alkyl, 1-4C-alkylcarbonyl, or 1-4C-alkylsulphonyl
R614 is hydrogen or 1-4C-alkyl,
or R613 and R614 together and with inclusion of the nitrogen atom, to which they are bonded, form a heterocyclic ring Het2, in which
Het2 is morpholino, thiomorpholino, S-oxo-thiomorpholino, S,S-dioxo-thiomorpholino, piperidino, pyrrolidino, piperazino, or 4N-(1-4C-alkyl)-piperazino,
T4 is a bond or 1-4C-alkylene,
Het3 is 1N-(1-4C-alkyl)-piperidinyl or 1N-(1-4C-alkyl)-pyrrolidinyl,
V is —O— (oxygen) or —C(O)NH—,
T5 is a bond or 1-4C-alkylene,
Het4 is 1N-(1-4C-alkyl)-piperidinyl or 1N-(1-4C-alkyl)-pyrrolidinyl,
R62 is 1-4C-alkyl, 1-4C-alkoxy or halogen,
Aa1 is a bisaryl radical made up of two aryl groups,
which are selected independently from a group consisting of phenyl and naphthyl, and
which are linked together via a single bond,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond,
Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group,
Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group,
Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group,
Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, Ha4 is a heteroarylaryl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha4 is bonded via said aryl moiety to the to the parent molecular group, R7 is hydroxyl, or Cyc1, in which Cyc1 is a ring system of formula Ia

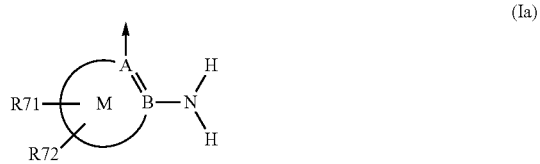

in which

A and B are C (carbon),

R71 and R72 are independently hydrogen, halogen, 1-4C-alkyl, or 1-4C-alkoxy,

M with inclusion of A and B is either a ring Ar2 or a ring Har2, in which Ar2 is a benzene ring, Har2 is a monocyclic 5- or 6-membered unsaturated heteroaromatic ring comprising one to three heteroatoms, each of which is selected from the group consisting of nitrogen, oxygen and sulfur.

2. The use according to item 1, wherein the HDAC inhibitor is (E)-N-(2-aminophenyl)-3-(1-((4-(1-methyl-1H-pyrazol-4-yl)phenyl)sulfonyl)-1H-pyrrol-3-yl)acrylamide (also known as 4SC-202), or a salt or solvate thereof.

3. The use according to item 1, wherein the HDAC inhibitor is 4SC-202 tosylate salt.

4. The use according to any one of items 1 to 3, wherein the CD137 agonist is selected from the group consisting of INBRX-105 (Elpiscience Biopharmaceuticals Inc; INHIBRx LLC), ADG-106 (Adagene Suzhou Ltd), FS-120 (F-star Biotechnologische Forschungs-und Entwicklungs GmbH), CB-307 (Crescendo Biologics Ltd), STIM-41BBL (Merrimack Pharmaceuticals Inc), FS-222 (F-star Biotechnologische Forschungs-und Entwicklungs GmbH), PRS-344 (Pieris Pharmaceuticals Inc; Servier), GEN-1046 (BioNTech SE; Genmab Holding BV), AGEN-2373 (Agenus Inc), CD19-4-1BBL (Roche Innovation Center Copenhagen A/S), AM-105 (AbClon Inc), CTX-471 (Compass Therapeutics LLC), TM-123+UniCAR-T (Cellex GmbH; GEMoaB Monoclonals GmbH), RTX-240 (Rubius Therapeutics Inc), CUE-201 (Cue Biopharma Inc), RTX-224 (Rubius Therapeutics Inc), Utomilumab (PF-05082566), Urelumab (BMS-663513), ABP-300 (Abpro), EU-101 (Eutilex Co Ltd), ATOR-1016 (Alligator Bioscience AB), PRS-343, PRS-342 (Pieris Pharmaceuticals Inc), ET-140 or lisocabtagene maraleucel (Juno Therapeutics Inc), LOAd-703 (Lokon Pharma AB), KAHR-105 KAHR-107 (KAHR medical Ltd), SCB-333 (Clover Biopharmaceuticals), MP-0310 (Molecular Partners AG), ISAS-01 (FasCure Therapeutics LLC), and Ultra-41BBL (Multimeric Biotherapeutics Inc).

5. The use according to any one of items 1 to 4, wherein said cancer is selected from the group consisting of melanoma, including ocular, uveal and skin melanoma, head and neck cancer, renal cancer, Non-small cell lung cancer (NSCLC), microsatellite-instable carcinoma or lynch syndrome, including gastroesophageal and colorectal, urothelial carcinoma including bladder cancer, merkel cell carcinoma, hodgkin lymphoma, gastric cancer, microsatellite stable and instable gastrointestinal cancer including colorectal cancer (CRC), hepatocellular carcinoma (HCC), renal cell carcinoma (RCC), nasopharyngeal carcinoma, basal cell carcinoma, cervical cancer, anogenital cancers, Kaposi sarcoma, adult T-cell leukemia, primary effusion lymphoma, and Castlemann's disease.

6. The use according to any one of items 1 to 4, wherein said cancer is selected from the group consisting of breast cancer, including triple-negative breast cancer, oesophageal cancer, non-hodgkin lymphoma, small cell lung cancer (SCLC), sarkoma, mesothelioma, glioblastoma, microsatellite stable cancer (in particular gastroesophageal and colorectal), pancreas cancer, prostate cancer, cutaneous T-cell lymphoma (CTCL), and squamous cell carcinoma.

In certain embodiments (E)-N-(2-aminophenyl)-3-(1-((4-(1-methyl-1H-pyrazol-4-yl)phenyl)sulfonyl)-1H-pyrrol-3-yl)acrylamide is administered in a dose of 80 to 120, particularly 90 to 110, more particularly 95 to 105, even more particularly about 100 mg/day, or alternatively twice any of the aforementioned doses, or alternatively 4 times any of the aforementioned doses, wherein any of said daily doses are optionally administered in two portions (each half of the aforementioned amounts), twice daily, particularly one each in the morning and evening (wherein particularly the evening dose is administered 10-14, more particularly 11-13, even more particularly about 12 hours after the morning dose).

As used herein, an agonist is in particular a therapeutic agent interacting with a receptor, in the present case CD137, and activates said receptor, thereby producing or increasing the receptor's biological response.

In certain embodiments, the CD137 agonist may be selected from the group consisting of a, antibody, e.g. a monoclonal or bispecific monoclonal antibody, a fusion protein, a recombinant protein, an anticalin, an aptamer, an oncolytic virus, and a cellular immunotherapy.

In certain embodiments the CD137 agonist is selected from the group consisting of CD137 specific antibodies such as Utomilumab (PF-05082566), Urelumab (BMS-663513), ABP-300 (Abpro), EU-101 (Eutilex Co Ltd), or ATOR-1016 (Alligator Bioscience AB), CD137 specific anticalins such as PRS-343, or PRS-342 (Pieris Pharmaceuticals Inc), ET-140 or lisocabtagene maraleucel (Juno Therapeutics Inc), LOAd-703 (Lokon Pharma AB), KAHR-105 or KAHR-107 (KAHR medical Ltd), SCB-333 (Clover Biopharmaceuticals), MP-0310 (Molecular Partners AG), ISAS-01 (FasCure Therapeutics LLC), and Ultra-41BBL (Multimeric Biotherapeutics Inc).

In certain other embodiments the CD137 agonist is selected from the group consisting of INBRX-105 (Elpiscience Biopharmaceuticals Inc; INHIBRx LLC), ADG-106 (Adagene Suzhou Ltd), FS-120 (F-star Biotechnologische Forschungs-und Entwicklungs GmbH), CB-307 (Crescendo Biologics Ltd), STIM-41BBL (Merrimack Pharmaceuticals Inc), FS-222 (F-star Biotechnologische Forschungs-und Entwicklungs GmbH), PRS-344 (Pieris Pharmaceuticals Inc; Servier), GEN-1046 (BioNTech SE; Genmab Holding BV), AGEN-2373 (Agenus Inc), CD19-4-1 BBL (Roche Innovation Center Copenhagen A/S), AM-105 (AbClon Inc), CTX-471 (Compass Therapeutics LLC), TM-123+ UniCAR-T (Cellex GmbH; GEMoaB Monoclonals GmbH), RTX-240 (Rubius Therapeutics Inc), CUE-201 (Cue Biopharma Inc), RTX-224 (Rubius Therapeutics Inc), Utomilumab (PF-05082566), Urelumab (BMS-663513), ABP-300 (Abpro), EU-101 (Eutilex Co Ltd), ATOR-1016 (Alligator Bioscience AB), PRS-343, PRS-342 (Pieris Pharmaceuticals Inc), ET-140 or lisocabtagene maraleucel (Juno Therapeutics Inc), LOAd-703 (Lokon Pharma AB), KAHR-105 KAHR-107 (KAHR medical Ltd), SCB-333 (Clover Biopharmaceuticals), MP-0310 (Molecular Partners AG), ISAS-01 (FasCure Therapeutics LLC), and Ultra-41BBL (Multimeric Biotherapeutics Inc), particularly INBRX-105, ADG-106, Utomilumab, Urelumab, and lisocabtagene maraleucel, more particularly Utomilumab and Urelumab.

As used herein, anticalins are protein structures possessing the ability to specifically bind to a target (in the present case CD137) and show comparable binding strength and selectivity as antibodies binding to the same target. They are artificial proteins structurally derived from human lipocalins, and are smaller than typical antibodies with respect to their mass and number of amino acids. The Anticalin technology is commercialized by Pieris Pharmaceuticals, Germany. Certain specific anticalins are the ones detailed in WO 2016/177762 A1, WO 2016/177802 or WO 2016/184882.

In certain embodiments, the CD137 agonist is a molecule for which binding to and activation of CD137 is determinable, e.g. in an ELISA assay, e.g. an anti-CD137 antibody or an anti-CD137 anticalin, in particular with an EC50 250 nM or lower, more particularly 100 nM or lower, even more particularly 75 nM or lower. A particular ELISA usable in this context, in particular for biologicals, more particularly for antibodies, is the following assay:

Material & Methods:
CD137 agonist
Recombinant CD137, extracellular part of CD137 or chimeric proteins comprising extracellular part of CD137 (particularly human)
capture antibody specific to CD137 agonist, coupled to horse radish peroxidase (HRP)
ELISA Plate 96Well high binding (Greiner #655061)
PBS (e.g. Gibco #21300-058)
BSA (e.g. Sigma #A3733)
Tween20 (e.g. Sigma #P1379)
TMB (3,3',5,5'-Tetramethylbenzidin) ELISA substrate (e.g. 1-Step™ Ultra TMB-ELISA Substrate Solution by Thermo #34029)
Blocking solution: 1% BSA in PBS
Washing solution: PBS with 0.05% Tween
Stopping solution: sulphuric acid 250 mM 1. dissolve 0.1-1 µg/mL recombinant CD137, extracellular part of CD137 or chimeric proteins comprising extracellular part of CD137 in PBS, add 100 µL of said solution per well to ELISA 96 well plates, incubate the plates for 12-24 h at 4° C. (to coat the wells with CD137)
2. subsequently, remove solution and wash each well twice with 200 µL washing solution
3. subsequently add 200 µL of blocking solution per well, incubate at room temperature (about 22° C.) for 1 hour
4. subsequently, remove blocking solution and wash each well with 1×200 µL washing solution
5. subsequently, add 100 µL serial dilutions of CD137 agonist in PBS with 1% BSA to the respective wells (a particularly suitable range of serial dilutions could comprise 1 µM, 0.5 µM, 0.25 µM, 0.125 µM, 0.06 µM, 0.03 µM, 0.015 µM, 8 nM, 4 nM, 2 nM, 1 nM, 0.3 nM, 0.1 nM, 0.03 nM, 0.01 nM, 0.003 nM and 0.001 nM), incubate for 1 hour at room temperature
6. subsequently, remove supernatant and wash each well with 4× with 200 µL washing solution
7. subsequently, add 100 µL per well of capture antibody solution in PBS with 1% BSA) (e.g. goat anti human IgG-HRP, at 50 ng/ml to 5 µg/ml, typically to be determined by titration), incubate 45 min at room temperature
8. subsequently, remove supernatant and wash each well with 6× with 200 µL washing solution
9. subsequently, add 100 µL per well of TMB substrate
10. upon sufficient completion of the reaction (when a color gradient is visible between the different CD137 agonist dilutions, typically 5-20 minutes after substrate addition), add 100 µL 250 mM sulfuric acid per well (to stop the reaction)
11. subsequently, measure absorption at 450 nm in a suitable plate reader (e.g. Tecan Sunrise)
12. plot data as relative absorption at 450 nm versus CD137 agonist concentration and calculate $EC_{50}$ values using a suitable curve fit to a suitable pharmacological model (e.g. Emax model) using a suitable software (e.g. Graphpad Prism).

For instance, recombinant anti-CD137 and capture antibody can be, in specific forms of the assay: Goat anti-human IgG H&L (HRP): Abcam, ab6858; Recombinant Human 4 1BB/TNFRSF9/CD137: R&D Systems 9220-4B.

Alternatively, the CD137 agonist can be biotinylated using e.g. the Biotin (type B) conjugation Kit (Abcam, ab102867 according to manufacturer's instructions and detected using a Streptavidin-HRP conjugate, e.g. Streptavidin (HRP) (Abcam, ab7403).

Alternative competition format: The above assay procedure can be run in the competition format which is e.g. suitable to determine binding of small molecule CD137 agonists.

In step 5, add serial dilutions of CD137 agonists (a particularly suitable range of serial dilutions could comprise 1 µM, 0.5 µM, 0.25 µM, 0.125 µM, 0.06 µM, 0.03 µM, 0.015 µM, 8 nM, 4 nM, 2 nM, 1 nM, 0.3 nM, 0.1 nM, 0.03 nM, 0.01 nM, 0.003 nM and 0.001 nM) and add recombinant CD137 ligand (e.g. in serial dilutions in a matrix pattern versus serial dilutions of CD137 agonists to determine suitable concentration of CD137 ligand, which may be in a similar range as the aforementioned dilutions). In step 7, the capture antibody is specific for the recombinant CD137 ligand. Suitable $IC_{50}$ values are 100 nM or lower, particularly 75 nM or lower, more particularly 50 nM or lower.

The CD137 agonists may be small molecules (having a molecular weight of about 600 or lower, particularly 500 or lower, more particularly 400 or lower) or biologicals (as used herein such as antibodies, modified antibodies, antibody fragments and other proteins, e.g. anticalins).

In particular embodiments, the CD137 agonist is an antibody, more particularly a human antibody or a humanized antibody.

The CD137 agonist may be administered in a fixed dose, which means a dose that is equally administered to every patient that does not take into account the respective patient's body weight, in particular in the case of a biomolecule like an antibody or an anticalin.

The CD137 agonist is to be administered in a dose that is typically used by the physician for the respective CD137 agonist, in particular the dose approved by the respective governmental authorities. Typically, CD137 agonists that are biologicals (such as antibodies, modified antibodies, antibody fragments and other proteins) are to be administered only on day one of a treatment cycle, which may be a particular treatment cycle as described herein. This is due to their long half-life in the patient's system.

The term antibody in the meaning of the invention comprises all antibodies, antibody fragments, and derivatives thereof that are capable of binding to an antigen, in this case CD137. This encompasses the complete monoclonal antibodies and also the epitope-binding fragments of these antibodies. In this connection, the epitope binding fragments (also referred to herein as antibody fragments or antibody derivatives) comprise all regions of the antibody that are capable of binding to the antigen. Examples of particular antibody fragments in accordance with the invention comprise, but expressly are not limited to, Fab, Fab', F(ab')2, Fd, individual chain (single chain) variable fragments (scFv), single-chain antibodies, disulfide-linked variable fragments (sdFv), and fragments that either contain a variable region of the light chain ($V_L$) or a variable region of the heavy chain ($V_H$). Moreover, they include recombinantly prepared antibodies, such as diabodies, and tetrabodies.

Antibody fragments contain the variable regions either alone or in combination with further regions that are selected from the hinge region and the first, second and third regions of the constant region ($C_H1$, $C_H2$, $C_H3$). Also, the term antibody comprises chimeric antibodies in which different regions of the antibody originate from different species, for example, antibodies with a murine variable region combined with a human constant region.

Antibody fragments are optionally linked with each other by a linker. The linker comprises a short (particularly 10 to 20 amino acid residues), flexible peptide sequence that is selected such that the antibody fragment has such a three-dimensional folding of VL and VH that it exhibits the antigen specificity of the complete antibody. Particular linkers are glycine-serine linkers with the structure ($Gly_xSer_y$) with x and y selected from 1 to 10, particularly 3 to 5. Moreover, particular linkers are comprised of a peptide sequence that can increase the protease resistance of the antibody derivatives.

The treatment cycles as described herein can be repeated one or more times, and typically are repeated as often as necessary, which is typically to be determined by the physician, e.g. based on the disease state (progressive disease, stable disease, tumor regression, etc.), and/or the tolerability of the treatment.

In certain embodiments, the HDAC inhibitor may in each case be administered to a patient in a non-fasted state.

In certain embodiments, the cancer is a solid or hematological tumor;

In particular, "refractory" means no stabilization is achieved with therapy, "non-responding" means the best response achieved with therapy is stable disease for 6 months or less followed by disease progression, "relapsed" means temporary response shrinkage followed by disease progression, and wherein disease status including response, progression, stabilization may be determined e.g. according to RECIST or immune related RECIST (irRECIST) criteria version—reference Eisenhauer et al. 2009 Eur J Cancer, 45, 228-247; Nishino M et al., Clin Cancer Res. 2013 Jul. 15; 19(14):3936-4 3).

In certain particular embodiments, the cancer is an immunologically hot cancer. Immunologically hot means in particular that the tumor is sufficiently infiltrated by T-cells; visible by the immune system; exhibiting tumor antigen presentation, e.g. via MHC I or II. This can be determined e.g. via immune histochemistry, methods of which are well known in the field, such as for example the methods described in Arpita Kabiraj et al., Int J Biol Med Res. 2015; 6(3): 5204-5210 and references therein to the specific methods: Particularly, the cancer is a tumor with an immune cell infiltration corresponding to an immunoscore of 1 to 4, more particularly 2 to 4. In other embodiments, the cancer is immunologically cold cancer, in particular a tumor with an immune cell infiltration corresponding to an immunoscore of 0 to 2, more particularly 0 to 1. In other embodiments, the cancer is a tumor with an immune cell infiltration corresponding to an immunoscore of 2 to 3.

In certain embodiments, the subject or patient is refractory or non-responding or relapsed to, immune checkpoint inhibitor therapy, wherein non-responding relates in particular in particular to a response rate that is lower than 20%, more particularly lower than 10%, in particular lower than 10% in prospective clinical studies. In particular, said immune checkpoint inhibitor therapy is adaptive immunity-affecting Checkpoint Inhibitor therapy, more particularly a therapy comprising the administration of a PD-1, PD-L1 or CTLA-4 immune checkpoint inhibitor, wherein said immune checkpoint inhibitor may be administered alone or in combination with other active agents.

In certain embodiments, the cancer shows a PD-L1 expression of less than 1%, in particular compared to average expression in non-cancerous cells of the same cell type.

In other embodiments, the cancer shows a PD-L1 expression of 1% to 5%, in particular compared to average expression in non-cancerous cells of the same cell type.

In other embodiments, the cancer shows a PD-L1 expression of 5% to 50%, in particular compared to average expression in non-cancerous cells of the same cell type.

In other embodiments, the cancer shows a PD-L1 expression of greater than 50%, in particular compared to average expression in non-cancerous cells of the same cell type.

In certain embodiments, the cancer is negative predictive for efficacy to immune checkpoint inhibitor therapy. In other embodiments, the cancer is positive predictive for efficacy to immune checkpoint inhibitor therapy. In particular, said immune checkpoint inhibitor therapy is adaptive immunity-affecting Checkpoint Inhibitor therapy, more particularly a therapy comprising the administration of a PD-1, PD-L1 or CTLA-4 immune checkpoint inhibitor, wherein said immune checkpoint inhibitor may be administered alone or in combination with other active agents.

In certain embodiments, the cancer has a low or medium tumor mutational burden, in particular lower than 20, more particularly lower than 10 mutations per 1 million nucleotide bases. In other embodiments, the cancer has a high tumor mutational burden, in particular higher than 20 mutations per 1 million nucleotide bases.

Immunologically hot or cold tumors may in certain cases be determined based on certain cellular parameters, such as TGFbeta, PD-L1 and CD8 expression (as described in Mariathasan, S. et al. 2018, Nature. 554:544-548. doi: 10.1038/nature25501); mutational load (as described in Yarchoan, M. et al., 2017, N. Engl. J. Med. 377:2500-2501. doi:10.1056/NEJMc1713444); Immunoscore (based on localization, number and type of immune cells), (as described in Galon, J. et al. 2012, J. Transl. Med. 10:1. doi:10.1186/1479-5876-10-1); gut microbiome (degree of heterogeneity and prevalence of certain microbial species) (as described in Routy, B. et al., 2017, Science (80-.). 3706:

eaan3706. doi:10.1126/science.aan3706); immune cell populations and their effects on the prognosis of patients with cancer (as reviewed in Fridman, W. H. et al., 2017, Nat. Rev. Clin. Oncol. 5-8. doi:10.1038/nrclinonc.2017.101), and further factors as reviewed in (Ann Transl Med 2017; 5(23):468): baseline microbiome enriched with *Faecalibacterium* genus and other Firmicutes; neutrophil to lymphocyte ratio; neutrophil number and LDH (lactate dehydrogenase) level; relative eosinophil count and relative lymphocyte count; density of CD8+ T cells and beta-catenin; presence or absence of JAK 2 (Janus kinase 2) and beta-2-microglobulin mutations; TIM-3 (T-cell immunoglobulin mucin-3) level; mutational load; level of tumor tetrapeptide sequences capable of binding to MHC class I molecules (neoantigens); neoantigen intratumor heterogeneity and a amount of clonal neoantigen burden; PD-L1 (programmed death-1 receptor ligand) expression level; PTEN (phosphatase and tensin homolog) expression level; CD8+ T cell expansion; broadness of T cell receptor repertoire (per beta chain) at baseline.

In certain particular embodiments, the cancer is suitable for treatment with a CD137 agonist, wherein this is particularly a cancer for which a CD137 agonist therapy is approved, i.e. that has received market approval by the regulatory authorities in at least one country.

In certain particular embodiments, the cancer is selected from the group consisting of melanoma (in particular ocular and uveal, but also including skin melanoma), head and neck, renal, Non-small cell lung cancer (NSCLC), microsatellite-instable carcinoma (lynch syndrome, in particular gastroesophageal and colorectal), urothelial carcinoma including bladder cancer, merkel cell carcinoma, hodgkin lymphoma, gastric cancer, gastrointestinal cancer (microsatellite stable and instable) including colorectal cancer (CRC), hepatocellular carcinoma (HCC), renal cell carcinoma (RCC), nasopharyngeal carcinoma, basal cell carcinoma, cervical cancer, anogenital cancers, Kaposi sarcoma, adult T-cell leukemia, primary effusion lymphoma, and Castlemann's disease.

In certain particular embodiments, the cancer is selected from the group consisting of breast cancer, in particular triple-negative breast cancer, oesophageal cancer, non-hodgkin lymphoma, small cell lung cancer (SCLC), sarkoma, mesothelioma, glioblastoma, microsatellite stable cancer (in particular gastroesophageal and colorectal), pancreas cancer, prostate cancer, cutaneous T-cell lymphoma (CTCL), and squamous cell carcinoma.

The number of immune cells and/or its ratio versus the total cell number in a tumor in the context of the present invention is determinable by standard methods known to the skilled person and in particular embodiments determinable in a formalin-fixed paraffin-embedded tumor sample obtainable from the patient by 1) cutting a 5-10 μM slice of said sample,
2) fixing the slices in 4% PF (paraffin),
3) rinsing twice in PBS for 2 minutes,
4) adding commercially available serum (5% in PBS) and incubating for 20 minutes,
5) adding a primary commercially available antibody against CD3+ or CD8+ and incubating for 60 min (dilution of 5 μg/ml in PBS),
6) rinsing twice in PBS for 2 minutes,
7) adding a secondary biotinylated antibody (binding to the constant region of the primary antibody) and incubating for 30 min,
8) rinsing twice in PBS for 2 minutes,
9) add streptavidin-peroxidase (e.g. Jackson Immunoresearch), incubate for 30 min,
10) rinsing twice in PBS for 2 minutes,
11) add developer (e.g. AEC Substrate Chromogen Ready-to-Use, Dako #K3464), particularly until sufficiently stained (typically observe development under microscope, typically for 5 min)
12) rinse with water
13) counterstain with commercially available HTX solution
14) mount in water-based mounting media (e.g. DAKO)
15) determine CD3+ or CD8+ cell number
16) optionally determine cell number ratio by dividing CD3+ or CD8+ cell number by total cell number in tumor volume (e.g. based on typical cell numbers in said specific cancer type);

Or by the following assay

For each tumor sample, stain 2 slides are using an automated immunohistochemistry staining instrument (BenchMark XT, Ventana): one with CD3 and one with CD8 ready-to-use monoclonal antibodies (HalioDx).

Perform staining with ultraView Universal DAB Detection Kit (Ventana), followed by counterstaining (Bluing Reagent, Ventana).

Wash stained slides, dehydrate, mount and coverslip.

Obtain digital images of stained slides using a whole slide scanner (Nanozoomer XR, Hamamatsu), and analyze by a software program (Immunoscore® Analyzer, HalioDx) or count to determine cell numbers and optionally determine ratio as above.

(Optional: One separate control slide with 3 external controls—1 negative tissue (placenta) and 2 positive (1 tissue: tonsil and a cell line pellet)—is processed identically in each IHC run, and allows monitoring of the staining and scanning steps.)

In certain embodiments the patient having said cancer has received at least one prior systemic treatment against said cancer,
- e.g. at least one prior systemic chemotherapeutic treatment against said cancer,
- e.g. at least one prior systemic treatment comprising the administration of a CD137 agonist.

In certain embodiments of the present invention, said prior systemic chemotherapeutic treatment is a treatment of administrating one or more chemotherapeutic agents systemically, such chemotherapeutic agent may be used alone or in combination with further agents.

In certain embodiments of the present invention, said patient having said cancer has received at least one prior systemic treatment comprising the administration of a CD137 agonist against said cancer and said patient was a non-responder or said cancer was refractory or relapsed to said at least one prior systemic treatment.

In the present invention, the treatment may be the treatment of a subject suffering from cancer, in particular a human subject suffering from cancer, in particular the specific cancer types described herein. Said subject may also be addressed as a patient, as used herein in certain contexts.

The HDAC inhibitor is meant to be inclusive of the respective salts, solvates and hydrates.

In the present invention, the HDAC inhibitor and the CD137 agonist are typically to be administered in therapeutically effective amounts.

The HDAC inhibitor is in a first aspect (aspect A) a compound of formula I

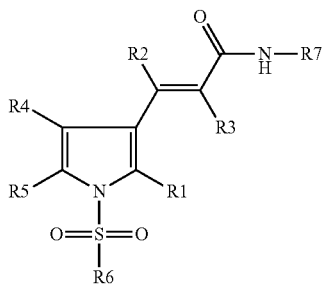

(I)

in which

R1, R4 and R5 are independently hydrogen, 1-4C-alkyl, halogen, or 1-4C-alkoxy,

R2 and R3 are independently hydrogen or 1-4C-alkyl,

R6 is -T1-Q1, in which T1 is a bond or 1-4C-alkylene, either

Q1 is substituted by R61 and/or R62, and is Aa1, Hh1, Ha1, Ha2, Ha3, Ha4 or Ah1, or Q1 is unsubstituted, and is Ha2, Ha3 or Ha4, in which R61 is 1-4C-alkyl, phenyl-1-4C-alkyl, 1-4C-alkoxy, hydroxyl, trifluoromethyl, cyano, halogen, completely fluorine-substituted 1-4C-alkoxy or 1-4C-alkoxy wherein more than half of the hydrogen atoms are replaced by fluorine atoms, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, —U-T3-N(R613)R614, -T4-Het3, or —V-T5-Het4, in which T2 is a bond or 1-4C-alkylene, R611 is hydrogen, 1-4C-alkyl, 3-7C-cycloalkyl, 3-7C-cycloalkylmethyl, hydroxy-2-4C-alkyl, 1-4C-alkoxy-2-4C-alkyl, 1-4C-alkylcarbonyl, or 1-4C-alkylsulphonyl, R612 is hydrogen or 1-4C-alkyl, or R611 and R612 together and with inclusion of the nitrogen atom, to which they are bonded, form a heterocyclic ring Het1, in which Het1 is morpholino, thiomorpholino, S-oxo-thiomorpholino, S,S-dioxothiomorpholino, piperidino, pyrrolidino, piperazino, or 4N-(1-4C-alkyl)-piperazino, U is —O— (oxygen) or —C(O)NH—, T3 is 2-4C-alkylene, R613 is hydrogen, 1-4C-alkyl, 3-7C-cycloalkyl, 3-7C-cycloalkylmethyl, hydroxy-2-4C-alkyl or 1-4C-alkoxy-2-4C-alkyl, 1-4C-alkylcarbonyl, or 1-4C-alkylsulphonyl R614 is hydrogen or 1-4C-alkyl, or R613 and R614 together and with inclusion of the nitrogen atom, to which they are bonded, form a heterocyclic ring Het2, in which Het2 is morpholino, thiomorpholino, S-oxo-thiomorpholino, S,S-dioxo-thiomorpholino, piperidino, pyrrolidino, piperazino, or 4N-(1-4C-alkyl)-piperazino, T4 is a bond or 1-4C-alkylene, Het3 is 1N-(1-4C-alkyl)-piperidinyl or 1N-(1-4C-alkyl)-pyrrolidinyl, V is —O— (oxygen) or —C(O)NH—, T5 is a bond or 1-4C-alkylene, Het4 is 1N-(1-4C-alkyl)-piperidinyl or 1N-(1-4C-alkyl)-pyrrolidinyl, R62 is 1-4C-alkyl, 1-4C-alkoxy or halogen, Aa1 is a bisaryl radical made up of two aryl groups,
which are selected independently from a group consisting of phenyl and naphthyl, and
which are linked together via a single bond, Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond, Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group, Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group, Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group, Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, Ha4 is a heteroarylaryl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha4 is bonded via said aryl moiety to the to the parent molecular group, R7 is hydroxyl, or Cyc1, in which Cyc1 is a ring system of formula Ia

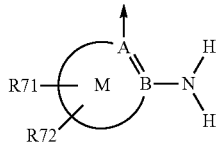

(Ia)

in which

A and B are C (carbon),

R71 and R72 are independently hydrogen, halogen, 1-4C-alkyl, or 1-4C-alkoxy,

M with inclusion of A and B is either a ring Ar2 or a ring Har2, in which Ar2 is a benzene ring, Har2 is a monocyclic 5- or 6-membered unsaturated heteroaromatic ring comprising one to three heteroatoms, each of which is selected from the group consisting of nitrogen, oxygen and sulfur, and the salts of these compounds.

The HDAC inhibitor is in a second aspect (aspect B), which is an embodiment of aspect A, a compound of formula I, in which R1, R4 and R5 are independently hydrogen, 1-4C-alkyl, halogen, or 1-4C-alkoxy, R2 and R3 are independently hydrogen or 1-4C-alkyl, R6 is -T1-Q1, in which T1 is a bond or 1-4C-alkylene, either Q1 is substituted by R61 and/or R62, and is Aa1, Hh1, Ha1, Ha2, Ha3 or Ah1, or Q1 is unsubstituted, and is Ha2 or Ha3, in which R61 is 1-4C-alkyl, phenyl-1-4C-alkyl, 1-4C-alkoxy, hydroxyl, trifluoromethyl, cyano, halogen, completely fluorine-substituted 1-4C-alkoxy or 1-4C-alkoxy wherein more than half of the hydrogen atoms are replaced by fluorine atoms, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, or —U-T3-N(R613)R614, in which T2 is a bond or 1-4C-alkylene, R611 is hydrogen, 1-4C-alkyl, 3-7C-cycloalkyl, 3-7C-cycloalkylmethyl, hydroxy-2-4C-alkyl or 1-4C-alkoxy-2-4C-alkyl, R612 is hydrogen or 1-4C-alkyl, or R611 and R612 together and with inclusion of the nitrogen atom, to which they are bonded, form a heterocyclic ring Het1, in which Het1 is morpholino, thiomorpholino, S-oxo-thiomorpholino, S,S-dioxo-thiomorpholino, piperidino, pyrrolidino, piperazino, or 4N-(1-4C-alkyl)-piperazino, U is —O— (oxygen) or —C(O)NH—, T3 is 2-4C-alkylene, R613 is hydrogen, 1-4C-alkyl, 3-7C-cycloalkyl, 3-7C-cycloalkylmethyl, hydroxy-2-4C-alkyl or 1-4C-alkoxy-2-4C-alkyl, R614 is hydrogen or 1-4C-alkyl, or R613 and R614 together and with inclusion of the nitrogen atom, to which they are bonded, form a heterocyclic ring Het2, in which Het2 is morpholino, thiomorpholino, S-oxo-thiomorpholino, S,S-dioxo-thiomorpholino, piperidino, pyrrolidino, piperazino, or 4N-(1-4C-alkyl)-piperazino, R62 is 1-4C-alkyl, 1-4C-alkoxy or halogen, Aa1 is a bisaryl radical made up of two aryl groups,
which are selected independently from a group consisting of phenyl and naphthyl, and
which are linked together via a single bond, Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond, Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group, Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group, Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group, Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, R7 is hydroxyl, or Cyc1, in which Cyc1 is a ring system of formula Ia

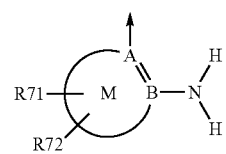

(Ia)

in which

A and B are C (carbon),

R71 and R72 are independently hydrogen, halogen, 1-4C-alkyl, or 1-4C-alkoxy,

M with inclusion of A and B is either a ring Ar2 or a ring Har2, in which

Ar2 is a benzene ring,

Har2 is a monocyclic 5- or 6-membered unsaturated heteroaromatic ring comprising one to three heteroatoms, each of which is selected from the group consisting of nitrogen, oxygen and sulfur, and the salts of these compounds.

The HDAC inhibitor is in a third aspect (aspect C), which is also an embodiment of aspect A, a compound of formula I, in which R1, R4 and R5 are independently hydrogen, 1-4C-alkyl, halogen, or 1-4C-alkoxy, R2 and R3 are independently hydrogen or 1-4C-alkyl, R6 is -T1-Q1, in which T1 is a bond, or 1-4C-alkylene, either Q1 is substituted by R61 and/or R62, and is Aa1, Hh1, Ha1, Ha2, Ha3 or Ah1, or Q1 is unsubstituted, and is Ha2 or Ha3, in which R61 is 1-4C-alkyl, 1-4C-alkoxy, hydroxyl, trifluoromethyl, cyano, halogen, completely fluorine-substituted 1-4C-alkoxy or 1-4C-alkoxy wherein more than half of the hydrogen atoms are replaced by fluorine atoms, or -T2-N(R611)R612, in which T2 is a bond or 1-4C-alkylene, R611 and R612 are independently hydrogen or 1-4C-alkyl, or R611 and R612 together and with inclusion of the nitrogen atom, to which they are bonded, form a heterocyclic ring Het1, in which Het1 is morpholino, thiomorpholino, S-oxo-thiomorpholino, S,S-dioxo-thiomorpholino, piperidino, pyrrolidino, piperazino, or 4N-(1-4C-alkyl)-piperazino, R62 is 1-4C-alkyl, 1-4C-alkoxy or halogen, Aa1 is a bisaryl radical made up of two aryl groups,
which are selected independently from a group consisting of phenyl and naphthyl, and
which are linked together via a single bond, Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond, Ah1 is an aryl-heteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group, Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group, Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group, Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, R7 is hydroxyl, or Cyc1, in which Cyc1 is a ring system of formula Ia

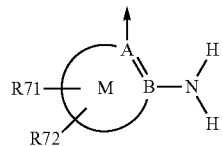

(Ia)

in which

A and B are C (carbon),

R71 and R72 are independently hydrogen, halogen, 1-4C-alkyl, or 1-4C-alkoxy,

M with inclusion of A and B is either a ring Ar2 or a ring Har2, in which Ar2 is a benzene ring, Har2 is a monocyclic 5- or 6-membered unsaturated heteroaromatic ring comprising one to three heteroatoms, each of which is selected from the group consisting of nitrogen, oxygen and sulfur, and the salts of these compounds.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and particularly the ethyl and methyl radicals.

2-4C-Alkyl represents a straight-chain or branched alkyl radical having 2 to 4 carbon atoms. Examples which may be mentioned are the butyl, isobutyl, sec-butyl, tert-butyl, propyl, isopropyl and particularly the ethyl radicals.

3-7C-Cycloalkyl stands for cyclopropyl, cyclobutyl, cyclopentyl, cyclohexyl and cycloheptyl, of which cyclopropyl, cyclobutyl and cyclopentyl are particular examples.

3-7C-Cycloalkylmethyl stands for a methyl radical, which is substituted by one of the abovementioned 3-7C-cycloalkyl radicals. Particular examples which may be mentioned are the cyclopropylmethyl, the cyclobutylmethyl and the cyclopentylmethyl radicals.

1-4C-Alkylene is a branched or, particularly, straight chain alkylene radical having 1 to 4 carbon atoms. Examples which may be mentioned are the methylene (—CH$_2$—), ethylene (dimethylene) (—CH₂—CH₂—), trimethylene (—CH₂—CH₂—CH₂—) and the tetramethylene (—CH₂—CH₂—CH₂—CH₂—) radical.

2-4C-Alkylene is a branched or, particularly, straight chain alkylene radical having 2 to 4 carbon atoms. Examples which may be mentioned are the ethylene (dimethylene) (—CH₂—CH₂—), trimethylene (—CH₂—CH₂—CH₂—) and the tetramethylene (—CH₂—CH₂—CH₂—CH₂—) radical.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and particularly the ethoxy and methoxy radicals.

1-4C-Alkoxy-1-4C-alkyl stands for one of the abovementioned 1-4C-alkyl radicals, which is substituted by one of the abovementioned 1-4C-alkoxy radicals. Examples which may be mentioned are the methoxymethyl, 2-methoxyethyl, 3-methoxypropyl and the 2-ethoxyethyl radical.

1-4C-Alkoxy-2-4C-alkyl stands for one of the abovementioned 2-4C-alkyl radicals, which is substituted by one of the abovementioned 1-4C-alkoxy radicals. Examples which may be mentioned are the 2-methoxyethyl, 3-methoxypropyl and the 2-ethoxyethyl radical.

Hydroxy-1-4C-alkyl stands for one of the abovementioned 1-4C-alkyl radicals which is substituted by hydroxyl. Examples which may be mentioned are the hydroxymethyl radical, the 2-hydroxyethyl radical or the 3-hydroxypropyl radical.

Hydroxy-2-4C-alkyl stands for one of the abovementioned 2-4C-alkyl radicals which is substituted by hydroxyl. Examples which may be mentioned are the 2-hydroxyethyl radical or the 3-hydroxypropyl radical.

Phenyl-1-4C-alkyl represents one of the abovementioned 1-4C-alkyl radicals, which is substituted by a phenyl radical. Examples which may be mentioned are the benzyl and phenethyl radicals.

Mono- or Di-1-4C-alkylamino radicals contain in addition to the nitrogen atom, one or two of the abovementioned 1-4C-alkyl radicals. Particular examples red are the di-1-4C-alkylamino radicals, especially the dimethylamino, the diethylamino and the diisopropylamino radical.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical, of which the N,N-dimethylaminocarbonyl radical is a particular example.

Mono- or Di-1-4C-alkylaminosulphonyl stands for a sulphonyl group to which one of the abovementioned mono- or di-1-4C-alkylamino radicals is bonded. Examples which may be mentioned are the methylaminosulphonyl, the dimethylaminosulphonyl and the ethylaminosulphonyl radical, of which the N,N-dimethylaminosulphonyl (dimethylsulphamoyl) radical [(CH₃)₂NS(O)₂—] is a particular example.

An 1-4C-Alkylcarbonylamino radical is, for example, the propionylamino (C₂H₅C(O)NH—) and the acetylamino (acetamido) radical (CH₃C(O)NH—).

An 1-4C-Alkylsulphonylamino radical is, for example, the ethanesulphonylamino (ethylsulphonylamino) (C₂H₅S(O)₂NH—) and the methanesulphonylamino (methylsulphonylamino) radical (CH₃S(O)₂NH—).

1-4C-Alkylsulfonyl is a sulfonyl group to which one of the abovementioned 1-4C-alkyl radicals is bonded. An example is the methanesulphonyl (methylsulphonyl) radical (CH₃SO₂—).

1-4C-Alkylcarbonyl is a carbonyl group to which one of the abovementioned 1-4C-alkyl radicals is bonded. An example is the acetyl radical (CH₃CO—).

Tolyl alone or as part of another group includes o-tolyl, m-tolyl and p-tolyl.

Halogen within the meaning of the invention is bromine or, in particular, chlorine or fluorine.

Aa1 is a bisaryl radical made up of two aryl groups,
which are selected independently from a group consisting of phenyl and naphthyl, and
which are linked together via a single bond.

Aa1 may include, without being restricted thereto, the biphenyl radical, e.g. the 1,1'-biphenyl-4-yl or 1,1'-biphenyl-3-yl radical.

As non-limiting examples of R61-substituted derivatives of Aa1 may be mentioned the following radicals:

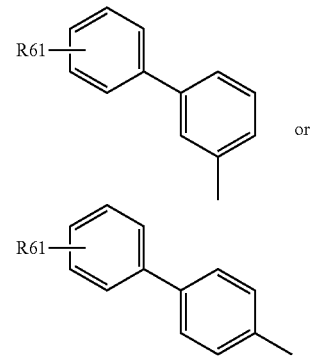

in which the substituent R61 can be attached in the ortho, or, in particular, meta or para position with respect to the binding position in which the benzene ring is bonded to the phenyl radical, such as e.g. 2'-(R61)-1,1'-biphenyl-3-yl, 2'-(R61)-1,1'-biphenyl-4-yl, or, in particular, 3'-(R61)-1,1'-biphenyl-3-yl or 3'-(R61)-1,1'-biphenyl-4-yl, or, yet in particular, 4'-(R61)-1,1'-biphenyl-3-yl or 4'-(R61)-1,1'-biphenyl-4-yl.

As exemplary R61-substituted Aa1 radicals may be more detailed mentioned, for example, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is -T2-N(R611)R612, in which
T2 is methylene, dimethylene or trimethylene, and
R611 and R612 together and with inclusion of the nitrogen atom, to which they are bonded, form a morpholino or 4N-methyl-piperazino, or a piperidino or pyrrolidino radical; such as, for example, any selected from
3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl and 4'-(4-methyl-piperazin-1-ylmethyl)-biphenyl-3-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
  R61 is -T2-N(R611)R612, in which T2 is methylene, dimethylene or trimethylene, and
  R611 and R612 are both methyl;
  such as, for example, any selected from
2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl and 3'-dimethylaminomethyl-biphenyl-3-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
  R61 is -T2-N(R611)R612, in which
  T2 is methylene, dimethylene or trimethylene, and
  R611 is hydrogen, cyclopropyl, cyclopentyl, 2-methoxyethyl, acetyl or methylsulfonyl,
  R612 is hydrogen;
  for example,
  either
  R611 is
  cyclopropyl or 2-methoxyethyl, and
  R612 is
  hydrogen,
  such as, for example, any selected from
4'-(2-methoxy-ethylamino)methyl-biphenyl-3-yl and 4'-cyclopropylaminomethyl-biphenyl-3-yl, or
  R611 is hydrogen, cyclopentyl, acetyl or methylsulfonyl, and
  R612 is hydrogen,
  such as, for example, any selected from
4'-aminomethyl-biphenyl-3-yl, 4'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl and 4'-cyclopentylaminomethyl-biphenyl-4-yl.

Yet as exemplary R61-substituted Aa1 radicals may be more detailed mentioned, for example, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
  R61 is —O-T3-N(R613)R614, in which T3 is dimethylene or trimethylene, and
  R613 and R614 together and with inclusion of the nitrogen atom, to which they are bonded, form a morpholino, pyrrolidino or 4N-methyl-piperazino, or a piperidino radical;
  such as, for example, any selected from
4'-(2-morpholin-4-yl-ethoxy)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-(2-pyrrolidin-1-yl-ethoxy]-biphenyl-3-yl, 3'-(3-pyrrolidin-1-yl-propoxy]-biphenyl-4-yl, 4'-(3-pyrrolidin-1-yl-propoxy]-biphenyl-4-yl, 3'-(2-pyrrolidin-1-yl-ethoxy]-biphenyl-4-yl, 4'-(3-morpholin-4-yl-propoxy)-biphenyl-4-yl, 3'-(3-morpholin-4-yl-propoxy)-biphenyl-4-yl, 3'-(2-morpholin-4-yl-ethoxy)-biphenyl-4-yl, 4'-(2-morpholin-4-yl-ethoxy)-biphenyl-4-yl, 4'-[2-(4-methyl-piperazin-1-yl)-ethoxy]-biphenyl-4-yl, 4'-[3-(4-methyl-piperazin-1-yl)-propoxy]-biphenyl-4-yl and 3'-[3-(4-methyl-piperazin-1-yl)-propoxy]-biphenyl-4-yl.

Yet as exemplary R61-substituted Aa1 radicals may be more detailed mentioned, for example, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
  R61 is —O-T5-Het4, in which T5 is a bond, methylene, dimethylene or trimethylene, and Het4 is 1-methyl-piperidin-4-yl;
  such as e.g. 4'-(2-(1-methyl-piperidin-4-yl)-ethoxy)-biphenyl-4-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
  R61 is methylsulphonylamino, N,N-dimethylaminosulphonyl, acetamido, hydroxymethyl, amino, dimethylamino, morpholino, hydroxyl, trifluoromethyl or methoxy;
  for example,
  either
  R61 is methylsulphonylamino, N,N-dimethylaminosulphonyl, acetamido or hydroxymethyl, such as, for example, any selected from 2'-methylsulphonylamino-biphenyl-4-yl, 3'-methylsulphonylamino-biphenyl-4-yl, 4'-methylsulphonylamino-biphenyl-4-yl, 4'-methylsulphonylamino-biphenyl-3-yl, 4'-dimethylsulphamoyl-biphenyl-4-yl, 3'-acetamido-biphenyl-4-yl, 4'-acetamido-biphenyl-4-yl and 3'-hydroxymethyl-biphenyl-4-yl, or
  R61 is amino, dimethylamino, morpholino, hydroxyl, trifluoromethyl or methoxy, such as, for example, any selected from 3'-amino-biphenyl-4-yl, 4'-morpholin-4-yl-biphenyl-4-yl, 4'-hydroxy-biphenyl-4-yl, 3'-trifluoromethyl-biphenyl-4-yl, 3'-dimethylamino-biphenyl-4-yl and 4'-methoxy-biphenyl-4-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
  R61 is —C(O)—N(H)-T3-N(R613)R614, in which T3 is dimethylene or trimethylene, and R613 and R614 are both methyl;
  such as, for example, any selected from
3'-[(2-dimethylamino-ethylamino)-carbonyl]-biphenyl-4-yl, 4'-[(2-dimethylamino-ethylamino)-carbonyl]-biphenyl-4-yl and 4'-[(2-dimethylamino-ethylamino)-carbonyl]biphenyl-3-yl.

An example of R61-substituted Aa1 radicals may be 3'-(R61)-1,1'-biphenyl-3-yl, in which R61 is any one selected from the group $G_{Aa1}$ consisting of 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl.

Another example of R61-substituted Aa1 radicals may be 3'-(R61)-1,1'-biphenyl-4-yl, in which R61 is any one selected from the group $G_{Aa1}$ given above.

Another example of R61-substituted Aa1 radicals may be 4'-(R61)-1,1'-biphenyl-3-yl, in which R61 is any one selected from the group $G_{Aa1}$ given above.

Another example of R61-substituted Aa1 radicals may be 4'-(R61)-1,1'-biphenyl-4-yl, in which R61 is any one selected from the group $G_{Aa1}$ given above.

Specifically, as an exemplary R61-substituted Aa1 radical may be explicitly mentioned, for example, any one selected from 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl, 4'-(4-methyl-piperazin-1-ylmethyl)-biphenyl-3-yl, 4'-(2-morpholin-4-yl-ethoxy)-biphenyl-3-yl, 4'-(3-morpholin-4-yl-propoxy)-biphenyl-3-yl, 4'-[2-(4-methyl-piperazin-1-yl)-ethoxy]biphenyl-3-yl, 4'-(2-pyrrolidin-1-yl-ethoxy] biphenyl-3-yl, 3'-(3-pyrrolidin-1-yl-propoxy]-biphenyl-4-yl, 4'-(3-pyrrolidin-1-yl-propoxy]-biphenyl-4-yl, 3'-(2-pyrrolidin-1-yl-ethoxy]biphenyl-4-yl, 4'-(3-morpholin-4-yl-propoxy)-biphenyl-4-yl, 3'-(3-morpholin-4-yl-propoxy)-biphenyl-4-yl, 3'-(2-morpholin-4-yl-ethoxy)-biphenyl-4-yl, 4'-(2-morpholin-4-yl-ethoxy)-biphenyl-4-yl, 4'-[2-(4-methyl-piperazin-1-yl)-ethoxy]-biphenyl-4-yl, 4'-[3-(4-methyl-piperazin-1-yl)-propoxy]-biphenyl-4-yl, 3'-[3-(4-methyl-piperazin-1-yl)-propoxy]-biphenyl-4-yl, 4'-(2-(1-methyl-piperidin-4-yl)-ethoxy)-biphenyl-4-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl, 3'-dimethylaminomethyl-biphenyl-3-yl, 3'-[(2-dimethylamino-ethylamino)-carbonyl]-biphenyl-4-yl, 4'-[(2-dimethylamino-ethylamino)-carbonyl]-biphenyl-4-yl, 4'-[(2-dimethylamino-ethylamino)-carbonyl]biphenyl-3-yl, 2'-methylsulphonylamino-biphenyl-4-yl, 3'-methylsulphonylamino-biphenyl-4-yl, 4'-methylsulphonylamino-biphenyl-4-yl, 4'-methylsulphonylamino-biphenyl-3-yl, 4'-dimethylsulphamoyl-biphenyl-4-yl, 3'-acetamido-biphenyl-4-yl, 4'-acetamido-biphenyl-4-yl, 3'-amino-biphenyl-4-yl, 4'-morpholin-4-yl-biphenyl-4-yl, 4'-hydroxy-biphenyl-4-yl, 3'-trifluoromethyl-biphenyl-4-yl and 4'-methoxy-biphenyl-4-yl, 4'-(2-methoxy-ethylamino)methyl-biphenyl-3-yl, 4'-aminomethyl-biphenyl-3-yl, 4'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl, 4'-cyclopentylaminomethyl-biphenyl-4-yl, 4'-cyclopropylaminomethyl-biphenyl-3-yl, and 3'-hydroxymethyl-biphenyl-4-yl.

More specifically, as an exemplary R61-substituted Aa1 radical may be more explicitly mentioned, for example, any one selected from 4'-(2-morpholin-4-yl-ethyl)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, and 4'-dimethylaminomethyl-biphenyl-4-yl.

Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond.

Hh1 may include, without being restricted thereto, the bithiophenyl e.g. thiophen-3-yl-thiophenyl or thiophen-2-yl-thiophenyl, bipyridyl, pyrazolyl-pyridinyl e.g. pyrazol-1-yl-pyridinyl or pyrazol-4-yl-pyridinyl like 6-(pyrazol-4-yl)-pyridin-3-yl, imidazolyl-pyridinyl e.g. imidazol-1-yl-pyridinyl, pyrazolyl-thiophenyl e.g. pyrazol-4-yl-thiophenyl like 5-(pyrazol-4-yl)-thiophen-2-yl, or pyridinyl-thiophenyl radical e.g. pyridin-2-yl-thiophenyl, pyridin-3-yl-thiophenyl or pyridin-4-yl-thiophenyl like 5-(pyridin-2-yl)-thiophen-2-yl or 5-(pyridin-4-yl)-thiophen-2-yl, or the thiazolyl-thiophenyl e.g. thiazol-4-yl-thiophenyl like 5-(thiazol-4-yl)-thiophen-2-yl, or thiazolyl-pyridinyl radical like 6-(thiazol-4-yl)-pyridin-3-yl.

In a special detail, exemplary Hh1 radicals may include pyridinyl-thiophenyl, e.g. 5-(pyridin-4-yl)-thiophen-2-yl. In another special detail, exemplary Hh1 radicals may include pyrazolyl-thiophenyl, e.g. 5-(pyrazol-4-yl)-thiophen-2-yl. In another special detail, exemplary Hh1 radicals may include bipyridyl, e.g. 2,4'-bipyridyl-5-yl. In another special detail, exemplary Hh1 radicals may include thiazolyl-thiophenyl, e.g. 5-(thiazol-4-yl)-thiophen-2-yl. In another special detail, exemplary Hh1 radicals may include pyrazolyl-pyridinyl, e.g. 6-(pyrazol-4-yl)-pyridin-3-yl. In another special detail, exemplary Hh1 radicals may include thiazolyl-pyridinyl, e.g. 6-(thiazol-4-yl)-pyridin-3-yl.

As non-limiting example of R61-substituted derivatives of Hh1 may be mentioned [1N-(1-4C-alkyl)-pyrazolyl]-thiophenyl, such as e.g. [1N-(1-4C-alkyl)-pyrazol-4-yl]-thiophenyl, like 5-[1N-(1-2C-alkyl)-pyrazol-4-yl]-thiophen-2-yl, e.g. 5-(1 N-methyl-pyrazol-4-yl)-thiophen-2-yl.

Yet as non-limiting example of R61-substituted derivatives of Hh1 may be mentioned [1N-(1-4C-alkyl)-pyrazolyl]-pyridinyl, such as e.g. [1N-(1-4C-alkyl)-pyrazol-4-yl]-pyridinyl or 6-[1N-(1-4C-alkyl)-pyrazolyl]-pyridin-3-yl, like 6-[1N-(1-2C-alkyl)-pyrazol-4-yl]-pyridin-3-yl, e.g. 6-(1N-methyl-pyrazol-4-yl)-pyridin-3-yl.

Yet as non-limiting example of R61-substituted derivatives of Hh1 may be mentioned [(R61)-pyridinyl]-thiophenyl, such as e.g. the following radicals:

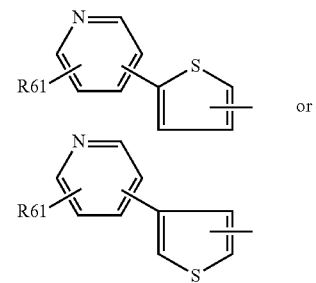

or in which the substituent R61 can be attached in the ortho, or, in particular, meta or para position with respect to the binding position in which the pyridinyl ring is bonded to the thiophenyl radical, such as e.g. [2-(R61)-pyridin-4-yl]-thiophenyl or [6-(R61)-pyridin-3-yl]-thiophenyl, like 5-[2-(R61)-pyridin-4-yl]-thiophen-2-yl or 5-[6-(R61)-pyridin-3-yl]-thiophen-2-yl.

Yet as non-limiting example of R61-substituted derivatives of Hh1 may be mentioned [(R61)-thiazolyl]-thiophenyl, such as e.g. the following radicals:

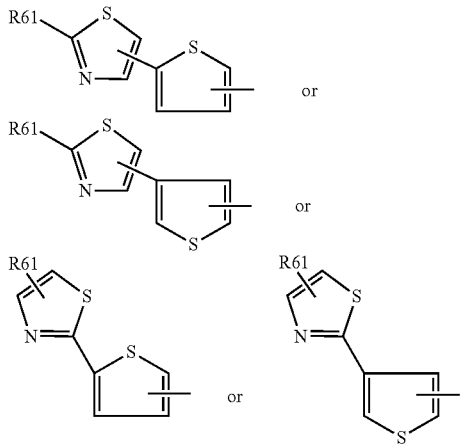

such as e.g. [2-(R61)-thiazol-4-yl]thiophenyl, like 5-[2-(R61)-thiazol-4-yl]-thiophen-2-yl.

Yet as non-limiting example of R61-substituted derivatives of Hh1 may be mentioned [(R61)-pyridinyl]-pyridinyl, such as e.g. the following radicals:

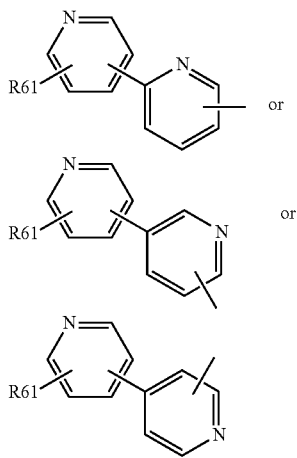

in which the substituent R61 can be attached in the ortho, or, in particular, meta or para position with respect to the binding position in which the terminal pyridinyl ring is bonded to the other pyridinyl radical, such as e.g. [2-(R61)-pyridin-4-yl]pyridinyl or [6-(R61)-pyridin-3-yl]-pyridinyl or 6-[(R61)-pyridinyl]-pyridin-3-yl, like 6-[2-(R61)-pyridin-4-yl]-pyridin-3-yl [i.e. 2'-(R61)-2,4'-bipyridyl-5-yl] or 6-[6-(R61)-pyridin-3-yl]-pyridin-3-yl [i.e. 6'-(R61)-2,3'-bipyridyl-5-yl].

As exemplary R61-substituted Hh1 radicals may be more detailed mentioned, for example, 5-[2-(R61)-pyridin-4-yl]-thiophen-2-yl or 5-[6-(R61)-pyridin-3-yl]-thiophen-2-yl, in which
R61 is -T2-N(R611)R612, in which T2 is a bond, and
R611 and R612 are both hydrogen, or
R611 and R612 together and with inclusion of the nitrogen atom, to which they are bonded, form a morpholino or 4N-methyl-piperazino, or a piperidino or pyrrolidino radical;

such as e.g. 5-[2-(4-methyl-piperazin-1-yl)-pyridin-4-yl]-thiophen-2-yl.

Yet as exemplary R61-substituted Hh1 radicals may be more detailed mentioned, for example, 2'-(R61)-2,4'-bipyridyl-5-yl or 6'-(R61)-2,3'-bipyridyl-5-yl, in which
R61 is -T2-N(R611)R612, in which T2 is a bond, and
R611 and R612 are both hydrogen, or
R611 and R612 together and with inclusion of the nitrogen atom, to which they are bonded, form a morpholino, 4N-methyl-piperazino, piperidino or pyrrolidino radical;

such as e.g. 2'-(4-methyl-piperazin-1-yl)-2,4'-bipyridyl-5-yl.

Specifically, as an exemplary R61-substituted Hh1 radical may be explicitly mentioned, for example, any one selected from 5-[2-(4-methyl-piperazin-1-yl)-pyridin-4-yl]-thiophen-2-yl, 5-(1N-methyl-pyrazol-4-yl)-thiophen-2-yl, 2'-(4-methyl-piperazin-1-yl)-2,4'-bipyridyl-5-yl, 5-(2-methyl-thiazol-4-yl)-thiophen-2-yl, and 6-(1N-methyl-pyrazol-4-yl)-pyridin-3-yl.

More specifically, as an exemplary R61-substituted Hh1 radical may be more explicitly mentioned, for example, 5-[2-(4-methyl-piperazin-1-yl)-pyridin-4-yl]-thiophen-2-yl.

Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group.

Ah1 may include, without being restricted thereto, the phenyl-thiophenyl e.g. 5-phenyl-thiophen-2-yl, or the phenyl-pyridyl e.g. 6-phenyl-pyridin-3-yl, radical.

In a special detail, exemplary Ah1 radicals may include phenyl-thiophenyl, e.g. 5-(phenyl)-thiophen-2-yl.

Yet in a special detail, exemplary Ah1 radicals may include phenyl-pyridinyl, e.g. 6-(phenyl)-pyridin-3-yl.

As non-limiting example of R61-substituted derivatives of Ah1 may be mentioned [(R61)-phenyl]-thiophenyl, such as e.g. the following radicals:

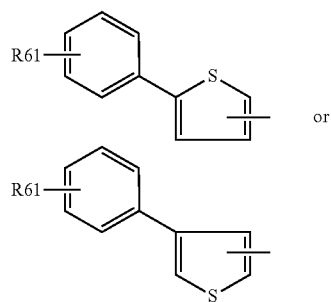

in which the substituent R61 can be attached in the ortho, or, in particular, meta or para position with respect to the binding position in which the phenyl ring is bonded to the thiophenyl radical, such as e.g. [3-(R61)-phenyl]-thiophenyl or [4-(R61)-phenyl]-thiophenyl, like 5-[3-(R61)-phenyl]-thiophen-2-yl or 5-[4-(R61)-phenyl]-thiophen-2-yl.

Yet as non-limiting example of R61-substituted derivatives of Ah1 may be mentioned [(R61)-phenyl]-pyridinyl, such as e.g. the following radicals:

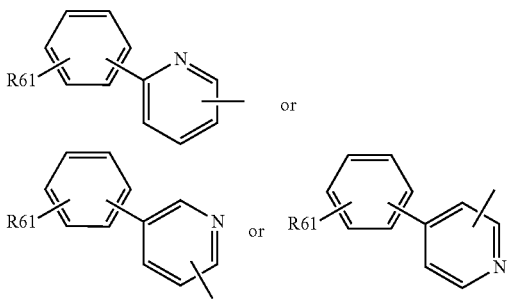

in which the substituent R61 can be attached in the ortho, or, in particular, meta or para position with respect to the binding position in which the phenyl ring is bonded to the pyridinyl radical, such as e.g. [3-(R61)-phenyl]-pyridinyl or [4-(R61)-phenyl]-pyridinyl or 6-[(R61)-phenyl]-pyridin-3-yl, like 6-[3-(R61)-phenyl]-pyridin-3-yl or 6-[4-(R61)-phenyl]-pyridin-3-yl.

As exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is -T2-N(R611)R612, in which T2 is methylene, dimethylene or trimethylene, and
R611 and R612 together and with inclusion of the nitrogen atom, to which they are bonded, form a morpholino or 4N-methyl-piperazino, or a piperidino or pyrrolidino radical;
such as, for example, any selected from 5-[4-(2-morpholin-4-yl-ethyl)-phenyl]-thiophen-2-yl, 5-[4-(morpholin-4-yl-methyl)-phenyl]-thiophen-2-yl and 5-[3-(morpholin-4-yl-methyl)-phenyl]-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]thiophen-2-yl, in which
R61 is -T2-N(R611)R612, in which T2 is methylene, dimethylene or trimethylene, and
R611 and R612 are both methyl;
such as, for example, any selected from 5-(4-dimethylaminomethyl-phenyl)-thiophen-2-yl and 5-(3-dimethylaminomethyl-phenyl)-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is -T2-N(R611)R612, in which T2 is methylene, dimethylene or trimethylene, and
R611 is hydrogen, cyclopropyl, cyclopentyl, 2-methoxyethyl, acetyl or methylsulfonyl,
R612 is hydrogen;
such as, for example, any selected from 5-(3-aminomethyl-phenyl)-thiophen-2-yl, 5-[3-(acetylamino)-methyl-phenyl]-thiophen-2-yl and 5-[3-(methylsulphonylamino)-methyl-phenyl]-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is methylsulphonylamino, N,N-dimethylaminosulphonyl, acetamido, hydroxymethyl, amino, dimethylamino, morpholino, hydroxyl, trifluoromethyl or methoxy;
such as e.g. 5-(4-dimethylsulphamoyl-phenyl)-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is —O-T3-N(R613)R614, in which T3 is dimethylene or trimethylene, and
R613 and R614 together and with inclusion of the nitrogen atom, to which they are bonded, form a morpholino, pyrrolidino or 4N-methyl-piperazino, or a piperidino radical;
such as, for example, any selected from 5-[4-(2-morpholin-4-yl-ethoxy)-phenyl]-thiophen-2-yl, 5-[4-(3-morpholin-4-yl-propoxy)-phenyl]-thiophen-2-yl, 5-{4-[2-(4-methyl-piperazin-1-yl)-ethoxy]-phenyl}-thiophen-2-yl and 5-[4-(2-pyrrolidin-1-yl-ethoxy)-phenyl]-thiophen-2-yl.

Yet as exemplary R61-substituted Ah1 radicals may be more detailed mentioned, for example, 6-[3-(R61)-phenyl]-pyridin-3-yl or 6-[4-(R61)-phenyl]-pyridin-3-yl, in which
R61 is -T2-N(R611)R612, in which T2 is methylene, dimethylene or trimethylene, and
R611 and R612 are both methyl;
such as, for example, any selected from 6-(4-dimethylaminomethyl-phenyl)-pyridin-3-yl and 6-(3-dimethylaminomethyl-phenyl)-pyridin-3-yl.

Yet as exemplary R61-substituted Ah1 radicals may be more detailed mentioned, for example, 6-[3-(R61)-phenyl]-pyridin-3-yl or 6-[4-(R61)-phenyl]-pyridin-3-yl, in which
R61 is —O-T3-N(R613)R614, in which T3 is dimethylene or trimethylene, and
R613 and R614 together and with inclusion of the nitrogen atom, to which they are bonded, form a morpholino, piperidino, pyrrolidino or 4N-methyl-piperazino radical;
such as e.g. 6-[4-(2-pyrrolidin-1-yl-ethoxy)-phenyl]-pyridin-3-yl.

An example of R61-substituted Ah1 radicals may be [4-(R61)-phenyl]-pyridinyl, e.g. 6-[4-(R61)-phenyl]-pyridin-3-yl, in which R61 is any one selected from the group $G_{Ah1}$ consisting of 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methylpiperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl.

Another example of R61-substituted Ah1 radicals may be [3-(R61)-phenyl]-pyridinyl, e.g. 6-[3-(R61)-phenyl]-pyridin-3-yl, in which R61 is any one selected from the group $G_{Ah1}$ given above. A further example of R61-substituted Ah1 radicals may be [4-(R61)-phenyl]-thiophenyl, e.g. 5-[4-(R61)-phenyl]-thiophen-2-yl, in which R61 is any one selected from the group $G_{Ah1}$ given above. Another example of R61-substituted Ah1 radicals may be [3-(R61)-phenyl]

thiophenyl, e.g. 5-[3-(R61)-phenyl]-thiophen-2-yl, in which R61 is any one selected from the group $G_{Ah1}$ given above.

Specifically, as an exemplary R61-substituted Ah1 radical may be explicitly mentioned, for example, any one selected from 5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 5-[4-(2-morpholin-4-yl-ethoxy)-phenyl]-thiophen-2-yl, 5-[4-(3-morpholin-4-yl-propoxy)-phenyl]-thiophen-2-yl, 5-{4-[2-(4-methyl-piperazin-1-yl)-ethoxy]-phenyl}-thiophen-2-yl, 5-[4-(2-pyrrolidin-1-yl-ethoxy)-phenyl]-thiophen-2-yl, 5-(4-dimethylaminomethyl-phenyl)-thiophen-2-yl, 5-(3-dimethylaminomethyl-phenyl)-thiophen-2-yl, 6-(4-dimethylaminomethyl-phenyl)-pyridin-3-yl, 6-(3-dimethylaminomethyl-phenyl)-pyridin-3-yl, and 6-[4-(2-pyrrolidin-1-yl-ethoxy)-phenyl]-pyridin-3-yl, 5-(3-aminomethyl-phenyl)-thiophen-2-yl, 5-[3-(acetylamino)-methyl-phenyl]-thiophen-2-yl, 5-[3-(methylsulphonylamino)-methyl-phenyl]-thiophen-2-yl, and 5-(4-dimethylsulphamoyl-phenyl)-thiophen-2-yl.

More specifically, as an exemplary R61-substituted Ah1 radical may be more explicitly mentioned, for example, 5-(4-dimethylaminomethyl-phenyl)-thiophen-2-yl.

It is to be stated, that each of the radicals Hh1 and Ah1 is bonded via a ring carbon atom to the moiety T1.

Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group.

A particular embodiment of said Ha1 radicals refers to heteroaryl-phenyl radicals, particularly 3-(heteroaryl)-phenyl or 4-(heteroaryl)-phenyl radicals.

Ha1 may include, without being restricted thereto, the furanyl-phenyl, thiophenyl-phenyl, pyrazolyl-phenyl e.g. pyrazol-1-yl-phenyl or pyrazol-4-yl-phenyl, imidazolyl-phenyl e.g. imidazol-1-yl-phenyl, isoxazolyl-phenyl, or pyridinyl-phenyl radicals, or the thiazolyl-phenyl e.g. thiazol-4-yl-phenyl radical.

In a special detail, exemplary Ha1 radicals may include pyrazolyl-phenyl, e.g. 3-(pyrazolyl)-phenyl or 4-(pyrazolyl)-phenyl. Yet in a special detail, exemplary Ha1 radicals may include pyridinyl-phenyl, e.g. 4-(pyridinyl)-phenyl or 3-(pyridinyl)-phenyl. Yet in a special detail, exemplary Ha1 radicals may include isoxazolyl-phenyl, e.g. 4-(isoxazolyl)-phenyl or 3-(isoxazolyl)-phenyl. Yet in a special detail, exemplary Ha1 radicals may include thiazolyl-phenyl, e.g. 4-(thiazolyl)-phenyl or 3-(thiazolyl)-phenyl.

In a further special detail, exemplary Ha1 radicals may include 3-(pyrazol-1-yl)-phenyl, 4-(pyrazol-1-yl)-phenyl, 4-(pyridin-4-yl)-phenyl, 3-(pyridin-4-yl)-phenyl, 4-(pyridin-3-yl)-phenyl, 3-(pyridin-3-yl)-phenyl, 4-(isoxazol-4-yl)-phenyl, 3-(isoxazol-4-yl)-phenyl, 3-(pyrazol-4-yl)-phenyl or 4-(pyrazol-4-yl)-phenyl.

As non-limiting example of R61-substituted derivatives of Ha1 may be mentioned [1N-(1-4C-alkyl)-pyrazolyl]-phenyl, such as e.g. [1N-(1-4C-alkyl)-pyrazol-4-yl]-phenyl, like 3-[1N-(1-2C-alkyl)-pyrazol-4-yl]-phenyl or 4-[1N-(1-2C-alkyl)-pyrazol-4-yl]-phenyl, e.g. 3-(1N-methyl-pyrazol-4-yl)-phenyl or 4-(1N-methyl-pyrazol-4-yl)-phenyl.

As non-limiting example of R61- and/or R62-substituted derivatives of Ha1 may be mentioned (methyl-isoxazolyl)-phenyl or (dimethyl-isoxazolyl)-phenyl, such as e.g. 3-(3,5-dimethyl-isoxazol-4-yl)-phenyl or 4-(3,5-dimethyl-isoxazol-4-yl)-phenyl.

Yet as non-limiting example of R61-substituted derivatives of Ha1 may be mentioned [(R61)-pyridinyl]-phenyl, such as e.g. the following radicals:

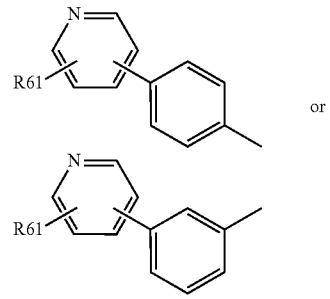

in which the substituent R61 can be attached in the ortho, or, in particular, meta or para position with respect to the binding position in which the pyridinyl ring is bonded to the phenyl radical, such as e.g. 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl.

As exemplary R61-substituted Ha1 radicals may be more detailed mentioned, for example, 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which
R61 is -T2-N(R611)R612, in which T2 is a bond, and
R611 and R612 together and with inclusion of the nitrogen atom, to which they are bonded, form a morpholino or 4N-methyl-piperazino, or a piperidino or pyrrolidino radical;
such as, for example, any selected from 4-[2-(4-methyl-piperazin-1-yl)-pyridin-4-yl]-phenyl and 3-[2-(4-methyl-piperazin-1-yl)-pyridin-4-yl]-phenyl.

Yet as exemplary R61-substituted Ha1 radicals may be more detailed mentioned, for example, 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which
R61 is -T2-N(R611)R612, in which T2 is a bond, and
R611 and R612 are both hydrogen;
such as, for example, any selected from 4-[6-amino-pyridin-3-yl]-phenyl and 3-[6-amino-pyridin-3-yl]-phenyl.

Yet as exemplary R61-substituted Ha1 radicals may be more detailed mentioned, for example, 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which R61 is methoxy; such as, for example, any selected from 4-[6-methoxy-pyridin-3-yl]-phenyl and 3-[6-methoxy-pyridin-3-yl]-phenyl.

Specifically, as an exemplary R61-substituted Ha1 radical may be explicitly mentioned, for example, any one selected from 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, 3-[6-amino-pyridin-3-yl]-phenyl, 4-[6-methoxy-pyridin-3-yl]-phenyl, 3-[6-methoxy-pyridin-3-yl]-phenyl, 3-(1N-methyl-pyrazol-4-yl)-phenyl, 4-(1N-methyl-pyrazol-4-yl)-phenyl, and 4-(3,5-dimethyl-isoxazol-4-yl)-phenyl.

More specifically, as an exemplary R61-substituted Ha1 radical may be more explicitly mentioned, for example, any one selected from 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, and 4-(1N-methyl-pyrazol-4-yl)-phenyl.

As part of the radicals Hh1, Ah1 and Ha1, the mentioned heteroaryl group selected from a group consisting of monocyclic 5- or 6-membered heteroaryl radicals comprising one or two heteroatoms, each of which is selected from the group consisting of nitrogen, oxygen and sulphur, may be chosen, for example, from the group consisting of, the 5-membered heteroaryl radicals, pyrrolyl, furanyl, thiophenyl, oxazolyl, isoxazolyl, thiazolyl, isothiazolyl, imidazolyl and pyrazolyl, and, the 6-membered heteroaryl radicals, pyridinyl, pyrimidinyl, pyrazinyl and pyridazinyl.

Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the to the parent molecular group.

A particular embodiment of said Ha2 radicals refers to heteroaryl-phenyl radicals, particularly 3-(heteroaryl)-phenyl or 4-(heteroaryl)-phenyl radicals.

Another particular embodiment of said Ha2 radicals refers to heteroaryl-phenyl radicals, particularly 3-(heteroaryl)-phenyl or 4-(heteroaryl)-phenyl radicals, in which the heteroaryl moiety contains a benzene ring.

Another particular embodiment of said Ha2 radicals refers to heteroaryl-phenyl radicals, particularly 3-(heteroaryl)-phenyl or 4-(heteroaryl)-phenyl radicals, in which the heteroaryl moiety contains a benzene ring, and whereby the heteroaryl moiety is attached via said benzene ring to the phenyl moiety.

Ha2 may include, without being restricted thereto, the indolyl-phenyl, benzothiophenyl-phenyl, benzofuranyl-phenyl, benzoxazolyl-phenyl, benzothiazolyl-phenyl, indazolyl-phenyl, benzimidazolyl-phenyl, benzisoxazolyl-phenyl, benzisothiazolyl-phenyl, benzofurazanyl-phenyl, benzotriazolyl-phenyl, benzothiadiazolyl-phenyl, quinolinyl-phenyl, isoquinolinyl-phenyl, quinazolinyl-phenyl, quinoxalinyl-phenyl, cinnolinyl-phenyl, indolizinyl-phenyl or naphthyridinyl-phenyl.

In a special detail, exemplary Ha2 radicals may include 3-(indolyl)-phenyl or 4-(indolyl)-phenyl.

In a further special detail, exemplary Ha2 radicals may include 3-(indol-5-yl)-phenyl or 4-(indol-5-yl)-phenyl.

Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, A particular embodiment of said Ha3 radicals refers to heteroaryl-phenyl radicals, particularly 3-(heteroaryl)-phenyl or 4-(heteroaryl)-phenyl radicals.

Ha3 may include, without being restricted thereto, the thiadiazolyl-phenyl (e.g. [1,3,4]thiadiazol-2-yl-phenyl or [1,2,5]thiadiazol-3-yl-phenyl), oxadiazolyl-phenyl (e.g. [1,3,4]oxadiazol-2-yl-phenyl or [1,2,4]oxadiazol-5-yl-phenyl), triazolyl-phenyl (e.g. triazol-1-yl-phenyl or [1,2,3]triazol-4-yl) or tetrazolyl-phenyl (e.g. tetrazol-1-yl-phenyl or tetrazol-5-yl-phenyl) radicals.

In a special detail, exemplary Ha3 radicals may include triazolyl-phenyl, e.g. 3-(triazolyl)-phenyl or 4-(triazolyl)-phenyl. In a further special detail, exemplary Ha3 radicals may include 3-[1,2,3]triazol-4-yl-phenyl or 4-[1,2,3]triazol-4-yl-phenyl.

As non-limiting example of R61-substituted derivatives of Ha3 may be mentioned {1N—(R61)-[1,2,3]triazolyl}-phenyl, such as e.g. {1N—(R61)-[1,2,3]triazol-4-yl}-phenyl, like 3-{1N—(R61)-[1,2,3]triazol-4-yl}-phenyl or 4-{1N—(R61)-[1,2,3]triazol-4-yl}-phenyl.

As exemplary R61-substituted Ha3 radicals may be more detailed mentioned, for example, 3-[1N—(R61)-1,2,3-triazol-4-yl]-phenyl or 4-{1N—(R61)-[1,2,3]triazol-4-yl}-phenyl, in which
  R61 is -T2-N(R611)R612, in which
  T2 is dimethylene or trimethylene, and
  R611 and R612 together and with inclusion of the nitrogen atom, to which they are bonded, form a piperidino, pyrrolidino, morpholino or 4N-methyl-piperazino radical;
such as e.g. 4-{1-(2-morpholin-4-yl-ethyl)-[1,2,3]triazol-4-yl}-phenyl or 4-{1-(2-piperidin-1-yl-ethyl)-[1,2,3]triazol-4-yl}-phenyl.

Ha4 is a heteroarylaryl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha4 is bonded via said aryl moiety to the to the parent molecular group, A particular embodiment of said Ha4 radicals refers to heteroaryl-phenyl radicals, particularly 3-(heteroaryl)-phenyl or 4-(heteroaryl)-phenyl radicals.

Another particular embodiment of said Ha4 radicals refers to heteroaryl-phenyl radicals, particularly 3-(heteroaryl)-phenyl or 4-(heteroaryl)-phenyl radicals, whereby the heteroaryl moiety is attached via its benzene ring to the phenyl moiety.

Ha4 may include, without being restricted thereto, the indolinyl-phenyl, isoindolinyl-phenyl, (1,2,3,4-tetrahydroquinolinyl)-phenyl or (1,2,3,4-tetrahydroisoquinolinyl)-phenyl, (2,3-dihydrobenzofuranyl)-phenyl, (2,3-dihydrobenzothiophenyl)-phenyl, (benzo[1,3]dioxolyl)-phenyl, (2,3-dihydrobenzo[1,4]dioxinyl)-phenyl, chromanyl-phenyl, chromenyl-phenyl or (2,3-dihydrobenzo[1,4]oxazinyl)-phenyl.

In a special detail, exemplary Ha4 radicals may include (benzo[1,3]dioxolyl)-phenyl, e.g. 3-(benzo[1,3]dioxolyl)-phenyl or 4-(benzo[1,3]dioxolyl)-phenyl, such as, for example, (benzo[1,3]dioxol-5-yl)-phenyl, e.g. 3-(benzo[1,3]dioxol-5-yl)-phenyl or 4-(benzo[1,3]dioxol-5-yl)-phenyl. Yet in a special detail, exemplary Ha4 radicals may include (2,3-dihydrobenzofuranyl)-phenyl, e.g. 3-(2,3-dihydrobenzofuranyl)-phenyl or 4-(2,3-dihydrobenzofuranyl)-phenyl, such as, for example, (2,3-dihydrobenzofuran-5-yl)-phenyl or 2,3-dihydrobenzofuran-6-yl)-phenyl, e.g. 3-(2,3-dihydrobenzofuran-5-yl)-phenyl or 4-(2,3-dihydrobenzofuran-5-yl)-phenyl. In a further special detail, exemplary Ha4 radicals may include 4-(2,3-dihydrobenzofuran-5-yl)-phenyl.

Har2 stands for a monocyclic 5- or 6-membered unsaturated heteroaromatic ring comprising one to three heteroatoms, each of which is selected from the group consisting of nitrogen, oxygen and sulfur.

Har2 may include, without being restricted thereto, thiophene, oxazole, isoxazole, thiazole, isothiazole, imidazole, pyrazole, triazole, thiadiazole, oxadiazole, pyridine, pyrimidine, pyrazine or pyridazine.

In a special detail, an exemplary Har2 radical may be pyridine.

Cyc1 stands for a ring system of formula la, which is bonded to the nitrogen atom of the carboxamide group via the moiety A. Cyc1 may include, without being restricted thereto, 2-aminophenyl substituted by R71 and/or R72. In a special detail, an exemplary Cyc1 radical may be 2-aminophenyl.

Naphthyl, alone or as part of another group, includes naphthalen-1-yl and naphthalen-2-yl.

In the meaning of the present invention, it is to be understood, that, when two structural portions of the compounds according to this invention are linked via a constituent which has the meaning "bond", then said two portions are directly attached to another via a single bond.

When R61 has the meaning of —U-T3-N(R613)R614, in which U stands for —C(O)NH—, then R61 is the radical —C(O)NH-T3-N(R613)R614.

As it is known for the skilled person, the expressions morpholino, 4N-(1-4C-alkyl)-piperazino, pyrrolidino and the like stand for morpholin-4-yl, 4N-(1-4C-alkyl)-piperazin-1-yl, pyrrolidin-1-yl and the like, respectively.

In general, unless otherwise mentioned the heterocyclic groups mentioned herein refer to all of the possible isomeric forms thereof. The heterocyclic groups mentioned herein refer, unless otherwise noted, in particular to all of the possible positional isomers thereof. Thus, for example, the term pyridyl or pyridinyl, alone or as part of another group, includes pyridin-2-yl, pyridin-3-yl and pyridin-4-yl.

Constituents which are optionally substituted as stated herein, may be substituted, unless otherwise noted, at any possible position.

The carbocyclic groups, alone or as part of other groups, mentioned herein may be substituted by their given substituents or parent molecular groups, unless otherwise noted, at any substitutable ring carbon atom.

The heterocyclic groups, alone or as part of other groups, mentioned herein may be substituted by their given substituents or parent molecular groups, unless otherwise noted, at any possible position, such as e.g. at any substitutable ring carbon or ring nitrogen atom.

Rings containing quaternizable imino-type ring nitrogen atoms (—N═) may be particularly not quaternized on these imino-type ring nitrogen atoms by the mentioned substituents or parent molecular groups.

Any heteroatom of a heterocyclic ring with unsatisfied valences mentioned herein is assumed to have the hydrogen atom(s) to satisfy the valences.

When any variable occurs more than one time in any constituent, each definition is independent.

According to expert's knowledge the compounds of formula I of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

The substituents R61 and R62 of compounds of formula I can be attached in any possible position of the Aa1, Hh1, Ha1, Ha2, Ha3, Ha4 or Ah1 radical, whereby emphasis is given to the attachment at the terminal ring;

in another embodiment, Q1 is monosubstituted by R61, and is Aa1, Hh1, Ha1 or Ah1, whereby emphasis is given to the attachment of R61 at the terminal ring;

in yet another embodiment, R6 is Aa1, Ha1 or Ha2, each of which is monosubstituted by R61, whereby emphasis is given to the attachment of R61 at the terminal ring;

in yet another embodiment, R6 is Aa1, Hh1, Ha1, Ha2 or Ah1, each of which is monosubstituted by R61, whereby emphasis is given to the attachment of R61 at the terminal ring;

in yet another embodiment, R6 is Aa1, Hh1, Ha1, Ha2, Ha3 or Ah1, each of which is monosubstituted by R61, whereby emphasis is given to the attachment of R61 at the terminal ring;

in yet another embodiment, R6 is Ha2, Ha3 or Ha4, each of which is unsubstituted.

Within the meaning of this invention, the terminal ring of Aa1, Hh1, Ha1, Ha2, Ha3, Ha4 or Ah1 refers to those ring portion of these radicals which is not directly attached to the T1 moiety.

The person skilled in the art is aware on account of his/her expert knowledge that certain combinations of the variable characteristics mentioned in the description of this invention may lead to chemically less stable compounds. This can apply, for example, to certain compounds, in which—in a manner being disadvantageous for chemical stability—two heteroatoms (S, N or O) would directly meet or would only be separated by one carbon atom. Particularly, the compounds according to this invention are those, in which the combination of the abovementioned variable substituents does not lead to chemically less stable compounds.

Compounds according to aspect A of the present invention more worthy to be mentioned are those compounds of formula I in which R1, R2, R3, R4 and R5 are independently hydrogen or 1-4C-alkyl, R6 is -T1-Q1, in which T1 is a bond, either Q1 is substituted by R61 and/or R62, and is Aa1, Hh1, Ha1, Ha2, Ha3, Ha4 or Ah1, Or Q1 is unsubstituted, and is Ha2, Ha3 or Ha4, in which R61 is 1-4C-alkyl, 1-4C-alkoxy, hydroxyl, trifluoromethyl, halogen, hydroxy-1-4C-alkyl, 1-4C-alkylsulphonylamino, tolylsulphonylamino, phenylsulphonylamino, 1-4C-alkylcarbonylamino, di-1-4C-alkylaminosulphonyl, -T2-N(R611)R612, —U-T3-N(R613)R614, -T4-Het3, or —V-T5-Het4, in which T2 is a bond or 1-4C-alkylene, R611 is hydrogen, 1-4C-alkyl, 3-7C-cycloalkyl, 1-4C-alkoxy-2-4C-alkyl, 1-4C-alkylcarbonyl, or 1-4C-alkylsulphonyl, R612 is hydrogen or 1-4C-alkyl, or R611 and R612 together and with inclusion of the nitrogen atom, to which they are bonded, form a heterocyclic ring Het1, in which Het1 is morpholino, piperidino, pyrrolidino, piperazino or 4N-(1-4C-alkyl)-piperazino, U is —O— (oxygen) or —C(O)NH—, T3 is 2-4C-alkylene, R613 is hydrogen, 1-4C-alkyl, 3-7C-cycloalkyl, 1-4C-alkoxy-2-4C-alkyl, 1-4C-alkylcarbonyl, or 1-4C-alkylsulphonyl, R614 is hydrogen or 1-4C-alkyl, or R613 and R614 together and with inclusion of the nitrogen atom, to which they are bonded, form a heterocyclic ring Het2, in which Het2 is morpholino, piperidino, pyrrolidino, piperazino or 4N-(1-4C-alkyl)-piperazino, T4 is a bond or 1-4C-alkylene, Het3 is 1N-(1-4C-alkyl)-piperidinyl or 1N-(1-4C-alkyl)-pyrrolidinyl, V is —O— (oxygen) or —C(O)NH—, T5 is a bond, or 1-4C-alkylene, Het4 is 1N-(1-4C-alkyl)-piperidinyl or 1N-(1-4C-alkyl)-pyrrolidinyl, R62 is 1-4C-alkyl, Aa1 is biphenyl, Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group, Ha1 is a heteroaryl-phenyl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group, Ha4 is a heteroaryl-phenyl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and a phenyl group, whereby said heteroaryl and phenyl groups are linked together via a single bond, and whereby Ha4 is bonded via said phenyl moiety to the to the parent molecular group, R7 is hydroxyl, or 2-aminophenyl, and the salts of these compounds.

Compounds according to aspect A of the present invention in particular worthy to be mentioned are those compounds of formula I in which R1, R2, R3, R4 and R5 are hydrogen, R6 is -T1-Q1, in which T1 is a bond, either Q1 is substituted by R61 and/or R62 on the terminal ring, and is Aa1, Hh1, Ha1, Ha2, Ha3, Ha4 or Ah1, Or Q1 is unsubstituted, and is Ha2, Ha3 or Ha4, in which R61 is 1-2C-alkyl, 1-2C-alkoxy, hydroxyl, trifluoromethyl, halogen, hydroxy-1-2C-alkyl, 1-2C-alkylsulphonylamino, 1-2C-alkylcarbonylamino, di-1-2C-alkylaminosulphonyl, -T2-N(R611)R612, —U-T3-N(R613)R614, -T4-Het3, or —V-T5-Het4, in which T2 is a bond or straight chain 1-4C-alkylene, R611 is hydrogen, 1-2C-alkyl, 3-5C-cycloalkyl, 1-2C-alkoxy-2-3C-alkyl, 1-2C-alkylcarbonyl, or 1-2C-alkylsulphonyl, R612 is hydrogen or 1-2C-alkyl, or R611 and R612 together and with inclusion of the nitrogen atom, to which they are bonded, form a heterocyclic ring Het1, in which Het1 is morpholino, piperidino, pyrrolidino, piperazino or 4N-(1-2C-alkyl)-piperazino, U is —O— (oxygen) or —C(O)NH—, T3 is straight chain 2-4C-alkylene, R613 is hydrogen, 1-2C-alkyl, 3-5C-cycloalkyl, 1-2C-alkoxy-2-3C-alkyl, 1-2C-alkylcarbonyl, or 1-2C-alkylsulphonyl, R614 is hydrogen or 1-2C-alkyl, or R613 and R614 together and with inclusion of the nitrogen atom, to which they are bonded, form a heterocyclic ring Het2, in which Het2 is morpholino, piperidino, pyrrolidino, piperazino or 4N-(1-2C-alkyl)-piperazino, T4 is a bond or straight chain 1-4C-alkylene, Het3 is 1N-(1-2C-alkyl)-piperidinyl or 1N-(1-2C-alkyl)-pyrrolidinyl, V is —O— (oxygen) or —C(O)NH—, T5 is a bond or straight chain 1-4C-alkylene, Het4 is 1N-(1-2C-alkyl)-piperidinyl or 1N-(1-2C-alkyl)-pyrrolidinyl, R62 is 1-2C-alkyl, Aa1 is 1,1'-biphenyl-3-yl or 1,1'-biphenyl-4-yl, Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group, Ha1 is a 3-(heteroaryl)-phenyl or 4-(heteroaryl)-phenyl radical each made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a 3-(heteroaryl)-phenyl or 4-(heteroaryl)-phenyl radical each made up of a heteroaryl group selected from a group consisting of fused bicyclic 9- or 10-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, Ha3 is a 3-(heteroaryl)-phenyl or 4-(heteroaryl)-phenyl radical each made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group, Ha4 is a 3-(heteroaryl)-phenyl or 4-(heteroaryl)-phenyl radical each made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and a phenyl group, whereby said heteroaryl and phenyl groups are linked together via a single bond, and whereby Ha4 is bonded via said phenyl moiety to the to the parent molecular group, R7 is hydroxyl, or 2-aminophenyl, and the salts of these compounds.

Compounds according to aspect A of the present invention in more particular worthy to be mentioned are those compounds of formula I in which R1, R2, R3, R4 and R5 are hydrogen, R6 is -T1-Q1, in which T1 is a bond, either Q1 is substituted by R61 and/or R62 on the terminal ring, and is Aa1, Hh1, Ha1, Ha2, Ha3, Ha4 or Ah1, or Q1 is unsubstituted, and is Ha2, Ha3 or Ha4, in which R61 is methyl, methoxy, hydroxyl, trifluoromethyl, hydroxymethyl, methylsulphonylamino, methylcarbonylamino, dimethylaminosulphonyl, -T2-N(R611)R612, —U-T3-N(R613)R614, -T4-Het3, or —V-T5-Het4, in which T2 is a bond, methylene, dimethylene or trimethylene, R611 is hydrogen, methyl, cyclopropyl, cyclopentyl, 2-methoxyethyl, acetyl or methylsulphonyl, R612 is hydrogen or methyl, or R611 and R612 together and with inclusion of the nitrogen atom, to which they are bonded, form a heterocyclic ring Het1, in which Het1 is morpholino, piperidino, pyrrolidino, piperazino or 4-methyl-piperazino, U is —O— (oxygen) or —C(O)NH—, T3 is dimethylene or trimethylene, R613 is hydrogen, methyl, cyclopropyl, cyclopentyl, 2-methoxyethyl, acetyl or methylsulphonyl, R614 is hydrogen or methyl, or R613 and R614 together and with inclusion of the nitrogen atom, to which they are bonded, form a heterocyclic ring Het2, in which Het2 is morpholino, piperidino, pyrrolidino, piperazino or 4-methyl-piperazino, T4 is a bond, methylene, dimethylene or trimethylene, Het3 is 1-methyl-piperidinyl or 1-methyl-pyrrolidinyl, V is —O— (oxygen) or —C(O)NH—, T5 is a bond, methylene, dimethylene or trimethylene, Het4 is 1-methyl-piperidinyl or 1-methyl-pyrrolidinyl, R62 is methyl, Aa1 is 1,1'-biphenyl-3-yl, or 1,1'-biphenyl-4-yl, Hh1 is a bisheteroaryl radical made up of two heteroaryl groups, which are selected independently from a group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, and which are linked together via a single bond, such as, for example, Hh1 is pyridinyl-thiophenyl, thiazolyl-thiophenyl, pyrazolyl-thiophenyl, bipyridyl, pyrazolyl-pyridinyl, or thiazolyl-pyridinyl, Ah1 is a phenyl-heteroaryl radical made up of an phenyl group and a heteroaryl group selected from a group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, whereby said phenyl and heteroaryl groups are linked together via a single bond, and whereby Ah1 is bonded via said heteroaryl moiety to the parent molecular group, such as, for example, Ah1 is phenyl-thiophenyl, or phenyl-pyridinyl, Ha1 is a 3-(heteroaryl)-phenyl or 4-(heteroaryl)-phenyl radical each made up of a heteroaryl group selected from a group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, and a phenyl group, whereby said heteroaryl and phenyl groups are linked together via a single bond, and whereby Ha1 is bonded via said phenyl moiety to the to the parent molecular group, such as, for example, Ha1 is 3-(pyridinyl)-phenyl, 3-(thiazolyl)-phenyl, 3-(pyrazolyl)-phenyl, 3-(isoxazolyl)-phenyl, 4-(pyridinyl)-phenyl, 4-(thiazolyl)-phenyl, 4-(pyrazolyl)-phenyl, or 4-(isoxazolyl)-phenyl, Ha2 is a 3-(heteroaryl)-phenyl or 4-(heteroaryl)-phenyl radical each made up of a heteroaryl group selected from a group consisting of indolyl, benzothiophenyl, benzofuranyl, benzoxazolyl, benzothiazolyl, indazolyl, benzimidazolyl, benzisoxazolyl, benzisothiazolyl, benzofurazanyl, benzotriazolyl, benzothiadiazolyl, quinolinyl, isoquinolinyl, quinazolinyl, quinoxalinyl, cinnolinyl, indolizinyl and naphthyridinyl, and a phenyl group, whereby said heteroaryl and phenyl groups are linked together via a single bond, and whereby Ha2 is bonded via said phenyl moiety to the to the parent molecular group, such as, for example, Ha2 is 3-(indolyl)-phenyl, or 4-(indolyl)-phenyl, Ha1 is a 3-(heteroaryl)-phenyl or 4-(heteroaryl)-phenyl radical each made up of a heteroaryl group selected from a group consisting of thiadiazolyl, oxadiazolyl, triazolyl and tetrazolyl, and a phenyl group, whereby said heteroaryl and phenyl groups are linked together via a single bond, and whereby Ha3 is bonded via said phenyl moiety to the to the parent molecular group, such as, for example, Ha3 is 3-(triazolyl)-phenyl, or 4-(triazolyl)-phenyl, Ha4 is a 3-(heteroaryl)-phenyl or 4-(heteroaryl)-phenyl radical each made up of a heteroaryl group selected from a group consisting of indolinyl, isoindolinyl, 1,2,3,4-tetrahydroquinolinyl, 1,2,3,4-tetrahydroisoquinolinyl, 2,3-dihydrobenzofuranyl, 2,3-dihydrobenzothiophenyl, benzo[1,3]dioxolyl, 2,3-dihydrobenzo[1,4]dioxinyl, chromanyl, chromenyl and 2,3-dihydrobenzo[1,4]oxazinyl, and a phenyl group, whereby said heteroaryl and phenyl groups are linked together via a single bond, and whereby Ha3 is bonded via said phenyl moiety to the to the parent molecular group, such as, for example, Ha4 is 3-(benzo[1,3]dioxolyl)-phenyl, 4-(benzo[1,3]dioxolyl)-phenyl, 3-(2,3-dihydrobenzofuranyl)-phenyl, or 4-(2,3-dihydrobenzofuranyl)-phenyl, R7 is hydroxyl, or 2-aminophenyl, and the salts of these compounds.

Compounds according to aspect A of the present invention to be emphasized are those compounds of formula I in which R1, R2, R3, R4 and R5 are hydrogen, R6 is -T1-Q1, in which T1 is a bond;

either

Q1 is substituted by R61 on the terminal ring, and is Aa1 or Ah1, in which

Aa1 is 1,1'-biphenyl-3-yl, or 1,1'-biphenyl-4-yl, such as, for example,

3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl, Ah1 is phenyl-thiophenyl, or phenyl-pyridinyl, such as, for example,

[3-(R61)-phenyl]-thiophenyl, [4-(R61)-phenyl]thiophenyl, [3-(R61)-phenyl]pyridinyl or [4-(R61)-phenyl]pyridinyl, e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which R61 is methoxy, hydroxyl, trifluoromethyl, hydroxymethyl, methylsulphonylamino, methylcarbonylamino, dimethylaminosulphonyl, -T2-N(R611)R612, —U-T3-N(R613)R614, -T4-Het3, or —V-T5-Het4, in which T2 is a bond, methylene, dimethylene or trimethylene, R611 is hydrogen, methyl, cyclopropyl, cyclopentyl, 2-methoxyethyl, acetyl or methylsulphonyl, R612 is hydrogen or methyl, or R611 and R612 together and with inclusion of the nitrogen atom, to which they are bonded, form a heterocyclic ring Het1, in which Het1 is morpholino, piperidino, pyrrolidino or 4-methyl-piperazino, U is —O— (oxygen) or —C(O)NH—, T3 is dimethylene or trimethylene, R613 and R614 are methyl, or R613 and R614 together and with inclusion of the nitrogen atom, to which they are bonded, form a heterocyclic ring Het2, in which Het2 is morpholino, piperidino, pyrrolidino or 4-methyl-piperazino, T4 is a bond, methylene, dimethylene or trimethylene, Het3 is 1-methyl-piperidinyl or 1-methyl-pyrrolidinyl, V is —O— (oxygen) or —C(O)NH—, T5 is a bond, methylene, dimethylene or trimethylene, Het4 is 1-methyl-piperidinyl or 1-methyl-pyrrolidinyl;

or

Q1 is substituted by R61 on the terminal ring, and is Hh1 or Ha1, in which

Hh1 is pyridinyl-thiophenyl, or bipyridyl, such as, for example,

[2-(R61)-pyridin-4-yl]thiophenyl or [6-(R61)-pyridin-3-yl]thiophenyl, e.g. 5-[2-(R61)-pyridin-4-yl]-thiophen-2-yl or 5-[6-(R61)-pyridin-3-yl]-thiophen-2-yl, or

[2-(R61)-pyridin-4-yl]-pyridinyl or [6-(R61)-pyridin-3-yl]-pyridinyl, e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl, Ha1 is 3-(pyridinyl)-phenyl, or 4-(pyridinyl)-phenyl, such as, for example, 3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl, in which R61 is methoxy, or -T2-N(R611)R612, in which T2 is a bond, R611 and R612 are independently hydrogen or methyl, or R611 and R612 together and with inclusion of the nitrogen atom, to which they are bonded, form a heterocyclic ring Het1, in which Het1 is morpholino, piperidino, pyrrolidino or 4N-methyl-piperazino;

or

Q1 is 3-(1-methyl-pyrazolyl)-phenyl, 4-(1-methyl-pyrazolyl)-phenyl, 3-(methyl-thiazolyl)-phenyl, 4-(methyl-thiazolyl)-phenyl, 3-(dimethyl-isoxazolyl)-phenyl, 4-(dimethyl-isoxazolyl)-phenyl, (1-methyl-pyrazolyl)-thiophenyl, (1-methyl-pyrazolyl)-pyridinyl, (methyl-thiazolyl)-thiophenyl, (methyl-thiazolyl)-pyridinyl, 3-(benzo[1,3]dioxolyl)-phenyl, 4-(benzo[1,3]dioxolyl)-phenyl, 3-(2,3-dihydrobenzofuranyl)-phenyl, 4-(2,3-dihydrobenzofuranyl)-phenyl, 3-(1-methyl-indolyl)-phenyl, or 4-(1-methyl-indolyl)-phenyl, such as, for example, 3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazol-4-yl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl or 4-(1-methyl-indol-5-yl)-phenyl;

or

Q1 is 3-[1N—(R61)-pyrazolyl]-phenyl, 4-[1N—(R61)-pyrazolyl]-phenyl, [1N—(R61)-pyrazolyl]-thiophenyl, [1N—(R61)-pyrazolyl)-pyridinyl, 3-[1N—(R61)-triazolyl]-phenyl, or 4-[1N—(R61)-triazolyl]-phenyl, such as, for example, 3-[1N—(R61)-pyrazol-4-yl]-phenyl, 4-[1N—(R61)-pyrazol-4-yl]-phenyl, [1N—(R61)-pyrazol-4-yl)-thiophenyl e.g. 5-[1N—(R61)-pyrazol-4-yl]-thiophen-2-yl, [1N—(R61)-pyrazol-4-yl)-pyridinyl e.g. 2-[1N—(R61)-pyrazol-4-yl)-pyridin-4-yl or 6-[1N—(R61)-pyrazol-4-yl)-pyridin-3-yl, 3-[1N—(R61)-triazol-4-yl]-phenyl or 4-[1N—(R61)-triazol-4-yl]-phenyl,
in which
R61 is -T2-N(R611)R612, or -T4-Het3, in which
T2 is dimethylene or trimethylene,
R611 is hydrogen, methyl, cyclopropyl, cyclopentyl, 2-methoxyethyl, acetyl or methylsulphonyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino or 4-methyl-piperazino,
T4 is a bond, methylene, dimethylene or trimethylene,
Het3 is 1-methyl-piperidinyl or 1-methyl-pyrrolidinyl;
R7 is hydroxyl;
and the salts of these compounds.

Other compounds according to aspect A of the present invention to be emphasized are those compounds of formula I in which
R1, R2, R3, R4 and R5 are hydrogen,
R6 is -T1-Q1, in which
T1 is a bond;
either
Q1 is substituted by R61 on the terminal ring, and is Aa1 or Ah1, in which
Aa1 is 1,1'-biphenyl-3-yl, or 1,1'-biphenyl-4-yl,
such as, for example,
3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl,
Ah1 is phenyl-thiophenyl, or phenyl-pyridinyl,
such as, for example,
[3-(R61)-phenyl]-thiophenyl, [4-(R61)-phenyl]thiophenyl, [3-(R61)-phenyl]pyridinyl or [4-(R61)-phenyl]-pyridinyl,
e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl,
in which
R61 is methoxy, hydroxyl, trifluoromethyl, hydroxymethyl, methylsulphonylamino, methylcarbonylamino, dimethylaminosulphonyl, -T2-N(R611)R612, —U-T3-N(R613)R614, -T4-Het3, or —V-T5-Het4, in which
T2 is a bond, methylene, dimethylene or trimethylene,
R611 is hydrogen, methyl, cyclopropyl, cyclopentyl, 2-methoxyethyl, acetyl or methylsulphonyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino or 4-methyl-piperazino,
U is —O— (oxygen) or —C(O)NH—,
T3 is dimethylene or trimethylene,
R613 is methyl,
R614 is methyl,
or R613 and R614 together and with inclusion of the nitrogen atom, to which they are bonded, form a heterocyclic ring Het2, in which
Het2 is morpholino, piperidino, pyrrolidino or 4-methyl-piperazino,
T4 is a bond, methylene, dimethylene or trimethylene,
Het3 is 1-methyl-piperidinyl or 1-methyl-pyrrolidinyl,
V is —O— (oxygen) or —C(O)NH—,
T5 is a bond, methylene, dimethylene or trimethylene,
Het4 is 1-methyl-piperidinyl or 1-methyl-pyrrolidinyl;
or
Q1 is substituted by R61 on the terminal ring, and is Hh1 or Ha1, in which
Hh1 is pyridinyl-thiophenyl, or bipyridyl,
such as, for example,
[2-(R61)-pyridin-4-yl]thiophenyl or [6-(R61)-pyridin-3-yl]thiophenyl,
e.g. 5-[2-(R61)-pyridin-4-yl]-thiophen-2-yl or 5-[6-(R61)-pyridin-3-yl]-thiophen-2-yl, or
[2-(R61)-pyridin-4-yl]-pyridinyl or [6-(R61)-pyridin-3-yl]-pyridinyl,
e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl,
Ha1 is 3-(pyridinyl)-phenyl, or 4-(pyridinyl)-phenyl,
such as, for example,
3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl,
in which
R61 is methoxy, or -T2-N(R611)R612, in which
T2 is a bond,
R611 is hydrogen or methyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino or 4N-methyl-piperazino;
or
Q1 is 3-(1-methyl-pyrazolyl)-phenyl, 4-(1-methyl-pyrazolyl)-phenyl, 3-(methyl-thiazolyl)-phenyl, 4-(methyl-thiazolyl)-phenyl, 3-(dimethyl-isoxazolyl)-phenyl, 4-(dimethyl-isoxazolyl)-phenyl,
(1-methyl-pyrazolyl)-thiophenyl, (1-methyl-pyrazolyl)-pyridinyl, (methyl-thiazolyl)-thiophenyl,
(methyl-thiazolyl)-pyridinyl, 3-(benzo[1,3]dioxolyl)-phenyl, 4-(benzo[1,3]dioxolyl)-phenyl, 3-(2,3-dihydrobenzofuranyl)-phenyl, 4-(2,3-dihydrobenzofuranyl)-phenyl, 3-(1-methyl-indolyl)-phenyl, or 4-(1-methyl-indolyl)-phenyl,
such as, for example,
3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazol-4-yl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl or 4-(1-methyl-indol-5-yl)-phenyl;
or
Q1 is 3-[1N—(R61)-pyrazolyl]-phenyl, 4-[1N—(R61)-pyrazolyl]-phenyl, [1N—(R61)-pyrazolyl)-thiophenyl, [1N—(R61)-pyrazolyl)-pyridinyl, 3-[1N—(R61)-triazolyl]-phenyl, or 4-[1N—(R61)-triazolyl]-phenyl,
such as, for example,
3-[1N—(R61)-pyrazol-4-yl]-phenyl, 4-[1N—(R61)-pyrazol-4-yl]-phenyl, [1N—(R61)-pyrazol-4-yl)-thiophenyl e.g. 5-[1N—(R61)-pyrazol-4-yl)-thiophen-2-yl, [1N—

(R61)-pyrazol-4-yl)-pyridinyl e.g. 2-[1N—(R61)-pyrazol-4-yl)-pyridin-4-yl or 6-[1N—(R61)-pyrazol-4-yl)-pyridin-3-yl,
3-[1N—(R61)-triazol-4-yl]-phenyl or 4-[1N—(R61)-triazol-4-yl]-phenyl,
in which
R61 is -T2-N(R611)R612, or -T4-Het3, in which
T2 is dimethylene or trimethylene,
R611 is hydrogen, methyl, cyclopropyl, cyclopentyl, 2-methoxyethyl, acetyl or methylsulphonyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino or 4-methyl-piperazino,
T4 is a bond, methylene, dimethylene or trimethylene,
Het3 is 1-methyl-piperidinyl or 1-methyl-pyrrolidinyl;
R7 is 2-aminophenyl;
and the salts of these compounds.

Compounds according to aspect A of the present invention to be more emphasized are those compounds of formula I in which
R1, R2, R3, R4 and R5 are hydrogen,
R6 is -T1-Q1, in which T1 is a bond;
either
Q1 is substituted by R61 on the terminal ring, and is Aa1 or Ah1, in which
Aa1 is 1,1'-biphenyl-3-yl, or 1,1'-biphenyl-4-yl,
such as, for example,
3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl,
Ah1 is phenyl-thiophenyl, or phenyl-pyridinyl,
such as, for example,
[3-(R61)-phenyl]-thiophenyl, [4-(R61)-phenyl]thiophenyl, [3-(R61)-phenyl]pyridinyl or [4-(R61)-phenyl]pyridinyl,
e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl,
in which
R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylaminoethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl;
or
Q1 is substituted by R61 on the terminal ring, and is Hh1 or Ha1, in which
Hh1 is pyridinyl-thiophenyl, or bipyridyl, such as, for example,
[2-(R61)-pyridin-4-yl]thiophenyl or [6-(R61)-pyridin-3-yl] thiophenyl,
e.g. 5-[2-(R61)-pyridin-4-yl]-thiophen-2-yl or 5-[6-(R61)-pyridin-3-yl]-thiophen-2-yl, or
[2-(R61)-pyridin-4-yl]-pyridinyl or [6-(R61)-pyridin-3-yl]-pyridinyl,
e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl,
Ha1 is 3-(pyridinyl)-phenyl, or 4-(pyridinyl)-phenyl,
such as, for example,
3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl,
in which
R61 is any one selected from methylsulphonylamino, acetamido, amino, dimethylamino, morpholino, piperidino, pyrrolidino, 4-methyl-piperazino, hydroxy, trifluoromethyl and methoxy;
or
Q1 is 3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazol-4-yl)-pyridin-4-yl, 3-(benzo[1,3] dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl, or 4-(1-methyl-indol-5-yl)-phenyl;
or
Q1 is 3-[1N—(R61)-pyrazol-4-yl]-phenyl, 4-[1N—(R61)-pyrazol-4-yl]-phenyl, [1N—(R61)-pyrazol-4-yl]-thiophenyl e.g. 5-[1N—(R61)-pyrazol-4-yl]-thiophen-2-yl, [1N—(R61)-pyrazol-4-yl)-pyridinyl e.g. 2-[1N—(R61)-pyrazol-4-yl)-pyridin-4-yl or 6-[1N—(R61)-pyrazol-4-yl)-pyridin-3-yl,
3-[1N—(R61)-triazol-4-yl]-phenyl, or 4-[1N—(R61)-triazol-4-yl]-phenyl,
in which
R61 is any one selected from 3-morpholin-4-yl-propyl, 2-morpholin-4-yl-ethyl, 3-(4-methyl-piperazin-1-yl)-propyl, 2-(4-methyl-piperazin-1-yl)-ethyl, 3-pyrrolidin-1-yl-propyl, 2-pyrrolidin-1-yl-ethyl, 3-piperidin-1-yl-propyl, 2-piperidin-1-yl-ethyl, 2-dimethylamino-ethyl and 3-dimethylamino-propyl;
R7 is hydroxyl;
and the salts of these compounds.

Compounds according to aspect A of the present invention to be more emphasized are those compounds of formula I in which
R1, R2, R3, R4 and R5 are hydrogen,
R6 is -T1-Q1, in which T1 is a bond;
either
Q1 is substituted by R61 on the terminal ring, and is Aa1 or Ah1, in which
Aa1 is 1,1'-biphenyl-3-yl, or 1,1'-biphenyl-4-yl,
such as, for example,
3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl, Ah1 is phenyl-thiophenyl, or phenyl-pyridinyl,
such as, for example,
[3-(R61)-phenyl]-thiophenyl, [4-(R61)-phenyl]thiophenyl, [3-(R61)-phenyl]-pyridinyl or [4-(R61)-phenyl]pyridinyl,
e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl,
in which
R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl;
or
Q1 is substituted by R61 on the terminal ring, and is Hh1 or Ha1, in which
Hh1 is pyridinyl-thiophenyl, or bipyridyl,
such as, for example,
[2-(R61)-pyridin-4-yl]thiophenyl or [6-(R61)-pyridin-3-yl]thiophenyl,
e.g. 5-[2-(R61)-pyridin-4-yl]-thiophen-2-yl or 5-[6-(R61)-pyridin-3-yl]-thiophen-2-yl, or
[2-(R61)-pyridin-4-yl]-pyridinyl or [6-(R61)-pyridin-3-yl]-pyridinyl,
e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl,
Ha1 is 3-(pyridinyl)-phenyl, or 4-(pyridinyl)-phenyl,
such as, for example,
3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl,
in which
R61 is any one selected from methylsulphonylamino, acetamido, amino, dimethylamino, morpholino, piperidino, pyrrolidino, 4-methyl-piperazino, hydroxy, trifluoromethyl and methoxy;
or
Q1 is 3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazol-4-yl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl, or 4-(1-methyl-indol-5-yl)-phenyl;
or
Q1 is 3-[1N—(R61)-pyrazol-4-yl]-phenyl, 4-[1N—(R61)-pyrazol-4-yl]-phenyl, [1N—(R61)-pyrazol-4-yl]-thiophenyl e.g. 5-[1N—(R61)-pyrazol-4-yl]-thiophen-2-yl, [1N—(R61)-pyrazol-4-yl)-pyridinyl e.g. 2-[1N—(R61)-pyrazol-4-yl]-pyridin-4-yl or 6-[1N—(R61)-pyrazol-4-yl]-pyridin-3-yl, 3-[1N—(R61)-triazol-4-yl]-phenyl, or 4-[1N—(R61)-triazol-4-yl]-phenyl,
in which
R61 is any one selected from 3-morpholin-4-yl-propyl, 2-morpholin-4-yl-ethyl, 3-(4-methyl-piperazin-1-yl)-propyl, 2-(4-methyl-piperazin-1-yl)-ethyl, 3-pyrrolidin-1-yl-propyl, 2-pyrrolidin-1-yl-ethyl, 3-piperidin-1-yl-propyl, 2-piperidin-1-yl-ethyl, 2-dimethylamino-ethyl and 3-dimethylamino-propyl;
R7 is 2-aminophenyl;
and the salts of these compounds.

Compounds according to aspect A of the present invention to be more emphasized are those compounds of formula I in which
R1, R2, R3, R4 and R5 are hydrogen,
R6 is -T1-Q1, in which T1 is a bond;
Q1 is any one selected from the group consisting of
3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl, 4'-(3-morpholin-4-yl-propyl)-biphenyl-4-yl, 3'-(3-morpholin-4-yl-propyl)-biphenyl-3-yl, 3'-(3-morpholin-4-yl-propyl)-biphenyl-4-yl, 4'-(4-methyl-piperazin-1-ylmethyl)-biphenyl-3-yl, 4'-(4-methyl-piperazin-1-ylmethyl)-biphenyl-4-yl, 3'-(4-methyl-piperazin-1-ylmethyl)-biphenyl-3-yl, 3'-(4-methyl-piperazin-1-ylmethyl)-biphenyl-4-yl, 4'-(2-morpholin-4-yl-ethoxy)-biphenyl-3-yl, 4'-(2-morpholin-4-yl-ethoxy)-biphenyl-4-yl, 3'-(2-morpholin-4-yl-ethoxy)-biphenyl-3-yl, 3'-(2-morpholin-4-yl-ethoxy)-biphenyl-4-yl, 4'-(3-morpholin-4-yl-propoxy)-biphenyl-3-yl, 4'-(3-morpholin-4-yl-propoxy)-biphenyl-4-yl, 3'-(3-morpholin-4-yl-propoxy)-biphenyl-3-yl, 3'-(3-morpholin-4-yl-propoxy)-biphenyl-4-yl, 4'-[2-(4-methyl-piperazin-1-yl)-ethoxy]-biphenyl-3-yl, 4'-[2-(4-methyl-piperazin-1-yl)-ethoxy]-biphenyl-4-yl, 3'-[2-(4-methyl-piperazin-1-yl)-ethoxy]-biphenyl-3-yl, 3'-[2-(4-methyl-piperazin-1-yl)-ethoxy]biphenyl-4-yl, 4'-(2-pyrrolidin-1-yl-ethoxy]-biphenyl-3-yl, 4'-(2-pyrrolidin-1-yl-ethoxy]biphenyl-4-yl, 3'-(2-pyrrolidin-1-yl-ethoxy]-biphenyl-3-yl, 3'-(2-pyrrolidin-1-yl-ethoxy]biphenyl-4-yl, 3'-(3-pyrrolidin-1-yl-propoxy]-biphenyl-4-yl, 4'-(3-pyrrolidin-1-yl-propoxy]-biphenyl-4-yl, 3'-(3-pyrrolidin-1-yl-propoxy]-biphenyl-3-yl, 4'-(3-pyrrolidin-1-yl-propoxy]-biphenyl-3-yl, 4'-[3-(4-methyl-piperazin-1-yl)-propoxy]-biphenyl-4-yl, 3'-[3-(4-methyl-piperazin-1-yl)-propoxy]-biphenyl-4-yl, 4'-[3-(4-methyl-piperazin-1-yl)-propoxy]-biphenyl-3-yl, 3'-[3-(4-methyl-piperazin-1-yl)-propoxy]-biphenyl-3-yl, 4'-(2-(1-methyl-piperidin-4-yl)-ethoxy)-biphenyl-4-yl, 4'-(2-(1-methyl-piperidin-4-yl)-ethoxy)-biphenyl-3-yl, 3'-(2-(1-methyl-piperidin-4-yl)-ethoxy)-biphenyl-4-yl, 3'-(2-(1-methyl-piperidin-4-yl)-ethoxy)-biphenyl-3-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl, 3'-dimethylaminomethyl-biphenyl-3-yl, 3'-[(2-dimethylamino-ethylamino)-carbonyl]-biphenyl-4-yl, 4'-[(2-dimethylamino-ethylamino)-carbonyl]-biphenyl-4-yl, 4'-[(2-dimethylamino-ethylamino)-carbonyl]biphenyl-3-yl, 3'-[(2-dimethylamino-ethylamino)-carbonyl]-biphenyl-3-yl, 2'-methylsulphonylamino-biphenyl-4-yl, 3'-methylsulphonylamino-biphenyl-4-yl, 4'-methylsulphonylamino-biphenyl-4-yl, 2'-methylsulphonylamino-biphenyl-3-yl, 3'-methylsulphonylamino-biphenyl-3-yl, 4'-methylsulphonylamino-biphenyl-3-yl, 4'-methylsulphonylamino-biphenyl-3-yl, 4'-dimethylsulphamoyl-biphenyl-4-yl, 4'-dimethylsulphamoyl-biphenyl-3-yl, 3'-dimethylsulphamoyl-biphenyl-4-yl, 3'-dimethylsulphamoyl-biphenyl-3-yl, 3'-acetamido-biphenyl-4-yl, 4'-acetamido-biphenyl-4-yl, 3'-acetamido-biphenyl-3-yl, 4'-acetamido-biphenyl-3-yl, 3'-amino-biphenyl-4-yl, 3'-dimethylamino-biphenyl-4-yl, 4'-morpholin-4-yl-biphenyl-4-yl, 4'-hydroxy-biphenyl-4-yl, 3'-trifluoromethyl-biphenyl-4-yl, 4'-methoxy-biphenyl-4-yl, 3'-amino-biphenyl-3-yl, 3'-dimethylamino-biphenyl-3-yl, 4'-morpholin-4-yl-biphenyl-3-yl, 4'-hydroxy-biphenyl-3-yl, 3'-trifluoromethyl-biphenyl-3-yl, 4'-methoxy-biphenyl-3-yl, 4'-amino-biphenyl-4-yl, 4'-dimethylamino-biphenyl-4-yl, 3'-morpholin-4-yl-biphenyl-4-yl, 3'-hydroxy-biphenyl-4-yl, 4'-trifluoromethyl-biphenyl-4-yl, 3'-methoxy-biphenyl-4-yl, 4'-amino-biphenyl-3-yl, 4'-dimethylamino-biphenyl-3-yl, 3'-morpholin-4-yl-biphenyl-3-yl, 3'-hydroxy-biphenyl-3-yl, 4'-trifluoromethyl-biphenyl-3-yl and 3'-methoxy-biphenyl-3-yl, 4'-(2-methoxy-ethylamino)methyl-biphenyl-3-yl, 4'-(2-methoxy-ethylamino)methyl-biphenyl-4-yl, 3'-(2-methoxy-ethylamino)methyl-biphenyl-3-yl, 3'-(2-methoxy-ethylamino)methyl-biphenyl-4-yl, 4'-aminomethyl-biphenyl-3-yl, 4'-aminomethyl-biphenyl-4-yl, 3'-aminomethyl-biphenyl-3-yl, 3'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl, 4'-(acetylamino)-methyl-biphenyl-3-yl, 4'-(methylsulphonylamino)-methyl-biphenyl-3-yl, 3'-(acetylamino)-methyl-biphenyl-4-yl, 3'-(methylsulphonylamino)-methyl-biphenyl-4-yl, 4'-cyclopentylaminomethyl-biphenyl-4-yl, 4'-cyclopentylaminomethyl-biphenyl-3-yl, 3'-cyclopentylaminomethyl-biphenyl-4-yl, 3'-cyclopentylaminomethyl-biphenyl-3-yl, 4'-cyclopropylaminomethyl-biphenyl-3-yl, 4'-cyclopropylaminomethyl-biphenyl-4-yl, 3'-cyclopropylaminomethyl-biphenyl-3-yl, 3'-cyclopropylaminomethyl-biphenyl-4-yl, 3'-hydroxymethyl-biphenyl-4-yl, 3'-hydroxymethyl-biphenyl-3-yl, 4'-hydroxymethyl-biphenyl-4-yl, 4'-hydroxymethyl-biphenyl-3-yl, 5-[2-(4-methyl-piperazin-1-yl)-pyridin-4-yl]-thiophen-2-yl, 5-(1-methyl-pyrazol-4-yl)-thiophen-2-yl, 6-(1-methyl-pyrazol-4-yl)-pyridin-3-yl, 2'-(4-methyl-piperazin-1-yl)-2,4'-bipyridyl-5-yl, 5-(2-methyl-thiazol-4-yl)-thiophen-2-yl, 5-[4-(2-morpholin-4-yl-ethyl)-phenyl]-thiophen-2-yl, 5-[3-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 5-[4-(2-morpholin-4-yl-ethoxy)-phenyl]-thiophen-2-yl, 5-[3-(2-morpholin-4-yl-ethoxy)-phenyl]-thiophen-2-yl, 5-[4-(3-morpholin-4-yl-propoxy)-phenyl]-thiophen-2-yl, 5-[3-(3-morpholin-4-yl-propoxy)-phenyl]-thiophen-2-yl, 5-{4-[2-(4-methyl-piperazin-1-yl)-ethoxy]-phenyl}-thiophen-2-yl, 5-{3-[2-(4-methyl-piperazin-1-yl)-ethoxy]-phenyl}-thiophen-2-yl, 5-[4-(2-pyrrolidin-1-yl-ethoxy)-phenyl]-thiophen-2-yl, 5-[3-(2-pyrrolidin-1-yl-ethoxy)-phenyl]-thiophen-2-yl, 5-(4-dimethylaminomethyl-phenyl)-thiophen-2-yl, 5-(3-dimethylaminomethyl-phenyl)-thiophen-2-yl, 6-(4-dimethylaminomethyl-phenyl)-pyridin-3-yl, 6-(3-dimethylaminomethyl-phenyl)-pyridin-3-yl, 6-[4-(2-pyrrolidin-1-yl-ethoxy)-phenyl]-pyridin-3-yl, 6-[3-(2-pyrrolidin-1-yl-ethoxy)-phenyl]-pyridin-3-yl, 5-(3-aminomethyl-phenyl)-thiophen-2-yl, 5-[3-(acetylamino)-methyl-phenyl]-thiophen-2-yl, 5-[3-(methylsulphonylamino)-methyl-phenyl]-thiophen-2-yl, 5-(4-dimethylsulphamoyl-phenyl)-thiophen-2-yl, 5-(4-aminomethyl-phenyl)-thiophen-2-yl, 5-[4-(acetylamino)-methyl-phenyl]-thiophen-2-yl, 5-[4-(methylsulphonylamino)-methyl-phenyl]-thiophen-2-yl, 5-(3-dimethylsulphamoyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-(6-amino-pyridin-3-yl)-phenyl, 3-(6-amino-pyridin-3-yl)-phenyl, 4-(6-methoxy-pyridin-3-yl)-phenyl, 3-(6-methoxy-pyridin-3-yl)-phenyl, 3-(1-methyl-pyrazol-4-yl)-phenyl, 4-(1-methyl-pyrazol-4-yl)-phenyl, 4-(3,5-dimethyl-isoxazol-4-yl)-phenyl, 3-(3,5-dimethyl-isoxazol-4-yl)-phenyl, 4-(1-methyl-indol-5-yl)-phenyl, 3-(1-methyl-indol-5-yl)-phenyl, 4-{1-(2-morpholin-4-yl-ethyl)-[1,2,3]triazol-4-yl}-phenyl, 4-{1-(2-piperidin-1-yl-ethyl)-[1,2,3]triazol-4-yl}-phenyl, 3-{1-(2-morpholin-4-yl-ethyl)-[1,2,3]triazol-4-yl}-phenyl, 3-{1-(2-piperidin-1-yl-ethyl)-[1,2,3]triazol-4-yl}-phenyl, 4-(2,3-dihydrobenzofuran-5-yl)-phenyl, and 4-(benzo[1,3]dioxol-5-yl)-phenyl, 3-(2,3-dihydrobenzofuran-5-yl)-phenyl, and 3-(benzo[1,3]dioxol-5-yl)-phenyl, R7 is hydroxyl,
and the salts of these compounds.

Compounds according to aspect A of the present invention to be more emphasized are those compounds of formula I in which R1, R2, R3, R4 and R5 are hydrogen,
R6 is -T1-Q1, in which T1 is a bond;
Q1 is any one selected from the group consisting of 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-4-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl, 4'-(3-morpholin-4-yl-propyl)-biphenyl-4-yl, 3'-(3-morpholin-4-yl-propyl)-biphenyl-3-yl, 3'-(3-morpholin-4-yl-propyl)-biphenyl-4-yl, 4'-(4-methyl-piperazin-1-ylmethyl)-biphenyl-3-yl, 4'-(4-methyl-piperazin-1-ylmethyl)-biphenyl-4-yl, 3'-(4-methyl-piperazin-1-ylmethyl)-biphenyl-3-yl, 3'-(4-methyl-piperazin-1-ylmethyl)-biphenyl-4-yl, 4'-(2-morpholin-4-yl-ethoxy)-biphenyl-3-yl, 4'-(2-morpholin-4-yl-ethoxy)-biphenyl-4-yl, 3'-(2-morpholin-4-yl-ethoxy)-biphenyl-3-yl, 3'-(2-morpholin-4-yl-ethoxy)-biphenyl-4-yl, 4'-(3-morpholin-4-yl-propoxy)-biphenyl-3-yl, 4'-(3-morpholin-4-yl-propoxy)-biphenyl-4-yl, 3'-(3-morpholin-4-yl-propoxy)-biphenyl-3-yl, 3'-(3- morpholin-4-yl-propoxy)-biphenyl-4-yl, 4'-[2-(4-methyl-piperazin-1-yl)-ethoxy]-biphenyl-3-yl, 4'-[2-(4-methyl-piperazin-1-yl)-ethoxy]-biphenyl-4-yl, 3'-[2-(4-methyl-piperazin-1-yl)-ethoxy]biphenyl-3-yl, 3'-[2-(4-methyl-piperazin-1-yl)-ethoxy]-biphenyl-4-yl, 4'-(2-pyrrolidin-1-yl-ethoxy]biphenyl-3-yl, 4'-(2-pyrrolidin-1-yl-ethoxy)-biphenyl-4-yl, 3'-(2-pyrrolidin-1-yl-ethoxy]biphenyl-3-yl, 3'-(2-pyrrolidin-1-yl-ethoxy]-biphenyl-4-yl, 3'-(3-pyrrolidin-1-yl-propoxy]-biphenyl-4-yl, 4'-(3-pyrrolidin-1-yl-propoxy]-biphenyl-4-yl, 3'-(3-pyrrolidin-1-yl-propoxy]-biphenyl-3-yl, 4'-(3-pyrrolidin-1-yl-propoxy]-biphenyl-3-yl, 4'-[3-(4-methyl-piperazin-1-yl)-propoxy]-biphenyl-4-yl, 3'-[3-(4-methyl-piperazin-1-yl)-propoxy]-biphenyl-4-yl, 4'-[3-(4-methyl-piperazin-1-yl)-propoxy]-biphenyl-3-yl, 3'-[3-(4-methyl-piperazin-1-yl)-propoxy]-biphenyl-3-yl, 4'-(2-(1-methyl-piperidin-4-yl)-ethoxy)-biphenyl-4-yl, 4'-(2-(1-methyl-piperidin-4-yl)-ethoxy)-biphenyl-3-yl, 3'-(2-(1-methyl-piperidin-4-yl)-ethoxy)-biphenyl-4-yl, 3'-(2-(1-methyl-piperidin-4-yl)-ethoxy)-biphenyl-3-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl, 3'-dimethylaminomethyl-biphenyl-3-yl, 3'-[(2-dimethylamino-ethylamino)-carbonyl]biphenyl-4-yl, 4'-[(2-dimethylamino-ethylamino)-carbonyl]-biphenyl-4-yl, 4'-[(2-dimethylamino-ethylamino)-carbonyl]-biphenyl-3-yl, 3'-[(2-dimethylamino-ethylamino)-carbonyl]biphenyl-3-yl, 2'-methylsulphonylamino-biphenyl-4-yl, 3'-methylsulphonylamino-biphenyl-4-yl, 4'-methylsulphonylamino-biphenyl-4-yl, 2'-methylsulphonylamino-biphenyl-3-yl, 3'-methylsulphonylamino-biphenyl-3-yl, 4'-methylsulphonylamino-biphenyl-3-yl, 4'-methylsulphonylamino-biphenyl-3-yl, 4'-dimethylsulphamoyl-biphenyl-4-yl, 4'-dimethylsulphamoyl-biphenyl-3-yl, 3'-dimethylsulphamoyl-biphenyl-4-yl, 3'-dimethylsulphamoyl-biphenyl-3-yl, 3'-acetamido-biphenyl-4-yl, 4'-acetamido-biphenyl-4-yl, 3'-acetamido-biphenyl-3-yl, 4'-acetamido-biphenyl-3-yl, 3'-amino-biphenyl-4-yl, 3'-dimethylamino-biphenyl-4-yl, 4'-morpholin-4-yl-biphenyl-4-yl, 4'-hydroxy-biphenyl-4-yl, 3'-trifluoromethyl-biphenyl-4-yl, 4'-methoxy-biphenyl-4-yl, 3'-amino-biphenyl-3-yl, 3'-dimethylamino-biphenyl-3-yl, 4'-morpholin-4-yl-biphenyl-3-yl, 4'-hydroxy-biphenyl-3-yl, 3'-trifluoromethyl-biphenyl-3-yl, 4'-methoxy-biphenyl-3-yl, 4'-amino-biphenyl-4-yl, 4'-dimethylamino-biphenyl-4-yl, 3'-morpholin-4-yl-biphenyl-4-yl, 3'-hydroxy-biphenyl-4-yl, 4'-trifluoromethyl-biphenyl-4-yl, 3'-methoxy-biphenyl-4-yl, 4'-amino-biphenyl-3-yl, 4'-dimethylamino-biphenyl-3-yl, 3'-morpholin-4-yl-biphenyl-3-yl, 3'-hydroxy-biphenyl-3-yl, 4'-trifluoromethyl-biphenyl-3-yl and 3'-methoxy-biphenyl-3-yl, 4'-(2-methoxy-ethylamino)methyl-biphenyl-3-yl, 4'-(2-methoxy-ethylamino)methyl-biphenyl-4-yl, 3'-(2-methoxy-ethylamino)methyl-biphenyl-3-yl, 3'-(2-methoxy-ethylamino)methyl-biphenyl-4-yl, 4'-aminomethyl-biphenyl-3-yl, 4'-aminomethyl-biphenyl-4-yl, 3'-aminomethyl-biphenyl-3-yl, 3'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl, 4'-(acetylamino)-methyl-biphenyl-3-yl, 4'-(methylsulphonylamino)-methyl-biphenyl-3-yl, 3'-(acetylamino)-methyl-biphenyl-4-yl, 3'-(methylsulphonylamino)-methyl-biphenyl-4-yl, 4'-cyclopentylaminomethyl-biphenyl-4-yl, 4'-cyclopentylaminomethyl-biphenyl-3-yl, 3'-cyclopentylaminomethyl-biphenyl-4-yl, 3'-cyclopentylaminomethyl-biphenyl-3-yl, 4'-cyclopropylaminomethyl-biphenyl-3-yl, 4'-cyclopropylaminomethyl-biphenyl-4-yl, 3'-cyclopropylaminomethyl-biphenyl-3-yl, 3'-cyclopropylaminomethyl-biphenyl-4-yl, 3'-hydroxymethyl-biphenyl-4-yl, 3'-hydroxymethyl-biphenyl-3-yl, 4'-hydroxymethyl-biphenyl-4-yl, 4'-hydroxymethyl-biphenyl-3-yl, 5-[2-(4-methyl-piperazin-1-yl)-pyridin-4-yl]-thiophen-2-yl, 5-(1-methyl-pyrazol-4-yl)-thiophen-2-yl, 6-(1-methyl-pyrazol-4-yl)-pyridin-3-yl,
2'-(4-methyl-piperazin-1-yl)-2,4'-bipyridyl-5-yl, 5-(2-methyl-thiazol-4-yl)-thiophen-2-yl,
5-[4-(2-morpholin-4-yl-ethyl)-phenyl]-thiophen-2-yl, 5-[3-(2-morpholin-4-yl-ethyl)-phenyl]-thiophen-2-yl,
5-[4-(morpholin-4-yl-methyl)-phenyl]-thiophen-2-yl, 5-[3-(morpholin-4-yl-methyl)-phenyl]-thiophen-2-yl,
5-[4-(2-morpholin-4-yl-ethoxy)-phenyl]-thiophen-2-yl,
5-[3-(2-morpholin-4-yl-ethoxy)-phenyl]-thiophen-2-yl,
5-[4-(3-morpholin-4-yl-propoxy)-phenyl]-thiophen-2-yl,
5-[3-(3-morpholin-4-yl-propoxy)-phenyl]-thiophen-2-yl,
5-{4-[2-(4-methyl-piperazin-1-yl)-ethoxy]-phenyl}-thiophen-2-yl, 5-{3-[2-(4-methyl-piperazin-1-yl)-ethoxy]-phenyl}-thiophen-2-yl, 5-[4-(2-pyrrolidin-1-yl-ethoxy)-phenyl]-thiophen-2-yl, 5-[3-(2-pyrrolidin-1-yl-ethoxy)-phenyl]-thiophen-2-yl, 5-(4-dimethylaminomethyl-phenyl)-thiophen-2-yl, 5-(3-dimethylaminomethyl-phenyl)-thiophen-2-yl, 6-(4-dimethylaminomethyl-phenyl)-pyridin-3-yl, 6-(3-dimethylaminomethyl-phenyl)-pyridin-3-yl, 6-[4-(2-pyrrolidin-1-yl-ethoxy)-phenyl]-pyridin-3-yl, 6-[3-(2-pyrrolidin-1-yl-ethoxy)-phenyl]-pyridin-3-yl, 5-(3-aminomethyl-phenyl)-thiophen-2-yl, 5-[3-(acetylamino)-methyl-phenyl]-thiophen-2-yl, 5[3-(methylsulphonylamino)-methyl-phenyl]-thiophen-2-yl, 5-(4-dimethylsulphamoyl-phenyl)-thiophen-2-yl, 5-(4-aminomethyl-phenyl)-thiophen-2-yl, 5-[4-(acetylamino)-methyl-phenyl]-thiophen-2-yl, 5-[4-(methylsulphonylamino)-methyl-phenyl]-thiophen-2-yl, 5-(3-dimethylsulphamoyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-(6-amino-pyridin-3-yl)-phenyl, 3-(6-amino-pyridin-3-yl)-phenyl, 4-(6-methoxy-pyridin-3-yl)-phenyl, 3-(6-methoxy-pyridin-3-yl)-phenyl, 3-(1-methyl-pyrazol-4-yl)-phenyl, 4-(1-methyl-pyrazol-4-yl)-phenyl, 4-(3,5-dimethyl-isoxazol-4-yl)-phenyl, 3-(3,5-dimethyl-isoxazol-4-yl)-phenyl, 4-(1-methyl-indol-5-yl)-phenyl, 3-(1-methyl-indol-5-yl)-phenyl,
4-{1-(2-morpholin-4-yl-ethyl)-[1,2,3]triazol-4-yl}-phenyl, 4-{1-(2-piperidin-1-yl-ethyl)-[1,2,3]triazol-4-yl}-phenyl, 3-{1-(2-morpholin-4-yl-ethyl)-[1,2,3]triazol-4-yl}-phenyl, 3-{1-(2-piperidin-1-yl-ethyl)-[1,2,3]triazol-4-yl}-phenyl, 4-(2,3-dihydrobenzofuran-5-yl)-phenyl, and 4-(benzo[1,3]dioxol-5-yl)-phenyl, 3-(2,3-dihydrobenzofuran-5-yl)-phenyl, and 3-(benzo[1,3]dioxol-5-yl)-phenyl,
R7 is 2-aminophenyl,
and the salts of these compounds.

Compounds according to aspect B of the present invention to be more emphasized are those compounds of formula I in which
R1, R2, R3, R4 and R5 are independently hydrogen or 1-4C-alkyl,
R6 is -T1-Q1, in which T1 is a bond;
either
Q1 is substituted by R61 and/or R62, and is Aa1, Hh1, Ha1, Ha2, Ha3 or Ah1, Or Q1 is unsubstituted, and is Ha2 or Ha3,
in which
R61 is 1-4C-alkyl, 1-4C-alkoxy, halogen, hydroxy-1-4C-alkyl, 1-4C-alkylsulphonylamino, tolylsulphonylamino, phenylsulphonylamino, 1-4C-alkylcarbonylamino, di-1-4C-alkylaminosulphonyl, -T2-N(R611)R612, or —U-T3-N(R613)R614, in which
T2 is a bond or 1-4C-alkylene,
R611 is hydrogen, 1-4C-alkyl, 3-7C-cycloalkyl or 1-4C-alkoxy-2-4C-alkyl,
R612 is hydrogen or 1-4C-alkyl,
or R611 and R612 together and with inclusion of the nitrogen atom, to which they are bonded, form a heterocyclic ring Het1, in which Het1 is morpholino, piperidino, pyrrolidino, piperazino or 4N-(1-4C-alkyl)-piperazino,
U is —O— (oxygen) or —C(O)NH—,
T3 is 2-4C-alkylene,
R613 is hydrogen, 1-4C-alkyl, 3-7C-cycloalkyl or 1-4C-alkoxy-2-4C-alkyl,
R614 is hydrogen or 1-4C-alkyl,
or R613 and R614 together and with inclusion of the nitrogen atom, to which they are bonded, form a heterocyclic ring Het2, in which
Het2 is morpholino, piperidino, pyrrolidino, piperazino or 4N-(1-4C-alkyl)-piperazino,
R62 is 1-4C-alkyl,
Aa1 is biphenyl,
Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group,
Ha1 is a heteroaryl-phenyl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group,
R7 is hydroxyl, or 2-aminophenyl,
and the salts of these compounds.

Compounds according to aspect B of the present invention to be more emphasized are those compounds of formula I in which
R1, R2, R3, R4 and R5 are hydrogen,
R6 is -T1-Q1, in which T1 is a bond;
Q1 is substituted by R61 and/or R62 on the terminal ring, and is Aa1, Hh1, Ha1, Ha2 or Ah1,
in which
R61 is 1-2C-alkyl, 1-2C-alkoxy, halogen, hydroxy-1-2C-alkyl, 1-2C-alkylsulphonylamino, 1-2C-alkylcarbonylamino, di-1-2C-alkylaminosulphonyl, -T2-N(R611)R612, or —U-T3-N(R613)R614, in which
T2 is a bond or straight chain 1-4C-alkylene,
R611 is hydrogen, 1-2C-alkyl, 3-5C-cycloalkyl or 1-2C-alkoxy-2-3C-alkyl,
R612 is hydrogen or 1-2C-alkyl,
or R611 and R612 together and with inclusion of the nitrogen atom, to which they are bonded, form a heterocyclic ring Het1, in which
Het1 is morpholino, piperidino, pyrrolidino, piperazino or 4N-(1-2C-alkyl)-piperazino,
U is —O— (oxygen) or —C(O)NH—,
T3 is straight chain 2-4C-alkylene,
R613 is hydrogen, 1-2C-alkyl, 3-5C-cycloalkyl or 1-2C-alkoxy-2-3C-alkyl,
R614 is hydrogen or 1-2C-alkyl,
or R613 and R614 together and with inclusion of the nitrogen atom, to which they are bonded, form a heterocyclic ring Het2, in which
Het2 is morpholino, piperidino, pyrrolidino, piperazino or 4N-(1-4C-alkyl)-piperazino,
R62 is 1-2C-alkyl,
Aa1 is 1,1'-biphenyl-3-yl or 1,1'-biphenyl-4-yl,
Hh1 is a bisheteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a thiophenyl group, whereby said heteroaryl and thiophenyl groups are linked together via a single bond, and whereby Hh1 is bonded via said thiophenyl moiety to the to the parent molecular group,
Ah1 is phenyl-thiophenyl,
Ha1 is a 3-(heteroaryl)-phenyl or 4-(heteroaryl)-phenyl radical each made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a 3-(heteroaryl)-phenyl or 4-(heteroaryl)-phenyl radical each made up of a heteroaryl group selected from a group consisting of fused bicyclic 9- or 10-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
R7 is hydroxyl, or 2-aminophenyl,
and the salts of these compounds.

Compounds according to aspect B of the present invention to be more emphasized are those compounds of formula I in which
R1, R2, R3, R4 and R5 are hydrogen,
R6 is -T1-Q1, in which T1 is a bond;
Q1 is substituted by R61 and/or R62 on the terminal ring, and is Aa1, Hh1, Ha1, Ha2 or Ah1,
in which
R61 is 1-2C-alkyl, 1-2C-alkoxy, hydroxyl, trifluoromethyl, halogen, hydroxy-1-2C-alkyl, 1-2C-alkylsulphonylamino, 1-2C-alkylcarbonylamino, di-1-2C-alkylaminosulphonyl, -T2-N(R611)R612, or —U-T3-N(R613)R614, in which
T2 is a bond or straight chain 1-4C-alkylene,
R611 is hydrogen, 1-2C-alkyl, 3-5C-cycloalkyl or 1-2C-alkoxy-2-3C-alkyl,
R612 is hydrogen or 1-2C-alkyl,
or R611 and R612 together and with inclusion of the nitrogen atom, to which they are bonded, form a heterocyclic ring Het1, in which
Het1 is morpholino, piperidino, pyrrolidino, piperazino or 4N-(1-2C-alkyl)-piperazino,
U is —O— (oxygen) or —C(O)NH—,
T3 is straight chain 2-4C-alkylene,
R613 is hydrogen, 1-2C-alkyl, 3-5C-cycloalkyl or 1-2C-alkoxy-2-3C-alkyl,
R614 is hydrogen or 1-2C-alkyl,
or R613 and R614 together and with inclusion of the nitrogen atom, to which they are bonded, form a heterocyclic ring Het2, in which
Het2 is morpholino, piperidino, pyrrolidino, piperazino or 4N-(1-4C-alkyl)-piperazino,
R62 is 1-2C-alkyl,
Aa1 is 1,1'-biphenyl-3-yl or 1,1'-biphenyl-4-yl,
Hh1 is a bisheteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a thiophenyl group, whereby said heteroaryl and thiophenyl groups are linked together via a single bond, and whereby Hh1 is bonded via said thiophenyl moiety to the to the parent molecular group,
Ah1 is phenyl-thiophenyl or phenyl-pyridinyl,
Ha1 is a 3-(heteroaryl)-phenyl or 4-(heteroaryl)-phenyl radical each made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a 3-(heteroaryl)-phenyl or 4-(heteroaryl)-phenyl radical each made up of a heteroaryl group selected from a group consisting of fused bicyclic 9- or 10-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
R7 is hydroxyl, or 2-aminophenyl,
and the salts of these compounds.

Compounds according to aspect B of the present invention to be more emphasized are those compounds of formula I in which
R1, R2, R3, R4 and R5 are hydrogen,
R6 is -T1-Q1, in which T1 is a bond;
Q1 is substituted by R61 on the terminal ring, and is Aa1 or Ah1, in which
Aa1 is 1,1'-biphenyl-3-yl or 1,1'-biphenyl-4-yl,
Ah1 is phenyl-thiophenyl,
R61 is methoxy, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
R611 is hydrogen, methyl, cyclopropyl or 2-methoxyethyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino,
U is —O— (oxygen) or —C(O)NH—,
T3 is dimethylene or trimethylene,
R613 is hydrogen, methyl, cyclopropyl or 2-methoxyethyl,
R614 is hydrogen or methyl,
or R613 and R614 together and with inclusion of the nitrogen atom, to which they are bonded, form a heterocyclic ring Het2, in which
Het2 is morpholino, piperidino, pyrrolidino, piperazino or 4N-methyl-piperazino,
or
Q1 is substituted by R61 on the terminal ring, and is Hh1 or Ha1, in which
Hh1 is pyridinyl-thiophenyl,
Ha1 is 3-(pyridinyl)-phenyl or 4-(pyridinyl)-phenyl,
R61 is methoxy, or -T2-N(R611)R612, in which
T2 is a bond, methylene, dimethylene or trimethylene,
R611 is hydrogen, methyl, cyclopropyl or 2-methoxyethyl,
R612 is hydrogen or methyl,
or R611 and R612 together and with inclusion of the nitrogen atom, to which they are bonded, form a heterocyclic ring Het1, in which Het1 is morpholino, piperidino, pyrrolidino, piperazino or 4N-methyl-piperazino,
or
Q1 is 3-(1N-methyl-pyrazolyl)-phenyl, 4-(1N-methyl-pyrazolyl)-phenyl, 3-(1N-methyl-indolyl)-phenyl or 4-(1N-methyl-indolyl)-phenyl,
R7 is hydroxyl, or 2-aminophenyl,
and the salts of these compounds.

Yet compounds according to aspect B of the present invention in more particular worthy to be mentioned are those compounds of formula I in which
R1, R2, R3, R4 and R5 are all hydrogen,
R6 is -T1-Q1, in which T1 is a bond,
Q is (1N-methyl-pyrazolyl)-thiophenyl, 3-(dimethyl-isoxazolyl)-phenyl or 4-(dimethyl-isoxazolyl)-phenyl,
and the salts of these compounds.

In another embodiment, still yet compounds according to aspect B of the present invention in more particular worthy to be mentioned are those compounds of formula I in which R1, R2, R3, R4 and R5 are all hydrogen,
R6 is -T1-Q1, in which T1 is a bond,
Q1 is substituted by R61 on the terminal ring, and is Aa1 or Ah1, in which
Aa1 is 1,1'-biphenyl-3-yl or 1,1'-biphenyl-4-yl,
Ah1 is phenyl-thiophenyl or phenyl-pyridinyl,
R61 is methoxy, hydroxyl, trifluoromethyl, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
R611 is hydrogen, methyl, cyclopropyl, cyclopentyl or 2-methoxyethyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino,
U is —O— (oxygen) or —C(O)NH—,
T3 is dimethylene or trimethylene,
R613 is hydrogen, methyl, cyclopropyl, cyclopentyl or 2-methoxyethyl,
R614 is hydrogen or methyl,
or R613 and R614 together and with inclusion of the nitrogen atom, to which they are bonded, form a heterocyclic ring Het2, in which
Het2 is morpholino, piperidino, pyrrolidino, piperazino or 4N-methyl-piperazino,
or
Q1 is substituted by R61 on the terminal ring, and is Hh1 or Ha1, in which
Hh1 is pyridinyl-thiophenyl or bipyridyl,
Ha1 is 3-(pyridinyl)-phenyl or 4-(pyridinyl)-phenyl,
R61 is methoxy, or -T2-N(R611)R612, in which
T2 is a bond, methylene, dimethylene or trimethylene,
R611 is hydrogen, methyl, cyclopropyl, cyclopentyl or 2-methoxyethyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino,
or
Q1 is 3-(1N-methyl-pyrazolyl)-phenyl, 4-(1N-methyl-pyrazolyl)-phenyl, (1N-methyl-pyrazolyl)-thiophenyl, (1N-methyl-pyrazolyl)-pyridinyl, 3-(methyl-thiazolyl)-phenyl, 4-(methyl-thiazolyl)-phenyl, (methyl-thiazolyl)-thiophenyl, (methyl-thiazolyl)-pyridinyl, 3-(dimethyl-isoxazolyl)-phenyl, 4-(dimethyl-isoxazolyl)-phenyl, 3-(1N-methyl-indolyl)-phenyl or 4-(1N-methyl-indolyl)-phenyl,
R7 is hydroxyl, or 2-aminophenyl,
and the salts of these compounds.

Compounds according to aspect B of the present invention to be emphasized are those compounds of formula I in which
R1, R2, R3, R4 and R5 are all hydrogen,
R6 is -T1-Q1, in which T1 is a bond,
Q1 is substituted by R61 on the terminal ring, and is Aa1 or Ah1, in which
Aa1 is 1,1'-biphenyl-3-yl or 1,1'-biphenyl-4-yl,
Ah1 is phenyl-thiophenyl,
R61 is hydroxymethyl, methylsulphonylamino, methylcarbonylamino, dimethylaminosulphonyl, -T2-N(R611)R612, or —U-T3-N(R613)R614, in which
T2 is methylene, dimethylene or trimethylene,
R611 is methyl, cyclopropyl or 2-methoxyethyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino or 4N-methyl-piperazino,
U is —O— (oxygen) or —C(O)NH—,
T3 is dimethylene or trimethylene,
R613 and R614 are methyl,
or R613 and R614 together and with inclusion of the nitrogen atom, to which they are bonded, form a heterocyclic ring Het2, in which Het2 is morpholino, piperidino, pyrrolidino or 4N-methyl-piperazino,
or
Q1 is substituted by R61 on the terminal ring, and is Hh1 or Ha1, in which
Hh1 is pyridinyl-thiophenyl,
Ha1 is 3-(pyridinyl)-phenyl or 4-(pyridinyl)-phenyl,
R61 is methoxy, or -T2-N(R611)R612, in which
T2 is a bond,
R611 and R612 are independently is hydrogen or methyl,
or R611 and R612 together and with inclusion of the nitrogen atom, to which they are bonded, form a heterocyclic ring Het1, in which
Het1 is morpholino, piperidino, pyrrolidino or 4N-methyl-piperazino,
or
Q1 is 3-(1N-methyl-pyrazolyl)-phenyl, 4-(1N-methyl-pyrazolyl)-phenyl, 3-(1N-methyl-indolyl)-phenyl or 4-(1N-methyl-indolyl)-phenyl,
R7 is hydroxyl, or 2-aminophenyl,
and the salts of these compounds.

Yet compounds according to aspect B of the present invention to be emphasized are those compounds of formula I in which
R1, R2, R3, R4 and R5 are all hydrogen,
R6 is -T1-Q1, in which T1 is a bond,
Q is (1N-methyl-pyrazol-4-yl)-thiophenyl, 3-(dimethyl-isoxazolyl)-phenyl or 4-(dimethyl-isoxazolyl)-phenyl,
and the salts of these compounds.

In another embodiment, still yet compounds according to aspect B of the present invention to be emphasized are those compounds of formula I in which
R1, R2, R3, R4 and R5 are all hydrogen,
R6 is -T1-Q1, in which T1 is a bond,
Q1 is 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is methoxy, hydroxyl, trifluoromethyl, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
R611 is hydrogen, methyl, cyclopropyl, cyclopentyl or 2-methoxyethyl,
R612 is hydrogen or methyl,
or R611 and R612 together and with inclusion of the nitrogen atom, to which they are bonded, form a heterocyclic ring Het1, in which
Het1 is morpholino, piperidino, pyrrolidino or 4N-methyl-piperazino,
either
U is —O— (oxygen),
T3 is dimethylene or trimethylene, R613 and R614 together and with inclusion of the nitrogen atom, to which they are bonded, form a heterocyclic ring Het2, in which
Het2 is morpholino, piperidino, pyrrolidino or 4N-methyl-piperazino,
or
U is —C(O)NH—,
T3 is dimethylene or trimethylene,
R613 and R614 are methyl,
or
Q1 is 5-[3-(R61)-phenyl]thiophen-2-yl, 5-[4-(R61)-phenyl]thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which
R61 is methoxy, hydroxyl, trifluoromethyl, hydroxymethyl, methylsulphonylamino, methylcarbonylamino, dimethylaminosulphonyl, -T2-N(R611)R612, or —U-T3-N(R613)R614, in which T2 is a bond, methylene, dimethylene or trimethylene,
either
R611 is methyl, cyclopropyl, cyclopentyl or 2-methoxyethyl,
R612 is hydrogen,
or R611 and R612 are hydrogen,
or R611 and R612 are methyl,
or R611 and R612 together and with inclusion of the nitrogen atom, to which they are bonded, form a heterocyclic ring Het1, in which
Het1 is morpholino, piperidino, pyrrolidino or 4N-methyl-piperazino,
either
U is —O— (oxygen),
T3 is dimethylene or trimethylene,
R613 and R614 together and with inclusion of the nitrogen atom, to which they are bonded, form a heterocyclic ring Het2, in which
Het2 is morpholino, piperidino, pyrrolidino or 4N-methyl-piperazino,
or
Q1 is 5-[2-(R61)-pyridin-4-yl]-thiophen-2-yl or 5-[6-(R61)-pyridin-3-yl]-thiophen-2-yl, in which
R61 is amino, methoxy, dimethylamino, or -T2-N(R611)R612, in which
T2 is a bond,
R611 and R612 together and with inclusion of the nitrogen atom, to which they are bonded, form a heterocyclic ring Het1, in which
Het1 is morpholino, piperidino, pyrrolidino or 4N-methyl-piperazino,
or
Q1 is 2-[2-(R61)-pyridin-4-yl]-pyridin-4-yl, 2-[6-(R61)-pyridin-3-yl]-pyridin-4-yl, 3-[2-(R61)-pyridin-4-yl]-pyridin-6-yl or 3-[6-(R61)-pyridin-3-yl]-pyridin-6-yl, in which
R61 is amino, methoxy, dimethylamino, or -T2-N(R611)R612, in which
T2 is a bond,
R611 and R612 together and with inclusion of the nitrogen atom, to which they are bonded, form a heterocyclic ring Het1, in which
Het1 is morpholino, piperidino, pyrrolidino or 4N-methyl-piperazino,
or
Q1 is 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which R61 is amino, methoxy, dimethylamino, or -T2-N(R611)R612, in which
T2 is a bond,
R611 and R612 together and with inclusion of the nitrogen atom, to which they are bonded, form a heterocyclic ring Het1, in which
Het1 is morpholino, piperidino, pyrrolidino or 4N-methyl-piperazino,
or
Q1 is 3-(1N-methyl-pyrazol-4-yl)-phenyl, 4-(1N-methyl-pyrazol-4-yl)-phenyl, 5-(1N-methyl-pyrazol-4-yl)-thiophen-2-yl, 6-(1N-methyl-pyrazol-4-yl)-pyridin-3-yl, 5-(2-methyl-thiazol-4-yl)-thiophen-2-yl, 3-(3,5-dimethyl-isoxazol-4-yl)-phenyl, 4-(3,5-dimethyl-isoxazol-4-yl)-phenyl, 3-(1N-methyl-indol-5-yl)-phenyl or 4-(1N-methyl-indol-5-yl)-phenyl,
R7 is hydroxyl, or 2-aminophenyl,
and the salts of these compounds.
Compounds according to aspect B of the present invention to be more emphasized are those compounds of formula I in which
R1, R2, R3, R4 and R5 are all hydrogen,
R6 is -T1-Q1, in which T1 is a bond,
Q1 is 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is hydroxymethyl, methylsulphonylamino, methylcarbonylamino, dimethylaminosulphonyl, -T2-N(R611)R612, or —U-T3-N(R613)R614, in which
T2 is methylene, dimethylene or trimethylene,
R611 is methyl, cyclopropyl or 2-methoxyethyl,
R612 is hydrogen or methyl,
or R611 and R612 together and with inclusion of the nitrogen atom, to which they are bonded, form a heterocyclic ring Het1, in which Het1 is morpholino, pyrrolidino or 4N-methyl-piperazino,
either
U is —O— (oxygen),
T3 is dimethylene or trimethylene,
R613 and R614 together and with inclusion of the nitrogen atom, to which they are bonded, form a heterocyclic ring Het2, in which
Het2 is morpholino, pyrrolidino or 4N-methyl-piperazino,
or
U is —C(O)NH—,
T3 is dimethylene or trimethylene,
R613 and R614 are methyl,
or
Q1 is 5-[3-(R61)-phenyl]-thiophen-2-yl or 5-[4-(R61)-phenyl]-thiophen-2-yl, in which
R61 is -T2-N(R611)R612, or —U-T3-N(R613)R614, in which
T2 is methylene, dimethylene or trimethylene,
R611 and R612 are methyl,
or R611 and R612 together and with inclusion of the nitrogen atom, to which they are bonded, form a heterocyclic ring Het1, in which
Het1 is morpholino, pyrrolidino or 4N-methyl-piperazino,
U is —O— (oxygen),
T3 is dimethylene or trimethylene,
R613 and R614 together and with inclusion of the nitrogen atom, to which they are bonded, form a heterocyclic ring Het2, in which Het2 is morpholino, pyrrolidino or 4N-methyl-piperazino, or Q1 is 5-[2-(R61)-pyridin-4-yl]-thiophen-2-yl or 5-[6-(R61)-pyridin-3-yl]-thiophen-2-yl, in which
R61 is amino, or -T2-N(R611)R612, in which T2 is a bond,
R611 and R612 together and with inclusion of the nitrogen atom, to which they are bonded, form a heterocyclic ring Het1, in which Het1 is morpholino, pyrrolidino or 4N-methyl-piperazino, Q1 is 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which
R61 is amino, methoxy, or -T2-N(R611)R612, in which T2 is a bond,
R611 and R612 together and with inclusion of the nitrogen atom, to which they are bonded, form a heterocyclic ring Het1, in which Het1 is morpholino, pyrrolidino or 4N-methyl-piperazino, or Q1 is 3-(1N-methyl-pyrazol-4-yl)-phenyl, 4-(1N-methyl-pyrazol-4-yl)-phenyl, 3-(1N-methyl-indol-5-yl)-phenyl or 4-(1N-methyl-indol-5-yl)-phenyl,
R7 is hydroxyl, or 2-aminophenyl,
and the salts of these compounds.

Yet compounds according to aspect B of the present invention to be more emphasized are those compounds of formula I in which
R1, R2, R3, R4 and R5 are all hydrogen,
R6 is -T1-Q1, in which T1 is a bond,
Q is 5-(1N-methyl-pyrazol-4-yl)-thiophen-2-yl, 3-(3,5-dimethyl-isoxazol-4-yl)-phenyl or 4-(3,5-dimethyl-isoxazol-4-yl)-phenyl,
and the salts of these compounds.

Compounds according to aspect B of the present invention to be in particular emphasized are those compounds of formula I in which
R1, R2, R3, R4 and R5 are all hydrogen,
R6 is -T1-Q1, in which T1 is a bond,
Q1 is any one selected from the group consisting of
3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 4'-(3-morpholin-4-yl-propyl)-biphenyl-3-yl, 4'-(4-methyl-piperazin-1-ylmethyl)-biphenyl-3-yl, 4'-(2-morpholin-4-yl-ethoxy)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-(2-pyrrolidin-1-yl-ethoxy]biphenyl-3-yl,
2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-[(2-dimethylamino-ethylamino)-carbonyl]biphenyl-4-yl, 4'-[(2-dimethylamino-ethylamino)-carbonyl]-biphenyl-4-yl, 4'-[(2-dimethylamino-ethylamino)-carbonyl]-biphenyl-3-yl, 2'-methylsulphonylamino-biphenyl-4-yl, 3'-methylsulphonylamino-biphenyl-4-yl, 4'-methylsulphonylamino-biphenyl-4-yl, 4'-dimethylsulphamoyl-biphenyl-4-yl, 3'-acetamido-biphenyl-4-yl, 4'-acetamido-biphenyl-4-yl, 4'-(2-methoxy-ethylamino)methyl-biphenyl-3-yl, 4'-cyclopropylaminomethyl-biphenyl-3-yl, 3'-hydroxymethyl-biphenyl-4-yl, 5-[2-(4-methyl-piperazin-1-yl)-pyridin-4-yl]-thiophen-2-yl, 5-(1N-methyl-pyrazol-4-yl)-thiophen-2-yl,
5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 5-[4-(2-morpholin-4-yl-ethoxy)-phenyl]-thiophen-2-yl,
5-[4-(3-morpholin-4-yl-propoxy)-phenyl]-thiophen-2-yl, 5-{4-[2-(4-methyl-piperazin-1-yl)-ethoxy]-phenyl}-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, 3-[6-amino-pyridin-3-yl]-phenyl, 4-[6-methoxy-pyridin-3-yl]-phenyl, 3-[6-methoxy-pyridin-3-yl]-phenyl,
3-(1N-methyl-pyrazol-4-yl)-phenyl, 4-(1N-methyl-pyrazol-4-yl)-phenyl, 4-(3,5-dimethyl-isoxazol-4-yl)-phenyl, and 4-(1N-methyl-indol-5-yl)-phenyl,
R7 is hydroxyl, or 2-aminophenyl,
and the salts of these compounds.

In one embodiment, compounds according to aspect B of the present invention to be in more particular emphasized are those compounds of formula I in which
R1, R2, R3, R4 and R5 are all hydrogen,
R6 is -T1-Q1, in which T1 is a bond,
Q1 is any one selected from the group consisting of
4'-(2-morpholin-4-yl-ethyl)-biphenyl-3-yl, 4'-(3-morpholin-4-yl-propoxy)-biphenyl-3-yl,
4'-[2-(4-methyl-piperazin-1-yl)-ethoxy]biphenyl-3-yl, 4'-dimethylaminomethyl-biphenyl-4-yl,
5-[2-(4-methyl-piperazin-1-yl)-pyridin-4-yl]-thiophen-2-yl, 5-(4-dimethylaminomethyl-phenyl)-thiophen-2-yl,
4-[2-(4-methyl-piperazin-1-yl)-pyridin-4-yl]-phenyl, 3-[2-(4-methyl-piperazin-1-yl)-pyridin-4-yl]-phenyl,
4-[6-amino-pyridin-3-yl]-phenyl, and 4-(1N-methyl-pyrazol-4-yl)-phenyl.
R7 is hydroxyl,
and the salts of these compounds.

In another embodiment, compounds according to aspect B of the present invention to be in more particular emphasized are those compounds of formula I in which
R1, R2, R3, R4 and R5 are all hydrogen,
R6 is -T1-Q1, in which T1 is a bond,
Q1 is any one selected from the group consisting of
4'-(2-morpholin-4-yl-ethyl)-biphenyl-3-yl, 4'-(3-morpholin-4-yl-propoxy)-biphenyl-3-yl, 4'-[2-(4-methyl-piperazin-1-yl)-ethoxy]biphenyl-3-yl, 4'-dimethylaminomethyl-biphenyl-4-yl, 5-[2-(4-methyl-piperazin-1-yl)-pyridin-4-yl]-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, and 4-(1N-methyl-pyrazol-4-yl)-phenyl,
R7 is 2-aminophenyl,
and the salts of these compounds.

In a first embodiment of aspect C (embodiment C1) of the present invention, compounds according to aspect C of the present invention more worthy to be mentioned are those compounds of formula I in which
R1, R2, R3, R4, and R5 are independently hydrogen, or 1-4C-alkyl,
R6 is -T1-Q1, in which T1 is a bond,
either
Q1 is substituted by R61 and/or R62, and is Aa1, Hh1, Ha1, Ha2, Ha3 or Ah1,
or Q1 is unsubstituted, and is Ha2 or Ha3,
in which
R61 is 1-4C-alkyl, 1-4C-alkoxy, halogen, or -T2-N(R611)R612, in which
T2 is a bond or 1-4C-alkylene,
R611 and R612 are independently hydrogen or 1-4C-alkyl, or R611 and R612 together and with inclusion of the nitrogen atom, to which they are bonded, form a heterocyclic ring Het1, in which Het1 is morpholino, piperidino, pyrrolidino, piperazino, or 4N-methyl-piperazino, R62 is 1-4C-alkyl, Aa1 is biphenyl, Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group, Ha1 is a heteroaryl-phenyl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group, R7 is hydroxyl, or 2-aminophenyl, and the salts of these compounds.

In a second embodiment of aspect C (embodiment $C_2$), compounds according to aspect C of the present invention more worthy to be mentioned are those compounds of formula I in which R1, R2, R3, R4 and R5 are independently hydrogen, or 1-4C-alkyl, R6 is -T1-Q1, in which T1 is a bond, either Q1 is substituted by R61, and is Aa1, Ha1, Ha2 or Ha3, Or Q1 is unsubstituted, and is Ha2 or Ha3, in which R61 is 1-4C-alkyl, 1-4C-alkoxy, halogen, or -T2-N(R611)R612, in which T2 is a bond or 1-4C-alkylene, R611 and R612 are independently hydrogen or 1-4C-alkyl, or R611 and R612 together and with inclusion of the nitrogen atom, to which they are bonded, form a heterocyclic ring Het1, in which Het1 is morpholino, piperidino, pyrrolidino, piperazino, or 4N-methyl-piperazino, Aa1 is biphenyl, Ha1 is a heteroaryl-phenyl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group, R7 is hydroxyl, or 2-aminophenyl, and the salts of these compounds.

Compounds according to embodiment C1 of aspect C of the present invention in particular worthy to be mentioned are those compounds of formula I in which R1, R2, R3, R4 and R5 are hydrogen, R6 is -T1-Q1, in which T1 is a bond, either Q1 is substituted by R61 on the terminal ring, and is Aa1, Hh1, Ha1 or Ah1, or Q1 is [1N-(1-4C-alkyl)-indolyl]-phenyl, [1N-(1-4C-alkyl)-pyrazolyl]-phenyl, [1N-(1-4C-alkyl)-imidazolyl]-phenyl, [1N-(1-4C-alkyl)-triazolyl]-phenyl, [1N-(1-4C-alkyl)-tetrazolyl]-phenyl, [1N-(1-4C-alkyl)-benzimidazolyl]-phenyl, [1N-(1-4C-alkyl)-benztriazolyl]-phenyl, or [1N-(1-4C-alkyl)-indazol]-phenyl, or Q1 is [1N-(1-4C-alkyl)-indolyl]-thiophenyl, [1N-(1-4C-alkyl)-pyrazolyl]-thiophenyl, [1N-(1-4C-alkyl)-imidazolyl]-thiophenyl, [1N-(1-4C-alkyl)-triazolyl]-thiophenyl, [1N-(1-4C-alkyl)-tetrazolyl]-thiophenyl, [1N-(1-4C-alkyl)-benzimidazolyl]-thiophenyl, [1N-(1-4C-alkyl)-benztriazolyl]-thiophenyl, or [1N-(1-4C-alkyl)-indazol]-thiophenyl, or Q1 is [mono- or di-(1-4C-alkyl)-isoxazolyl]-phenyl, or [mono- or di-(1-4C-alkyl)-isoxazolyl]-thiophenyl, in which R61 is 1-4C-alkyl, 1-4C-alkoxy, halogen, or -T2-N(R611)R612, in which T2 is a bond or 1-4C-alkylene, R611 is hydrogen or 1-4C-alkyl, R612 is hydrogen or 1-4C-alkyl, or R611 and R612 together and with inclusion of the nitrogen atom, to which they are bonded, form a heterocyclic ring Het1, in which Het1 is morpholino, piperidino, pyrrolidino, piperazino, or 4N-methyl-piperazino, Aa1 is 1,1'-biphenyl-4-yl or 1,1'-biphenyl-3-yl, Hh1 is pyridinyl-thiophenyl, Ha1 is 3-(pyridinyl)-phenyl or 4-(pyridinyl)-phenyl, Ah1 is phenyl-thiophenyl, R7 is hydroxyl, or 2-aminophenyl, and the salts of these compounds.

Compounds according to embodiment C2 of aspect C of the present invention in particular worthy to be mentioned are those compounds of formula I in which R1, R2, R3, R4 and R5 are hydrogen, R6 is -T1-Q1, in which T1 is a bond, either Q1 is substituted by R61 on the terminal ring, and is Aa1 or Ha1, or Q1 is [1N-(1-4C-alkyl)-indolyl]-phenyl, [1N-(1-4C-alkyl)-pyrazolyl]-phenyl, [1N-(1-4C-alkyl)-imidazolyl]-phenyl, [1N-(1-4C-alkyl)-triazolyl]-phenyl, [1N-(1-4C-alkyl)-tetrazolyl]-phenyl, [1N-(1-4C-alkyl)-benzimidazolyl]-phenyl, [1N-(1-4C-alkyl)-benztriazolyl]-phenyl, or [1N-(1-4C-alkyl)-indazol]-phenyl, in which R61 is 1-4C-alkyl, 1-4C-alkoxy, halogen, or -T2-N(R611)R612, in which T2 is a bond or 1-4C-alkylene, R611 is hydrogen or 1-4C-alkyl, R612 is hydrogen or 1-4C-alkyl, or R611 and R612 together and with inclusion of the nitrogen atom, to which they are bonded, form a heterocyclic ring Het1, in which Het1 is morpholino, piperidino, pyrrolidino, piperazino, or 4N-methyl-piperazino, Aa1 is 1,1'-biphenyl-4-yl or 1,1'-biphenyl-3-yl, Ha1 is 3-(pyridinyl)-phenyl or 4-(pyridinyl)-phenyl, R7 is hydroxyl, or 2-aminophenyl, and the salts of these compounds.

Compounds according to embodiment C1 of aspect C of the present invention in more particular worthy to be mentioned are those compounds of formula I in which R1, R2, R3, R4 and R5 are hydrogen, R6 is -T1-Q1, in which T1 is a bond, either Q1 is substituted by R61 on the pyridine ring, and is 3-(pyridinyl)-phenyl or 4-(pyridinyl)-phenyl, or Q1 is 2'-(R61)-1,1'-biphenyl-4-yl, 3'-(R61)-1,1'-biphenyl-4-yl, 4'-(R61)-1,1'-biphenyl-4-yl, 2'-(R61)-1,1'-biphenyl-3-yl, 3'-(R61)-1,1'-biphenyl-3-yl or 4'-(R61)-1,1'-biphenyl-3-yl, or Q1 is substituted by R61 on the pyridine ring, and is pyridinyl-thiophenyl, or Q1 is substituted by R61 on the phenyl ring, and is phenyl-thiophenyl, or Q1 is 3-[1N-methyl-indolyl]-phenyl, 4-[1N-methyl-indolyl]-phenyl, 3-[1N-methyl-pyrazolyl]-phenyl or 4-[1N-methyl-pyrazolyl]-phenyl, or Q1 is [1N-methyl-pyrazolyl]-thiophenyl, or Q1 is 3-[dimethyl-isoxazolyl]-phenyl or 4-[dimethyl-isoxazolyl]-phenyl, in which R61 is 1-2C-alkoxy, amino, or -T2-N(R611)R612, in which T2 is a bond, methylene, dimethylene or trimethylene, R611 is 1-2C-alkyl, R612 is 1-2C-alkyl, or R611 and R612 together and with inclusion of the nitrogen atom, to which they are bonded, form a heterocyclic ring Het1, in which Het1 is morpholino, pyrrolidino or 4N-methyl-piperazino, R7 is hydroxyl, or 2-aminophenyl, and the salts of these compounds.

Compounds according to embodiment C2 of aspect C of the present invention in more particular worthy to be mentioned are those compounds of formula I in which R1, R2, R3, R4 and R5 are hydrogen, R6 is -T1-Q1, in which T1 is a bond, either Q1 is substituted by R61 on the pyridine ring, and is 3-(pyridinyl)-phenyl or 4-(pyridinyl)-phenyl, or Q1 is 3'-(R61)-1,1'-biphenyl-4-yl or 4'-(R61)-1,1'-biphenyl-4-yl, or Q1 is 3-[1 N-methyl-indolyl]-phenyl, 4-[1 N-methyl-indolyl]-phenyl, 3-[1 N-methyl-pyrazolyl]-phenyl or 4-[1N-methyl-pyrazolyl]-phenyl, in which R61 is 1-2C-alkoxy, amino, or -T2-N(R611)R612, in which T2 is a bond or 1-2C-alkylene, R611 and R612 are 1-2C-alkyl, or R611 and R612 together and with inclusion of the nitrogen atom, to which they are bonded, form a heterocyclic ring Het1, in which Het1 is morpholino, R7 is hydroxyl, or 2-aminophenyl, and the salts of these compounds.

Compounds according to embodiment C1 of aspect C of the present invention to be emphasized are, in one embodiment, those compounds of formula in which R1, R2, R3, R4 and R5 are hydrogen, R6 is -T1-Q1, in which T1 is a bond, either Q1 is 3-(6-amino-pyridin-3-yl)-phenyl, 4-(6-amino-pyridin-3-yl)-phenyl, 3-(6-methoxy-pyridin-3-yl)-phenyl or 4-(6-methoxy-pyridin-3-yl)-phenyl, or Q1 is 3-[2-(4-methyl-piperazin-1-yl)-pyridin-4-yl)]-phenyl or 4-[2-(4-methyl-piperazin-1-yl)-pyridin-4-yl)]-phenyl, or Q1 is 3'-(R61)-1,1'-biphenyl-4-yl or 4'-(R61)-1,1'-biphenyl-4-yl, or Q1 is 5-[2-(4-methyl-piperazin-1-yl)-pyridin-4-yl)]-thiophen-2-yl, or Q1 is 5-[4-(R61)-phenyl]-thiophen-2-yl or 5-[3-(R61)-phenyl]-thiophen-2-yl, or Q1 is 3-(1N-methyl-indol-5-yl)-phenyl, 4-(1N-methyl-indol-5-yl)-phenyl, 3-(1N-methyl-pyrazol-4-yl)-phenyl or 4-(1N-methyl-pyrazol-4-yl)-phenyl, or Q1 is 5-(1N-methyl-pyrazol-4-yl)-thiophen-2-yl, or Q1 is 3-(3,5-dimethyl-isoxazol-4-yl)-phenyl or 4-(3,5-dimethyl-isoxazol-4-yl)-phenyl, in which R61 is -T2-N(R611)R612, in which T2 is methylene, dimethylene or trimethylene, either R611 and R612 are both methyl, or R611 and R612 together and with inclusion of the nitrogen atom, to which they are bonded, form a heterocyclic ring Het1, in which Het1 is morpholino or 4N-methyl-piperazino, R7 is hydroxyl, and the salts of these compounds.

Compounds according to embodiment C1 of aspect C of the present invention to be emphasized are, in another embodiment, those compounds of formula I in which R1, R2, R3, R4 and R5 are hydrogen,
R6 is -T1-Q1, in which T1 is a bond,
either
Q1 is 3-(6-amino-pyridin-3-yl)-phenyl, 4-(6-amino-pyridin-3-yl)-phenyl, 3-(6-methoxy-pyridin-3-yl)-phenyl or 4-(6-methoxy-pyridin-3-yl)-phenyl,
or Q1 is 3-[2-(4-methyl-piperazin-1-yl)-pyridin-4-yl)]-phenyl or 4-[2-(4-methyl-piperazin-1-yl)-pyridin-4-yl)]-phenyl,
or Q1 is 3'-(R61)-1,1'-biphenyl-4-yl or 4'-(R61)-1,1'-biphenyl-4-yl,
or Q1 is 5-[2-(4-methyl-piperazin-1-yl)-pyridin-4-yl)]-thiophen-2-yl,
or Q1 is 5-[4-(R61)-phenyl]-thiophen-2-yl or 5-[3-(R61)-phenyl]-thiophen-2-yl,
or Q1 is 3-(1N-methyl-indol-5-yl)-phenyl, 4-(1N-methyl-indol-5-yl)-phenyl, 3-(1N-methyl-pyrazol-4-yl)-phenyl or 4-(1N-methyl-pyrazol-4-yl)-phenyl,
or Q1 is 5-(1N-methyl-pyrazol-4-yl)-thiophen-2-yl,
or Q1 is 3-(3,5-dimethyl-isoxazol-4-yl)-phenyl or 4-(3,5-dimethyl-isoxazol-4-yl)-phenyl,
in which
R61 is -T2-N(R611)R612, in which T2 is methylene, dimethylene or trimethylene,
either
R611 and R612 are both methyl,
or
R611 and R612 together and with inclusion of the nitrogen atom, to which they are bonded, form a heterocyclic ring Het1, in which
Het1 is morpholino or 4N-methyl-piperazino,
R7 is 2-aminophenyl,
and the salts of these compounds.

Compounds according to embodiment C2 of aspect C of the present invention to be emphasized are those compounds of formula I in which R1, R2, R3, R4 and R5 are hydrogen,
R6 is -T1-Q1, in which T1 is a bond,
either
Q1 is 3-(6-amino-pyridin-3-yl)-phenyl, 4-(6-amino-pyridin-3-yl)-phenyl, 3-(6-methoxy-pyridin-3-yl)-phenyl or 4-(6-methoxy-pyridin-3-yl)-phenyl,
or Q1 is 3'-(R61)-1,1'-biphenyl-4-yl or 4'-(R61)-1,1'-biphenyl-4-yl,
or Q1 is 3-(1N-methyl-indol-5-yl)-phenyl, 4-(1N-methyl-indol-5-yl)-phenyl, 3-(1 N-methyl-pyrazol-4-yl)-phenyl or 4-(1N-methyl-pyrazol-4-yl)-phenyl,
in which
R61 is -T2-N(R611)R612, in which T2 is 1-2C-alkylene,
R611 and R612 together and with inclusion of the nitrogen atom, to which they are bonded, form a heterocyclic ring Het1, in which Het1 is morpholino,
R7 is hydroxyl, or 2-aminophenyl,
and the salts of these compounds.

Compounds according to embodiment C1 of aspect C of the present invention to be more emphasized are, in one embodiment, those compounds of formula I in which R1, R2, R3, R4 and R5 are hydrogen,
R6 is -T1-Q1, in which T1 is a bond,
Q1 is any one selected from 3-(6-amino-pyridin-3-yl)-phenyl, 4-(6-amino-pyridin-3-yl)-phenyl, 3-(6-methoxy-pyridin-3-yl)-phenyl, 4-(6-methoxy-pyridin-3-yl)-phenyl, 3-[2-(4-methyl-piperazin-1-yl)-pyridin-4-yl)]-phenyl, 4-[2-(4-methyl-piperazin-1-yl)-pyridin-4-yl)]-phenyl,
3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 4'-(3-morpholin-4-yl-propyl)-biphenyl-3-yl, 4'-(4-methyl-piperazin-1-yl-methyl)-biphenyl-3-yl,
2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl,
5-[2-(4-methyl-piperazin-1-yl)-pyridin-4-yl)]-thiophen-2-yl, 5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 4-(1N-methyl-indol-5-yl)-phenyl, 3-(1N-methyl-pyrazol-4-yl)-phenyl, 4-(1N-methyl-pyrazol-4-yl)-phenyl, 5-(4-dimethylaminomethyl-phenyl)-thiophen-2-yl,
5-(1N-methyl-pyrazol-4-yl)-thiophen-2-yl, and 4-(3,5-dimethyl-isoxazol-4-yl)-phenyl,
R7 is hydroxyl,
and the salts of these compounds.

Compounds according to embodiment C1 of aspect C of the present invention to be more emphasized are, in another embodiment, those compounds of formula I in which R1, R2, R3, R4 and R5 are hydrogen,
R6 is -T1-Q1, in which T1 is a bond,
Q1 is any one selected from 3-(6-amino-pyridin-3-yl)-phenyl, 4-(6-amino-pyridin-3-yl)-phenyl, 3-(6-methoxy-pyridin-3-yl)-phenyl, 4-(6-methoxy-pyridin-3-yl)-phenyl, 3-[2-(4-methyl-piperazin-1-yl)-pyridin-4-yl)]-phenyl, 4-[2-(4-methyl-piperazin-1-yl)-pyridin-4-yl)]-phenyl, 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 4'-(3-morpholin-4-yl-propyl)-biphenyl-3-yl, 4'-(4-methyl-piperazin-1-yl-methyl)-biphenyl-3-yl,
2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl,
5-[2-(4-methyl-piperazin-1-yl)-pyridin-4-yl)]-thiophen-2-yl,
5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 4-(1N-methyl-indol-5-yl)-phenyl, 3-(1N-methyl-pyrazol-4-yl)-phenyl, 4-(1 N-methyl-pyrazol-4-yl)-phenyl,
5-(4-dimethylaminomethyl-phenyl)-thiophen-2-yl, 5-(1N-methyl-pyrazol-4-yl)-thiophen-2-yl, and 4-(3,5-dimethyl-isoxazol-4-yl)-phenyl,
R7 is 2-aminophenyl,
and the salts of these compounds.

Compounds according to embodiment C1 of aspect C of the present invention to be in particular emphasized are, in one embodiment, those compounds of formula I in which R1, R2, R3, R4 and R5 are hydrogen,
R6 is -T1-Q1, in which T1 is a bond,
Q1 is any one selected from 4-(6-amino-pyridin-3-yl)-phenyl, 4-[2-(4-methyl-piperazin-1-yl)-pyridin-4-yl)]-phenyl, 3-[2-(4-methyl-piperazin-1-yl)-pyridin-4-yl)]-phenyl, 4'-(2-morpholin-4-yl-ethyl)-biphenyl-3-yl, 4'-dimethylaminomethyl-biphenyl-4-yl, 5-[2-(4- methyl-piperazin-1-yl)-pyridin-4-yl)]-thiophen-2-yl, 4-(1 N-methyl-pyrazol-4-yl)-phenyl, and 5-(4-dimethylaminomethyl-phenyl)-thiophen-2-yl, R7 is hydroxyl, and the salts of these compounds.

Compounds according to embodiment C1 of aspect C of the present invention to be in particular emphasized are, in another embodiment, those compounds of formula I in which R1, R2, R3, R4 and R5 are hydrogen, R6 is -T1-Q1, in which T1 is a bond, Q1 is any one selected from 4-(6-amino-pyridin-3-yl)-phenyl, 4-[2-(4-methyl-piperazin-1-yl)-pyridin-4-yl)]-phenyl, 3-[2-(4-methyl-piperazin-1-yl)-pyridin-4-yl)]-phenyl, 4'-(2-morpholin-4-yl-ethyl)-biphenyl-3-yl, 4'-dimethylaminomethyl-biphenyl-4-yl, 5-[2-(4-methyl-piperazin-1-yl)-pyridin-4-yl)]thiophen-2-yl, 4-(1N-methyl-pyrazol-4-yl)-phenyl, and 5-(4-dimethylaminomethyl-phenyl)-thiophen-2-yl, R7 is 2-aminophenyl, and the salts of these compounds.

A special interest in the compounds according to the present invention refers to those compounds of this invention which are included—within the scope of this invention—by one or, when possible, a combination of more of the following embodiments:

An embodiment of the compounds according to the present invention relates to those compounds of formula I, in which R1, R2, R3, R4 and R5 are all hydrogen.

A further embodiment of the compounds according to the present invention relates to those compounds of formula I, in which R7 is hydroxyl. A further embodiment of the compounds according to the present invention relates to those compounds of formula I, in which R7 is 2-aminophenyl. A further embodiment of the compounds according to the present invention relates to those compounds of formula I, in which R7 is aminopyridyl. A further embodiment of the compounds according to the present invention relates to those compounds of formula I, in which R7 is Cyc1, whereby in a subembodiment thereof Cyc1 is 2-phenyl.

A further embodiment of the compounds according to the present invention relates to those compounds of formula I, in which T1 is a bond.

A further embodiment of the compounds according to the present invention relates to those compounds of formula I, in which R6 is substituted by R61, and is Aa1, Ha1 or Ha2. A further embodiment of the compounds according to the present invention relates to those compounds of formula I, in which R6 is substituted by R61, and is Ah1 or Hh1. A further embodiment of the compounds according to the present invention relates to those compounds of formula I, in which R6 is substituted by R61, and is Ha3. A further embodiment of the compounds according to the present invention relates to those compounds of formula I, in which R6 is 3-(pyridinyl)-phenyl or 4-(pyridinyl)-phenyl, each of which is substituted by R61 on the pyridinyl moiety. A further embodiment of the compounds according to the present invention relates to those compounds of formula I, in which R6 is 3-(pyridin-3-yl)-phenyl, 3-(pyridin-4-yl)-phenyl, 4-(pyridin-3-yl)-phenyl, or 4-(pyridin-4-yl)-phenyl, each of which is substituted by R61 on the pyridinyl moiety. A further embodiment of the compounds according to the present invention relates to those compounds of formula I, in which R6 is 3-(pyridin-3-yl)-phenyl or 4-(pyridin-3-yl)-phenyl, each of which is substituted by R61 on the pyridinyl moiety. A further embodiment of the compounds according to the present invention relates to those compounds of formula I, in which R6 is 3-[6-(R61)-pyridin-3-yl]-phenyl or 4-[6-(R61)-pyridin-3-yl]-phenyl. A further embodiment of the compounds according to the present invention relates to those compounds of formula I, in which R6 is 3-(pyridin-4-yl)-phenyl or 4-(pyridin-4-yl)-phenyl, each of which is substituted by R61 on the pyridinyl moiety. A further embodiment of the compounds according to the present invention relates to those compounds of formula I, in which R6 is 3-[2-(R61)-pyridin-4-yl]-phenyl or 4-[2-(R61)-pyridin-4-yl]-phenyl. A further embodiment of the compounds according to the present invention relates to those compounds of formula I, in which R6 is 1,1'-biphenyl-4-yl or 1,1'-biphenyl-3-yl, each of which is substituted by R61 on the terminal phenyl moiety. A further embodiment of the compounds according to the present invention relates to those compounds of formula I, in which R6 is 3'-(R61)-1,1'-biphenyl-4-yl, 4'-(R61)-1,1'-biphenyl-4-yl, 3'-(R61)-1,1'-biphenyl-3-yl or 4'-(R61)-1,1'-biphenyl-3-yl. A further embodiment of the compounds according to the present invention relates to those compounds of formula I, in which R6 is 3'-(R61)-1,1'-biphenyl-4-yl or 4'-(R61)-1,1'-biphenyl-4-yl. A further embodiment of the compounds according to the present invention relates to those compounds of formula I, in which R6 is 3'-(R61)-1,1'-biphenyl-3-yl or 4'-(R61)-1,1'-biphenyl-3-yl. A further embodiment of the compounds according to the present invention relates to those compounds of formula I, in which R6 is 4'-(R61)-1,1'-biphenyl-3-yl or 4'-(R61)-1,1'-biphenyl-4-yl.

A further embodiment of the compounds according to the present invention relates to those compounds of formula I, in which R6 is pyridinyl-thiophenyl, which is substituted by R61 on the pyridinyl moiety. A further embodiment of the compounds according to the present invention relates to those compounds of formula I, in which R6 is [2-(R61)-pyridin-4-yl]-thiophenyl, such as e.g. 5-[2-(R61)-pyridin-4-yl]-thiophen-2-yl. A further embodiment of the compounds according to the present invention relates to those compounds of formula I, in which R6 is [6-(R61)-pyridin-3-yl]-thiophenyl, such as e.g. 5-[6-(R61)-pyridin-3-yl]-thiophen-2-yl. A further embodiment of the compounds according to the present invention relates to those compounds of formula I, in which R6 is bipyridyl, which is substituted by R61 on the terminal pyridinyl moiety. A further embodiment of the compounds according to the present invention relates to those compounds of formula I, in which R6 is [2-(R61)-pyridin-4-yl]-pyridinyl, such as e.g. 2-[2-(R61)-pyridin-4-yl]-pyridin-4-yl or 6-[2-(R61)-pyridin-4-yl]-pyridin-3-yl. A further embodiment of the compounds according to the present invention relates to those compounds of formula I, in which R6 is [6-(R61)-pyridin-3-yl]-pyridinyl, such as e.g. 2-[6-(R61)-pyridin-3-yl]-pyridin-4-yl or 6-[6-(R61)-pyridin-3-yl]pyridin-3-yl. A further embodiment of the compounds according to the present invention relates to those compounds of formula I, in which R6 is phenyl-thiophenyl, which is substituted by R61 on the phenyl moiety. A further embodiment of the compounds according to the present invention relates to those compounds of formula I, in which R6 is [3-(R61)-phenyl]-thiophenyl, such as e.g. 5-[3-(R61)-phenyl]-thiophen-2-yl. A further embodiment of the compounds according to the present invention relates to those compounds of formula I, in which R6 is [4-(R61)-phenyl]-thiophenyl, such as e.g. 5-[4-(R61)-phenyl]-thiophen-2-yl. A further embodiment of the compounds according to the present invention relates to those compounds of formula I, in which R6 is phenyl-pyridinyl, which is substituted by R61 on the phenyl moiety. A further embodiment of the compounds according to the present invention relates to those compounds of formula I, in which R6 is [3-(R61)-phenyl]-pyridinyl, such as e.g. 2-[3-(R61)-phenyl]-pyridin-4-yl or 6-[3-(R61)-phenyl]-pyridin-3-yl. A further embodiment of the compounds according to the present invention relates to those compounds of formula I, in which R6 is [4-(R61)-phenyl]-pyridinyl, such as e.g. 2-[4-(R61)-phenyl]-pyridin-4-yl or 6-[4-(R61)-phenyl]-pyridin-3-yl. A further embodiment of the compounds according to the present invention relates to those compounds of formula I, in which R6 is [1N-(1-4C-alkyl)-indolyl]-phenyl or [1N-(1-4C-alkyl)-pyrazolyl]-phenyl. A further embodiment of the compounds according to the present invention relates to those compounds of formula I, in which R6 is [1N-(1-2C-alkyl)-indol-5-yl]-phenyl or [1N-(1-2C-alkyl)-pyrazol-4-yl]-phenyl. A further embodiment of the compounds according to the present invention relates to those compounds of formula I, in which R6 is 3-(1N-methyl-pyrazol-4-yl)-phenyl or 4-(1N-methyl-pyrazol-4-yl)-phenyl. A further embodiment of the compounds according to the present invention relates to those compounds of formula I, in which R6 is [1N-(1-2C-alkyl)-pyrazol-4-yl]-pyridinyl, such as e.g. 2-(1N-methyl-pyrazol-4-yl)-pyridin-4-yl or 6-(1N-methyl-pyrazol-4-yl)-pyridin-3-yl. A further embodiment of the compounds according to the present invention relates to those compounds of formula I, in which R6 is triazolyl-phenyl, which is substituted by R61 on the triazolyl moiety. A further embodiment of the compounds according to the present invention relates to those compounds of formula I, in which R6 is {1N—(R61)-[1,2,3]triazol-4-yl}-phenyl, such as e.g. 3-{1N—(R61)-[1,2,3]triazol-4-yl}-phenyl or 4-{1N—(R61)-[1,2,3]triazol-4-yl}-phenyl. A further embodiment of the compounds according to the present invention relates to those compounds of formula I, in which R61 is -T2-N(R611)R612.

A further embodiment of the compounds according to the present invention relates to those compounds of formula I, in which T2 is a bond. A further embodiment of the compounds according to the present invention relates to those compounds of formula I, in which T2 is 1-4C-alkylene, such as e.g. 1-2C-alkylene. A further embodiment of the compounds according to the present invention relates to those compounds of formula I, in which T2 is methylene. A further embodiment of the compounds according to the present invention relates to those compounds of formula I, in which T2 is dimethylene.

A further embodiment of the compounds according to the present invention relates to those compounds of formula I, in which T2 is trimethylene. A further embodiment of the compounds according to the present invention relates to those compounds of formula I, in which R611 and R612 are both hydrogen.

A further embodiment of the compounds according to the present invention relates to those compounds of formula I, in which R611 and R612 are both methyl. A further embodiment of the compounds according to the present invention relates to those compounds of formula I, in which R611 and R612 together and with inclusion of the nitrogen atom, to which they are attached, form a morpholino ring. A further embodiment of the compounds according to the present invention relates to those compounds of formula I, in which R611 and R612 together and with inclusion of the nitrogen atom, to which they are attached, form a 4N-methyl-piperazino ring. A further embodiment of the compounds according to the present invention relates to those compounds of formula I, in which R611 and R612 together and with inclusion of the nitrogen atom, to which they are attached, form a pyrrolidino ring. A further embodiment of the compounds according to the present invention relates to those compounds of formula I, in which R611 and R612 together and with inclusion of the nitrogen atom, to which they are attached, form a piperidino ring. A further embodiment of the compounds according to the present invention relates to those compounds of formula I, in which R61 is —O-T3-N(R613)R614.

A further embodiment of the compounds according to the present invention relates to those compounds of formula I, in which T3 is dimethylene. A further embodiment of the compounds according to the present invention relates to those compounds of formula I, in which T3 is trimethylene.

A further embodiment of the compounds according to the present invention relates to those compounds of formula I, in which R613 and R614 are both methyl. A further embodiment of the compounds according to the present invention relates to those compounds of formula I, in which R613 and R614 together and with inclusion of the nitrogen atom, to which they are attached, form a morpholino ring. A further embodiment of the compounds according to the present invention relates to those compounds of formula I, in which R613 and R614 together and with inclusion of the nitrogen atom, to which they are attached, form a 4N-methyl-piperazino ring. A further embodiment of the compounds according to the present invention relates to those compounds of formula I, in which R613 and R614 together and with inclusion of the nitrogen atom, to which they are attached, form a pyrrolidino ring. A further embodiment of the compounds according to the present invention relates to those compounds of formula I, in which R613 and R614 together and with inclusion of the nitrogen atom, to which they are attached, form a piperidino ring.

A further embodiment of the compounds according to the present invention relates to those compounds of formula I, in which R61 is -T4-Het3, in which
T4 is a bond, methylene, dimethylene or trimethylene, and
Het3 is 1N-methyl-piperidin-4yl.

A further embodiment of the compounds according to the present invention relates to those compounds of formula I, in which R61 is —O-T5-Het4, in which
T5 is a bond, methylene, dimethylene or trimethylene, and
Het4 is 1N-methyl-piperidin-4yl.

A further embodiment of the compounds according to the present invention relates to those compounds of formula I, in which R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl; and R7 is hydroxyl.

A further embodiment of the compounds according to the present invention relates to those compounds of formula I, in which R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethyl-amino)methyl, aminomethyl, acetylamino-methyl, methylsulphonylamino-methyl, cyclopentylaminomethyl, cyclopropylaminomethyl and hydroxymethyl; and R7 is 2-aminophenyl.

A further embodiment of the compounds according to the present invention relates to those compounds of formula I, in which R6 is 4-(6-amino-pyridin-3-yl)-phenyl. A further embodiment of the compounds according to the present invention relates to those compounds of formula I, in which R6 is 4-[2-(4-methyl-piperazin-1-yl)-pyridin-4-yl)]-phenyl. A further embodiment of the compounds according to the present invention relates to those compounds of formula I, in which R6 is 3-[2-(4-methyl-piperazin-1-yl)-pyridin-4-yl)]-phenyl. A further embodiment of the compounds according to the present invention relates to those compounds of formula I, in which R6 is 4'-(2-morpholin-4-yl-ethyl)-biphenyl-3-yl. A further embodiment of the compounds according to the present invention relates to those compounds of formula I, in which R6 is 4'-dimethylaminomethyl-biphenyl-4-yl. A further embodiment of the compounds according to the present invention relates to those compounds of formula I, in which R6 is 5-[2-(4-methyl-piperazin-1-yl)-pyridin-4-yl)]-thiophen-2-yl. A further embodiment of the compounds according to the present invention relates to those compounds of formula I, in which R6 is 5-(4-dimethylaminomethyl-phenyl)-thiophen-2-yl.

A special embodiment of the compounds according to the present invention relates to those compounds of formula I, in which R1, R2, R3, R4 and R5 are all hydrogen, and R7 is hydroxyl. Another special embodiment of the compounds according to the present invention relates to those compounds of formula I, in which R1, R2, R3, R4 and R5 are all hydrogen, and R7 is 2-aminophenyl.

It is to be understood, that the present invention also includes any or all possible combinations and subsets of the embodiments defined herein afore.

Exemplary compounds according to this invention may include any one selected from 1. (E)-N-Hydroxy-3-{1-[4-(1-methyl-1H-indol-5-yl)-benzenesulfonyl]-1H-pyrrol-3-yl}-acrylamide,
2. (E)-N-Hydroxy-3-{1-[4-(1-methyl-1H-pyrazol-4-yl)-benzenesulfonyl]-1H-pyrrol-3-yl}-acrylamide,
3. (E)-N-Hydroxy-3-{1-[4-(6-methoxy-pyridin-3-yl)-benzenesulfonyl]-1H-pyrrol-3-yl}-acrylamide,
4. (E)-3-{1-[4-(6-Amino-pyridin-3-yl)-benzenesulfonyl]-1H-pyrrol-3-yl}-N-hydroxy-acrylamide,
5. (E)-N-(2-Amino-phenyl)-3-{1-[4-(6-methoxy-pyridin-3-yl)-benzenesulfonyl]-1H-pyrrol-3-yl}-acrylamide,
6. (E)-N-(2-Amino-phenyl)-3-{1-[4-(6-amino-pyridin-3-yl)-benzenesulfonyl]-1H-pyrrol-3-yl}-acrylamide,
7. (E)-N-(2-Amino-phenyl)-3-{1H-[4-(1-methyl-1H-pyrazol-4-yl)-benzenesulfonyl]-1H-pyrrol-3-yl}-acrylamide,
8. (E)-N-Hydroxy-3-{1-[4'-(2-morpholin-4-yl-ethyl)-biphenyl-4-sulfonyl]-1H-pyrrol-3-yl}-acrylamide,
9. (E)-N-Hydroxy-3-{1-[3'-(2-morpholin-4-yl-ethyl)-biphenyl-4-sulfonyl]-1H-pyrrol-3-yl}-acrylamide,
10. (E)-3-{1-[3-(6-Amino-pyridin-3-yl)-benzenesulfonyl]-1H-pyrrol-3-yl}-N-hydroxy-acrylamide,
11. (E)-N-Hydroxy-3-{1-[3-(6-methoxy-pyridin-3-yl)-benzenesulfonyl]-1H-pyrrol-3-yl}-acrylamide,
12. (E)-N-Hydroxy-3-{1H-[3-(1-methyl-1H-pyrazol-4-yl)-benzenesulfonyl]-1H-pyrrol-3-yl}-acrylamide,
13. (E)-N-Hydroxy-3-{1H-[3-(1-methyl-1H-indol-5-yl)-benzenesulfonyl]-1H-pyrrol-3-yl}-acrylamide,
14. (E)-N-(2-Amino-phenyl)-3-{1-[3-(6-methoxy-pyridin-3-yl)-benzenesulfonyl]-1H-pyrrol-3-yl}-acrylamide,
15. (E)-N-(2-Amino-phenyl)-3-{1H-[3-(1-methyl-1H-pyrazol-4-yl)-benzenesulfonyl]-1H-pyrrol-3-yl}-acrylamide,
16. (E)-N-Hydroxy-3-{1-[4'-(2-morpholin-4-yl-ethyl)-biphenyl-3-sulfonyl]-1H-pyrrol-3-yl}-acrylamide,
17. (E)-N-(2-Amino-phenyl)-3-{1-[3-(6-amino-pyridin-3-yl)-benzenesulfonyl]-1H-pyrrol-3-yl}-acrylamide,
18. (E)-N-(2-Amino-phenyl)-3-{1-[3'-(2-morpholin-4-yl-ethyl)-biphenyl-3-sulfonyl]-1H-pyrrol-3-yl}-acrylamide,
19. (E)-N-(2-Amino-phenyl)-3-{1-[4'-(2-morpholin-4-yl-ethyl)-biphenyl-3-sulfonyl]-1H-pyrrol-3-yl}-acrylamide,
20. (E)-N-Hydroxy-3-{1-[3'-(2-morpholin-4-yl-ethyl)-biphenyl-3-sulfonyl]-1H-pyrrol-3-yl}-acrylamide,
21. (E)-N-Hydroxy-3-[1-(2'-methanesulfonylamino-biphenyl-4-sulfonyl)-1H-pyrrol-3-yl]-acrylamide
22. (E)-N-hydroxy-3-[1-(3'-methanesulfonylamino-biphenyl-4-sulfonyl)-1H-pyrrol-3-yl]-acrylamide
23. (E)-N-Hydroxy-3-[1-(4'-methanesulfonylamino-biphenyl-4-sulfonyl)-1H-pyrrol-3-yl]-acrylamide
24. 4'-[3-((E)-2-Hydroxycarbamoyl-vinyl)-pyrrole-1-sulfonyl]-biphenyl-4-carboxylic acid (2-dimethylamino-ethyl)-amide,
25. 4'-[3-((E)-2-Hydroxycarbamoyl-vinyl)-pyrrole-1-sulfonyl]-biphenyl-3-carboxylic acid (2-dimethylamino-ethyl)-amide,
26. (E)-3-[1-(4'-Dimethylaminomethyl-biphenyl-4-sulfonyl)-1H-pyrrol-3-yl]-N-hydroxy-acrylamide,
27. (E)-3-[1-(2'-Dimethylaminomethyl-biphenyl-4-sulfonyl)-1H-pyrrol-3-yl]-N-hydroxy-acrylamide,
28. (E)-N-Hydroxy-3-(1-{4-[2-(4-methyl-piperazin-1-yl)-pyridin-4-yl]-benzenesulfonyl}-1H-pyrrol-3-yl)-acrylamide,
29. (E)-N-Hydroxy-3-{1-[4'-(toluene-4-sulfonylamino)-biphenyl-4-sulfonyl]-1H-pyrrol-3-yl}-acrylamide,
30. 3'-[3-((E)-2-Hydroxycarbamoyl-vinyl)-pyrrole-1-sulfonyl]-biphenyl-4-carboxylic acid (2-dimethylamino-ethyl)-amide,
31. (E)-N-Hydroxy-3-[1-(3'-morpholin-4-ylmethyl-biphenyl-3-sulfonyl)-1H-pyrrol-3-yl]-acrylamide,
32. (E)-N-Hydroxy-3-(1-{4'-[2-(4-methyl-piperazin-1-yl)-ethoxy]-biphenyl-3-sulfonyl}-1H-pyrrol-3-yl)-acrylamide,
33. (E)-N-Hydroxy-3-(1-{3-[2-(4-methyl-piperazin-1-yl)-pyridin-4-yl]-benzenesulfonyl}-1H-pyrrol-3-yl)-acrylamide,
34. (E)-N-Hydroxy-3-{1-[4'-(2-morpholin-4-yl-ethoxy)-biphenyl-3-sulfonyl]-1H-pyrrol-3-yl}-acrylamide,
35. (E)-N-(2-Amino-phenyl)-3-{1-[4-(1-benzyl-1H-pyrazol-4-yl)-benzenesulfonyl]-1H-pyrrol-3-yl}-acrylamide, 36. (E)-N-Hydroxy-3-[1-(4'-morpholin-4-ylmethyl-biphenyl-3-sulfonyl)-1H-pyrrol-3-yl]-acrylamide,
37. (E)-3-[1-(4'-Dimethylaminomethyl-biphenyl-3-sulfonyl)-1H-pyrrol-3-yl]-N-hydroxy-acrylamide,
38. (E)-N-Hydroxy-3-{1-[4'-(3-morpholin-4-yl-propoxy)-biphenyl-3-sulfonyl]-1H-pyrrol-3-yl}-acrylamide,
39. (E)-N-(2-Amino-phenyl)-3-[1-(4'-dimethylsulfamoyl-biphenyl-4-sulfonyl)-1H-pyrrol-3-yl]-acrylamide,
40. (E)-3-[1-(3'-Acetylamino-biphenyl-4-sulfonyl)-1H-pyrrol-3-yl]-N-(2-amino-phenyl)-acrylamide,
41. (E)-3-[1-(2'-Dimethylaminomethyl-biphenyl-3-sulfonyl)-1H-pyrrol-3-yl]-N-hydroxy-acrylamide,
42. (E)-N-Hydroxy-3-(1-{5-[2-(4-methyl-piperazin-1-yl)-pyridin-4-yl]-thiophene-2-sulfonyl}-1H-pyrrol-3-yl)-acrylamide,
43. (E)-N-Hydroxy-3-{1-[4'-(2-pyrrolidin-1-yl-ethoxy)-biphenyl-3-sulfonyl]-1H-pyrrol-3-yl}-acrylamide,
44. 4'-{3-[(E)-2-(2-Amino-phenylcarbamoyl)-vinyl]-pyrrole-1-sulfonyl}-biphenyl-3-carboxylic acid (2-dimethylamino-ethyl)-amide,
45. (E)-N-Hydroxy-3-{1-[4'-(3-morpholin-4-yl-propyl)-biphenyl-3-sulfonyl]-1H-pyrrol-3-yl}-acrylamide,
46. (E)-3-{1-[5-(4-Dimethylaminomethyl-phenyl)-thiophene-2-sulfonyl]-1H-pyrrol-3-yl}-N-hydroxy-acrylamide,
47. (E)-N-(2-Amino-phenyl)-3-[1-(4'-dimethylaminomethyl-biphenyl-4-sulfonyl)-1H-pyrrol-3-yl]-acrylamide,
48. (E)-N-(2-Amino-phenyl)-3-(1-{4-[2-(4-methyl-piperazin-1-yl)-pyridin-4-yl]-benzenesulfonyl}-1H-pyrrol-3-yl)-acrylamide,
49. (E)-3-[1-(4'-Acetylamino-biphenyl-4-sulfonyl)-1H-pyrrol-3-yl]-N-(2-amino-phenyl)-acrylamide,
50. (E)-N-Hydroxy-3-{1-[5-(3-morpholin-4-ylmethyl-phenyl)-thiophene-2-sulfonyl]-1H-pyrrol-3-yl}-acrylamide,
51. (E)-N-(2-Amino-phenyl)-3-[1-(3'-hydroxymethyl-biphenyl-4-sulfonyl)-1H-pyrrol-3-yl]-acrylamide,
52. (E)-N-(2-Amino-phenyl)-3-{1-[4-(3,5-dimethyl-isoxazol-4-yl)-benzenesulfonyl]-1H-pyrrol-3-yl}-acrylamide,
53. (E)-N-(2-Amino-phenyl)-3-[1-(4'-methanesulfonylamino-biphenyl-4-sulfonyl)-1H-pyrrol-3-yl]-acrylamide,
54. (E)-N-Hydroxy-3-{1-[5-(4-morpholin-4-ylmethyl-phenyl)-thiophene-2-sulfonyl]-1H-pyrrol-3-yl}-acrylamide,
55. (E)-N-Hydroxy-3-[1-(5-{4-[2-(4-methyl-piperazin-1-yl)-ethoxy]-phenyl}-thiophene-2-sulfonyl)-1H-pyrrol-3-yl]-acrylamide,
56. (E)-N-Hydroxy-3-(1-{5-[4-(2-morpholin-4-yl-ethoxy)-phenyl]-thiophene-2-sulfonyl}-1H-pyrrol-3-yl)-acrylamide,
57. (E)-N-Hydroxy-3-(1-{5-[4-(3-morpholin-4-yl-propoxy)-phenyl]-thiophene-2-sulfonyl}-1H-pyrrol-3-yl)-acrylamide,
58. (E)-N-Hydroxy-3-(1-{4'-[(2-methoxy-ethylamino)-methyl]-biphenyl-3-sulfonyl}-1H-pyrrol-3-yl)-acrylamide,
59. (E)-N-(2-Amino-phenyl)-3-[1-(3'-methanesulfonylamino-biphenyl-4-sulfonyl)-1H-pyrrol-3-yl]-acrylamide,
60. (E)-Hydroxy-3-{1-[5-(1-methyl-1H-pyrazol-4-yl)-thiophene-2-sulfonyl]-1H-pyrrol-3-yl}-acrylamide,
61. (E)-N-Hydroxy-3-(1-{5-[4-(2-morpholin-4-yl-ethyl)-phenyl]-thiophene-2-sulfonyl}-1H-pyrrol-3-yl)-acrylamide,
62. (E)-N-Hydroxy-3-{1-[4'-(4-methyl-piperazin-1-ylmethyl)-biphenyl-3-sulfonyl]-1H-pyrrol-3-yl}-acrylamide, and
63. (E)-3-[1-(4'-Cyclopropylaminomethyl-biphenyl-3-sulfonyl)-1H-pyrrol-3-yl]-N-hydroxy-acrylamide, and the salts thereof.

Further on, exemplary compounds according to this invention may also include any one selected from 64. (E)-N-Hydroxy-3-[1-(3'-morpholin-4-ylmethyl-biphenyl-4-sulfonyl)-1H-pyrrol-3-yl]-acrylamide,
65. (E)-3-[1-(4-Benzo[1,3]dioxol-5-yl-benzenesulfonyl)-1H-pyrrol-3-yl]-N-hydroxy-acrylamide,
66. (E)-3-[1-(3'-Amino-biphenyl-4-sulfonyl)-1H-pyrrol-3-yl]-N-hydroxy-acrylamide,
67. (E)-N-Hydroxy-3-[1-(4'-hydroxy-biphenyl-4-sulfonyl)-1H-pyrrol-3-yl]-acrylamide,
68. (E)-N-Hydroxy-3-(1-{4'-[2-(1-methyl-piperidin-4-yl)-ethoxy]-biphenyl-4-sulfonyl}-1H-pyrrol-3-yl)-acrylamide,
69. (E)-3-[1-(3'-Dimethylamino-biphenyl-4-sulfonyl)-1H-pyrrol-3-yl]-N-hydroxy-acrylamide,
70. (E)-3-{1-[4-(2,3-Dihydro-benzofuran-5-yl)-benzenesulfonyl]-1H-pyrrol-3-yl}-N-hydroxy-acrylamide,
71. (E)-N-Hydroxy-3-[1-(4'-morpholin-4-yl-biphenyl-4-sulfonyl)-1H-pyrrol-3-yl]-acrylamide,
72. (E)-N-Hydroxy-3-{1-[3'-(3-pyrrolidin-1-yl-propoxy)-biphenyl-4-sulfonyl]-1H-pyrrol-3-yl}-acrylamide,
73. (E)-N-Hydroxy-3-(1-{3'-[3-(4-methyl-piperazin-1-yl)-propoxy]-biphenyl-4-sulfonyl}-1H-pyrrol-3-yl)-acrylamide,
74. (E)-N-Hydroxy-3-{1-[3'-(3-morpholin-4-yl-propoxy)-biphenyl-4-sulfonyl]-1H-pyrrol-3-yl}-acrylamide,
75. (E)-N-Hydroxy-3-[1-(3'-morpholin-4-ylmethyl-biphenyl-4-sulfonyl)-1H-pyrrol-3-yl]-acrylamide,
76. (E)-N-Hydroxy-3-(1-{4'-[2-(4-methyl-piperazin-1-yl)-ethoxy]-biphenyl-4-sulfonyl}-1H-pyrrol-3-yl)-acrylamide,
77. (E)-N-Hydroxy-3-{1-[4'-(2-morpholin-4-yl-ethoxy)-biphenyl-4-sulfonyl]-1H-pyrrol-3-yl}-acrylamide,
78. (E)-N-Hydroxy-3-{1-[4'-(3-morpholin-4-yl-propoxy)-biphenyl-4-sulfonyl]-1H-pyrrol-3-yl}-acrylamide,
79. (E)-N-Hydroxy-3-(1-{4'-[3-(4-methyl-piperazin-1-yl)-propoxy]-biphenyl-4-sulfonyl}-1H-pyrrol-3-yl)-acrylamide,
80. (E)-N-Hydroxy-3-{1-[3'-(2-pyrrolidin-1-yl-ethoxy)-biphenyl-4-sulfonyl]-1H-pyrrol-3-yl}-acrylamide,
81. (E)-N-Hydroxy-3-{1-[4'-(3-pyrrolidin-1-yl-propoxy)-biphenyl-4-sulfonyl]-1H-pyrrol-3-yl}-acrylamide,
82. (E)-N-Hydroxy-3-[1-(4'-methoxy-biphenyl-4-sulfonyl)-1H-pyrrol-3-yl]-acrylamide,
83. (E)-N-Hydroxy-3-(1-{4-[1-(2-morpholin-4-yl-ethyl)-1H-[1,2,3]triazol-4-yl]-benzenesulfonyl}-1H-pyrrol-3-yl)-acrylamide,
84. (E)-3-[1-(4'-Cyclopentylaminomethyl-biphenyl-4-sulfonyl)-1H-pyrrol-3-yl]-N-hydroxy-acrylamide,
85. (E)-N-Hydroxy-3-[1-(3'-trifluoromethyl-biphenyl-4-sulfonyl)-1H-pyrrol-3-yl]-acrylamide,
86. (E-3-{1-[5-(3-Dimethylaminomethyl-phenyl)-thiophene-2-sulfonyl]-1H-pyrrol-3-yl}-N-hydroxy-acrylamide,
87. (E)-3-[1-(3'-Dimethylaminomethyl-biphenyl-3-sulfonyl)-1H-pyrrol-3-yl]-N-hydroxy-acrylamide,
88. (E)-N-Hydroxy-3-{1-[4'-(2-morpholin-4-yl-ethyl)-biphenyl-3-sulfonyl]-1H-pyrrol-3-yl}-acrylamide,
89. (E)-N-(2-Amino-phenyl)-3-{1-[6-(4-dimethylaminomethyl-phenyl)-pyridine-3-sulfonyl]-1H-pyrrol-3-yl}-acrylamide,
90. (E)-N-Hydroxy-3-{1-[5-(2-methyl-thiazol-4-yl)-thiophene-2-sulfonyl]-1H-pyrrol-3-yl}-acrylamide, 91. (E)-3-[1-(4'-Aminomethyl-biphenyl-3-sulfonyl)-1H-pyrrol-3-yl]-N-hydroxy-acrylamide,
92. (E)-N-Hydroxy-3-(1-{6-[4-(2-pyrrolidin-1-yl-ethoxy)-phenyl]-pyridine-3-sulfonyl}-1H-pyrrol-3-yl)-acrylamide,
93. (E)-3-[1-(4'-Aminomethyl-biphenyl-4-sulfonyl)-1H-pyrrol-3-yl]-N-(2-amino-phenyl)-acrylamide,
94. (E)-3-{1-[5-(3-Aminomethyl-phenyl)-thiophene-2-sulfonyl]-1H-pyrrol-3-yl}-N-hydroxy-acrylamide,
95. (E)-N-(2-Amino-phenyl)-3-{1-[5-(4-dimethylaminomethyl-phenyl)-thiophene-2-sulfonyl]-1H-pyrrol-3-yl}-acrylamide,
96. (E)-N-(2-Amino-phenyl)-3-[1-(3'-dimethylaminomethyl-biphenyl-4-sulfonyl)-1H-pyrrol-3-yl]-acrylamide,
97. (E)-3-{1-[4'-(Acetylamino-methyl)-biphenyl-4-sulfonyl]-1H-pyrrol-3-yl}-N-(2-amino-phenyl)-acrylamide,
98. (E)-N-(2-Amino-phenyl)-3-{1-[4'-(methanesulfonylamino-methyl)-biphenyl-4-sulfonyl]-1H-pyrrol-3-yl}-acrylamide,
99. (E)-N-Hydroxy-3-(1-{5-[4-(2-pyrrolidin-1-yl-ethoxy)-phenyl]-thiophene-2-sulfonyl}-1H-pyrrol-3-yl)-acrylamide,
100. (E)-3-{1-[5-(4-Dimethylsulfamoyl-phenyl)-thiophene-2-sulfonyl]-1H-pyrrol-3-yl}-N-hydroxy-acrylamide,
101. (E)-N-(2-Amino-phenyl)-3-[1-(4'-methanesulfonylamino-biphenyl-3-sulfonyl)-1H-pyrrol-3-yl]-acrylamide,
102. (E)-N-(2-Amino-phenyl)-3-[1-(4'-dimethylaminomethyl-biphenyl-3-sulfonyl)-1H-pyrrol-3-yl]-acrylamide,
103. (E)-N-Hydroxy-3-{1-[2'-(4-methyl-piperazin-1-yl)-[2,4']bipyridinyl-5-sulfonyl]-1H-pyrrol-3-yl}-acrylamide,
104. (E)-N-(2-Amino-phenyl)-3-{1-[5-(1-methyl-1H-pyrazol-4-yl)-thiophene-2-sulfonyl]-1H-pyrrol-3-yl}-acrylamide,
105. (E)-3-{1-[6-(4-Dimethylaminomethyl-phenyl)-pyridine-3-sulfonyl]-1H-pyrrol-3-yl}-N-hydroxy-acrylamide,
106. (E)-N-(2-Amino-phenyl)-3-(1-{5-[2-(4-methyl-piperazin-1-yl)-pyridin-4-yl]-thiophene-2-sulfonyl}-1H-pyrrol-3-yl)-acrylamide,
107. (E)-N-(2-Amino-phenyl)-3-[1-(4'-morpholin-4-ylmethyl-biphenyl-4-sulfonyl)-1H-pyrrol-3-yl]-acrylamide,
108. (E)-N-(2-Amino-phenyl)-3-{1-[4'-(2-pyrrolidin-1-yl-ethoxy)-biphenyl-4-sulfonyl]-1H-pyrrol-3-yl}-acrylamide,
109. (E)-N-Hydroxy-3-(1-{4-[1-(2-piperidin-1-yl-ethyl)-1H-[1,2,3]triazol-4-yl]-benzenesulfonyl}-1H-pyrrol-3-yl)-acrylamide,
110. (E)-3-[1-(3'-Dimethylaminomethyl-biphenyl-3-sulfonyl)-1H-pyrrol-3-yl]-N-hydroxy-acrylamide,
111. (E)-N-(2-Amino-phenyl)-3-(1-{5-[4-(methynesulfonylamino-methyl)-phenyl]-thiophene-2-sulfonyl}-1H-pyrrol-3-yl)-acrylamide,
112. (E)-N-(2-Amino-phenyl)-3-{1-[3'-(methanesulfonylamino-methyl)-biphenyl-3-sulfonyl]-1H-pyrrol-3-yl}-acrylamide,
113. (E)-3-(1-{5-[4-(Acetylamino-methyl)-phenyl]-thiophene-2-sulfonyl}-1H-pyrrol-3-yl)-N-(2-amino-phenyl)-acrylamide,
114. (E)-N-(2-Amino-phenyl)-3-{1-[5-(3-dimethylaminomethyl-phenyl)-thiophene-2-sulfonyl]-1H-pyrrol-3-yl}-acrylamide,
115. (E)-N-(2-Amino-phenyl)-3-[1-(3'-dimethylaminomethyl-biphenyl-3-sulfonyl)-1H-pyrrol-3-yl]-acrylamide,
116. (E)-3-[1-(3'-Dimethylaminomethyl-biphenyl-4-sulfonyl)-1H-pyrrol-3-yl]-N-hydroxy-acrylamide,
117. (E)-3-{1-[5-(3-Dimethylaminomethyl-phenyl)-thiophene-2-sulfonyl]-1H-pyrrol-3-yl}-N-hydroxy-acrylamide,
118. (E)-3-{1-[3'-(Acetylamino-methyl)-biphenyl-3-sulfonyl]-1H-pyrrol-3-yl}-N-(2-amino-phenyl)-acrylamide,
119. (E)-N-(2-Amino-phenyl)-3-{1-[6-(1-methyl-1H-pyrazol-4-yl)-pyridine-3-sulfonyl]-1H-pyrrol-3-yl}-acrylamide,
120. (E)-N-Hydroxy-3-{1-[6-(1-methyl-1H-pyrazol-4-yl)-pyridine-3-sulfonyl]-1H-pyrrol-3-yl}-acrylamide, and
121. (E)-3-{1-[6-(3-Dimethylaminomethyl-phenyl)-pyridine-3-sulfonyl]-1H-pyrrol-3-yl}-N-hydroxy-acrylamide, and the salts thereof.

In an embodiment of the foregoing, exemplary compounds according to this invention may especially include any one selected from the group consisting of the compounds 2, 4, 7, 16, 26, 28, 32, 33, 38, 42 and 46 as mentioned afore, and the salts thereof.

As used herein, 4SC-202 and (E)-N-(2-aminophenyl)-3-(1-((4-(1-methyl-1H-pyrazol-4-yl)phenyl)sulfonyl)-1H-pyrrol-3-yl)acrylamide (its chemical name) are used interchangeably and both refer to a compound of the following formula:

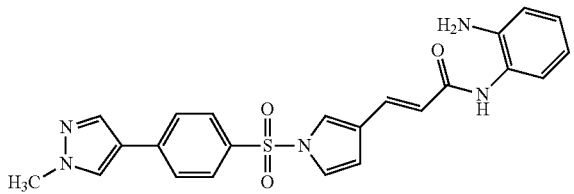 [SMILES: Cn1cc(-c2ccc(S(=O)(=O)n3ccc(/C=C/C(=O)Nc4ccccc4N)c3)cc2)cn1]

Suitable salts for the HDAC inhibitor are acid addition salts or salts with bases. Particular mention may be made of the pharmacologically tolerable inorganic and organic acids and bases customarily used in pharmacy. Those suitable are, on the one hand, water-insoluble and, particularly, water-soluble acid addition salts, the acids being employed in salt preparation in an equimolar quantitative ratio or one differing therefrom, particularly in an equimolar quantitative ratio. On the other hand, salts with bases are—depending on substitution—also suitable, the bases being employed in salt preparation in an equimolar quantitative ratio or one differing therefrom. Pharmacologically intolerable salts, which can be obtained, for example, as process products during the preparation of the HDAC inhibitor on an industrial scale, are converted into pharmacologically tolerable salts by processes known to the person skilled in the art. According to the invention, the HDAC inhibitor as well as its salts may contain, e.g. when isolated in crystalline form, varying amounts of solvents. Included within the scope of the present invention are therefore all solvates and in particular all hydrates of the HDAC inhibitor as well as all solvates and in particular all hydrates of the HDAC inhibitor, in particular such solvates or hydrates comprising about 0.5, 1 or 2 solvate or water molecules per molecule of the HDAC inhibitor or salts thereof.

Particular salts in the context of the present invention are the salts of 4SC-202 with, HBr, methansulfonic acid, hemiethane-1,2-disulfonic acid, benzenesulfonic acid, toluenesulfonic acid and 2-naphthalenesulfonic acid, more particularly toluenesulfonic acid, in particular in a molar ratio of about 1:1.

The HDAC inhibitor, in particular 4SC-202 and salts thereof can be prepared, for example, as described in detail in WO 2006/097474 A1 and WO 2009/112522 A1, respectively.

The ability of CD137 agonists which are biologicals, e.g. antibodies, to bind to CD137 can be assessed by in vitro/in vivo and/or cell-based assays either using purified domains of the target proteins or cells using ELISA or flow cytometry methods with a wide array of assays, e.g. the ELISA assay as described herein.

Urelumab (BMS-663513) is a humanized agonistic monoclonal IgG4 with a hinge mutation (S228P) antibody. At the determined maximum tolerated dose of 0.1 mg/kg every 3 weeks, urelumab was relatively well tolerated, with fatigue (16%) and nausea (13%) being the most common treatment-related AEs, and was associated with immunologic and pharmacodynamic activity demonstrated by the induction of IFN-inducible genes and cytokines (Segal et al, 2017, Clinical Cancer Research, 23, 1929-1936).

Utomilumab (PF-05082566) is a fully human IgG2 mAb agonist of the T-cell costimulatory receptor 4-1BB/CD137.

The biological and medicinal properties of the HDAC inhibitor according to the present invention, in particular 4SC-202, and its respective salts, as well as for the CD137 agonists, are described in detail in the prior art, including but not limited to the references cited herein.

In certain embodiments of the present invention, the HDAC inhibitor and the CD137 agonist may be administered simultaneously, sequentially or separately.

Administration of the HDAC inhibitor may in certain embodiments be within 30 minutes after a breakfast or light breakfast or within 30 minutes after a dinner or light dinner.

In the further context of the present invention, the term "active agents" refers to a pharmaceutical agent exerting a medical effect on a disease or medical condition (e.g. an amelioration thereof) and said term in particular includes the HDAC inhibitor and the CD137 agonist, such as 4SC-202 and Urelumab.

In the embodiments of the present invention, the active agents may be provided in pharmaceutical compositions comprising one or more of said active agents and a pharmaceutically acceptable carrier or diluent. In particular, the HDAC inhibitor and the CD137 agonist may be provided in separate pharmaceutical.

Such pharmaceutical compositions may be provided in the context of pharmaceutical products, comprising e.g. one or more pharmaceutical compositions and packaging material. Said packaging material typically comprises a label or package insert which indicates that the active agent(s) is/are useful for treating the diseases detailed herein. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the active agents are either employed as such, or particularly in combination with suitable pharmaceutical auxiliaries and/or excipients, e.g. in the form of tablets, coated tablets, capsules, caplets, suppositories, patches (e.g. as TTS), emulsions, suspensions, gels or solutions, the active agent content advantageously being between 0.1 and 95% and where, by the appropriate choice of the auxiliaries and/or excipients, a pharmaceutical administration form (e.g. a delayed release form or an enteric form) exactly suited to the active agent and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other excipients, for example antioxidants, dispersants, emulsifiers, preservatives, solubilizers, colorants, complexing agents or permeation promoters, can be used.

In practicing the present invention and depending on the details, characteristics or purposes of their uses mentioned above, the active agents according to the present invention may be administered in combination therapy separately, sequentially, simultaneously or chronologically staggered (e.g. as combined unit dosage forms (in the case of the CD137 agonist being orally available, e.g. small molecules)), as separate unit dosage forms or adjacent discrete unit dosage forms, as fixed (in the case of the CD137 agonist being orally available, e.g. small molecules) or non-fixed combinations, as kit-of-parts or as admixtures (in the case of the CD137 agonist being orally available, e.g. small molecules)).

A "fixed combination" is defined as a combination wherein a first active ingredient and at least one further active ingredient are present together in one unit dosage or in a single entity (in the case of the CD137 agonist being orally available, e.g. small molecules). One example of a "fixed combination" is a pharmaceutical composition wherein the said first active ingredient and said further active ingredient are present in admixture for simultaneous administration, such as in a single formulation. Another example of a "fixed combination" is a pharmaceutical combination wherein the said first active ingredient and the said further active ingredient are present in one unit without being in admixture.

A "kit-of-parts" is defined as a combination wherein the said first active ingredient and the said further active ingredient are present in more than one unit. One example of a "kit-of-parts" is a combination wherein the said first active ingredient and the said further active ingredient are present separately. The components of the kit-of-parts may be administered separately, sequentially, simultaneously or chronologically staggered.

The first and further active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and further active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. parenteral, in particular intravenous administration.

A further aspect of the present invention is a combination comprising, in non-fixed form, the HDAC inhibitor and one or more further therapeutic agents for sequential, separate, simultaneous or chronologically staggered use in therapy in any order. Optionally said combination comprises instructions for its use in therapy.

A further aspect of the present invention is a combined preparation, such as e.g. a kit of parts, comprising a preparation of the HDAC inhibitor and a pharmaceutically acceptable carrier or diluent and one or more further therapeutic agents; and optionally instructions for simultaneous, sequential, separate or chronologically staggered use in therapy.

A further aspect of the present invention is a kit of parts comprising a dosage unit of the HDAC inhibitor, a dosage unit of one or more further therapeutic agents, and optionally instructions for simultaneous, sequential or separate use in therapy.

A further aspect of the present invention is a pharmaceutical product comprising the HDAC inhibitor, or one or more pharmaceutical compositions comprising said compounds; and one or more further therapeutic agents, or one or more pharmaceutical compositions comprising said therapeutic agents, for simultaneous, sequential or separate use in therapy. Optionally this pharmaceutical product comprises instructions for use in said therapy.

A further aspect of the present invention is a pharmaceutical composition as unitary dosage form comprising, in admixture, the HDAC inhibitor one or more further therapeutic agents and optionally a pharmacologically acceptable carrier, diluent or excipient.

A further aspect of the present invention is a commercial package comprising the HDAC inhibitor together with instructions for simultaneous, sequential or separate use with one or more further therapeutic agents.

In addition, the combination according to the present invention can be used in the pre- or post-surgical treatment.

In further addition, the combination according to the present invention can be used in combination with radiation therapy, in particular in sensitization of patients towards standard radiation therapy.

The administration of the combination according to the present invention and pharmaceutical compositions according to the invention may be performed in any of the generally accepted modes of administration available in the art. Illustrative examples of suitable modes of administration include intravenous, oral, nasal, parenteral, topical, transdermal and rectal delivery. In a particular embodiment of the present invention, the administration of the HDAC inhibitor is via oral delivery and the administration of the CD137 agonist is parenteral, in particular intravenous in the case of a biological, via oral delivery, e.g. in the case of a small molecule.

In the embodiments of the present invention, doses refer to the amount of compound with respect to the free form of said compound, i.e. the free acid or free base form of said compound. Consequently, adducts, salts, etc. of such free acid or free base form are actually to be administered in a correspondingly higher dose in order to account for the weight of the counter-ion or adduct partner. For example, in relation to 4SC-202 tosylate salt, a "dose of 100 mg 4SC-202" relates to (rounded) 138 mg 4SC-202 tosylate salt—comprising 100 mg 4SC-202 free base and 38 mg toluenesulfonic acid (molecular weight of 4SC-202=447.513 g/mol; molecular weight of 4SC-202 tosylate salt=619.711 g/mol; therefore 100:447.513*619.711=138).

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicit, implicit or inherent disclosure) of the present invention without departing from the spirit and scope of this invention as defined by the scope of the appended claims.

As used herein, the term including, unless specified otherwise, is to be understood to mean "including, but not limited to".

As used herein, expressions such as "is/are administered" likewise refer to "is/are to be administered".

As used herein, treatment of cancer may likewise refer to treatment of a subject suffering from cancer, e.g. a human subject suffering from cancer, or a cancer patient.

In the present invention, the administration of active agents may follow a certain schedule, which may include periods of daily administration of active agents and periods wherein only one of the active agents or no active agents are administered. Particularly, such a schedule consists of treatment cycles, wherein typically such treatment cycles can be repeated as often as necessary, i.e. as seen fit by the physician responsible for the treatment.

Treatment cycles are particularly 12-16 day treatment cycles, 2 week treatment cycles, 17-25 day treatment cycles, 3 week treatment cycles, 24-32 day treatment cycles, 4 week treatment cycles, 30-40 day treatment cycles, 5 week treatment cycles, 37-47 day treatment cycles, or 6 week treatment cycles, more particularly 2 week, 3 week, 4 week, 5 week, or 6 week treatment cycles, even more particularly 2 week, 3 week, or 4 week treatment cycles, yet even more particularly 2 week or 3 week treatment cycles, yet even more particularly 3 week treatment cycles.

Typically, in the case of the CD137 agonist(s) being biologicals, they are administered only on day one of each treatment cycle. The treatment cycle then follows the usual administration cycle of the CD137 agonist(s), e.g. as typically applied by physicians and/or as approved by the governmental authorities. In the case of the CD137 agonist(s) being orally available, e.g. small molecules, they typically can be administered following the administration schedule of the HDAC inhibitor or continuously, or following a different pattern, e.g. a different pattern of the ones described herein for the HDAC inhibitor (e.g. the HDAC inhibitor being dosed every other day and the orally available CD137 agonist being administered daily.

In particular embodiments the treatment may involve a first treatment cycle, wherein only the HDAC inhibitor in administered, (i.e. no CD137 agonist is administered). Said first treatment cycle is then followed by the treatment with the combination of the CD137 agonist and the HDAC inhibitor as detailed herein. Said treatment cycle may otherwise (except for the administration of the CD137 agonist) be equal in duration and dosing of the HDAC inhibitor to the treatment cycle as described herein.

In certain embodiments, in each treatment cycle, the HDAC inhibitor may be administered for a certain number of days, followed by a number of days wherein no HDAC inhibitor is administered. In particular embodiments, the HDAC inhibitor is administered daily for 14 days in a three-week treatment cycle, or daily for 7 days in a two-week treatment cycle, in each case followed by 7 days wherein no HDAC inhibitor is administered.

In other particular embodiments, the HDAC inhibitor is administered continuously, i.e. the daily dose is administered every day during the duration of the treatment.

In particular embodiments, Urelumab is administered on day 1 of a three-week treatment cycle, in particular in a dose of about 0.1 mg/kg.

References and claims to the use of a certain compound for the manufacture of a medicament for the treatment of cancer in to be used combination with a certain second agent in their general and specific forms likewise relate to:

a) the use of said compound for the manufacture of a medicament for the treatment of cancer in combination with said second agent;
b) methods of treating said disease or medical condition, said method comprising administering a therapeutically effective and tolerable amount of said certain compound to a subject in need thereof, and administering a therapeutically effective and tolerable amount of said second agent to said subject;
c) methods of treating said disease or medical condition, said method comprising administering a therapeutically effective and tolerable amount of said certain compound to a subject in need thereof, said certain compound to be used in combination with said second agent;
d) compositions comprising said certain compound for the treatment of said disease or medical condition in combination with said second agent;
e) compositions comprising said certain compound for the treatment of said disease or medical condition, said composition to be used in combination with said second agent; to said certain compound for use in the treatment of said disease or medical condition in combination with said second agent;
f) said certain compound for use in the treatment of said disease or medical condition to be used in combination with said second agent;

and vice versa.

EXAMPLES

The following examples serve to illustrate the invention further without restricting it.

Materials and Methods 1.1. Test Substances
  4SC-202 (tosylate salt).
  Anti-CD137 (4-1BB) antibody (clone: LOB12.3, catalog: BE0169, isotype: Rat IgG1, Bioxcell),
1.2. Vehicles
  4SC-202 was suspended in 2% methocel solution at 2 mg/ml (active compound).
  Anti-CD137 antibody was diluted with PBS in order to reach final concentration of 1 mg/ml.
1.3. Treatment Doses
  4SC-202 was administered at 20 mg/kg twice daily, based on 4SC-202 free base.
  The anti-CD137 antibody was injected at 10 mg/kg,
1.4. Routes of Administration
  4SC-202 was administered by oral gavage (per os, PO) via a gavage tube.
  The anti-CD137 antibody was injected intraperitoneally into the peritoneal cavity of mice.
  In all cases, the administration volume was 10 mL/kg adjusted to the most recent individual body weight of mice.

1.5. Cancer Cell Line and Culture Conditions
1.5.1. Cancer Cell Line
  Colon 38 (C38, a C57BU6J mouse colon adenocarcinoma cell line) tumor fragments.
1.5.2. In Vivo Tumor Amplification
  The C38 fragments are stored frozen in DMSO/SVF/RPMI 1640 medium (10/10/80) in liquid nitrogen until use. In the study part 1, C38 frozen fragments were thawed at 37° C. for 5 min, rinsed twice in RPMI 1640 medium before subcutaneous (SC) implantation in mice.
1.6. Use of Animals
1.6.1. Animals
  Animals were maintained in SPF health status according to the FELASA guidelines,
  Animal housing and experimental procedures were realized according to the French and European Regulations and NRC Guide for the Care and Use of Laboratory Animals [2, 3],
  Animals were individually identified with RFID transponder,
  Each cage was labeled with a specific code.
1.6.2. Housing Conditions [2, 3]
  Animals were maintained in housing rooms under controlled environmental conditions:
  Temperature: 22±2° C.,
  Humidity 55±10%,
  Photoperiod (12 h light/12 h dark),
  HEPA filtered air,
  15 air exchanges per hour with no recirculation.
  Animal enclosures provided sterile and adequate space with bedding material, food and water, environmental and social enrichment (group housing): Top filter polycarbonate Eurostandard Type III or IV cages; Corn cob bedding (ref: LAB COB 12, SERLAB, France); 25 kGy Irradiated diet (Ssniff® Soest, Germany); Complete food for immunodeficient rodents—NM Extrudate; Complete food for immunocompetent rodents—R/M-H Extrudate; Sterile, filtrated at 0.2 µm water; Environmental enrichment (SIZZLE-dri kraft—D20004 SERLAB, France).
1.6.3. Induction of C38 Tumors in Animals
  Thirty-five (35) female C57BL/6J mice were subcutaneously implanted into the right flank with C38 tumor fragments. When tumor volumes reached 500-1000 mm³, tumors were surgically excised and tumor fragments (30-50 mg) were subcutaneously implanted into the right flank of 224 female C57BL/6J mice at DO.
1.6.4. Treatment Schedule
  The treatment started when the tumors reached a mean volume of 100-200 mm³ (day 10). Animals were randomized according to their individual tumor volume into groups each of 20 animals using Vivo Manager® software (Biosystemes, Couternon, France). A statistical test (analysis of variance, ANOVA) was performed to test for homogeneity between groups. The treatment schedule was chosen as follows:
  Animals from group 1 received twice daily PO administrations of vehicle for 24 consecutive days (2Q1 D×24). The bi-daily treatments were separated by a 12-hour period,
  Animals from group 2 received twice daily PO administrations of 4SC-202 at 20 mg/kg for 24 consecutive days (2Q1 D×24). The bi-daily treatments were separated by a 12-hour period,
  Animals from group 3 received one IP injection of anti-CD137 antibody at 10 mg/kg every 3 days four times (Q3D×4),
  Animals from group 4 received one IP injection of anti-CD137 antibody at 10 mg/kg every 3 days four times (Q3D×4) in combination with twice daily PO administrations of 4SC-202 at 20 mg/kg for 24 consecutive days (2Q1 D×24). The bi-daily treatments were separated by a 12-hour period. The anti-CD137 antibody treatments were performed 6 hours after the 4SC-202 morning treatment, 1.6.5. Mice Termination and Tumor Collection Ten mice in each group were terminated at D28. The day of termination the mice treated with 4SC-202 received only the morning treatment.

1.6.6. Tumor and Clinical Monitoring

All study data, including animal body weight measurements, tumor volume, clinical and mortality records, and treatment were scheduled and recorded on Vivo Manager® database (Biosystemes, Dijon, France).

The viability and behavior were recorded every day. Body weights were measured twice a week. The length and width of the tumor were measured twice a week with calipers and the volume of the tumor were estimated by the formula:

Tumor Volume=width$^2$×length/2

The data demonstrates that the combination of 4SC-202 with a CD137 agonist (group d) results in a stronger and significant tumor control, compared with mono-therapy with either 4SC-202 (group d) or CD137 agonist (group c) alone (FIG. 1A, box plot shown for day 27 data, includes all data points with median and 25/75 percentiles, whiskers indicate min to max, + indicates the mean value—Statistics: Kruscal-Wallis test, p=0.0027 () for anti-CD137, p<0.0001 (**) for combination of anti-CD137 and 4SC-202). Analysis of the individual curves for the animals in each group reveals that whereas anti-CD137 antibody alone (group c) resulted in regress of some tumors (7 of 20), the combination (group d) induced regression and remission of tumors in significantly more animals (15 of 20) (FIG. 1B). Data past day 27 not shown.

In summary, the combination of the HDAC inhibitor 4SC-202 and a CD137 agonist unexpectedly showed significant tumor shrinkage and even remission in most test subjects, whereas each compound taken alone did not.

The invention claimed is:

1. A method for the treatment of cancer comprising administering to a subject in need thereof an effective amount of an HDAC inhibitor of formula I or a salt or solvate thereof in combination with a CD137 agonist, formula I

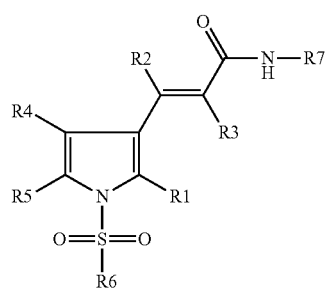

(I)

in which
R1, R4 and R5 are independently hydrogen, 1-4C-alkyl, halogen, or 1-4C-alkoxy,
R2 and R3 are independently hydrogen or 1-4C-alkyl,
R6 is -T1-Q1, in which T1 is a bond or 1-4C-alkylene,
either Q1 is substituted by R61 and/or R62, and is Aa1, Hh1, Ha1, Ha2, Ha3, Ha4 or Ah1, or Q1 is unsubstituted, and is Ha2, Ha3 or Ha4,
in which
R61 is 1-4C-alkyl, phenyl-1-4C-alkyl, 1-4C-alkoxy, hydroxyl, trifluoromethyl, cyano, halogen, completely fluorine-substituted 1-4C-alkoxy or 1-4C-alkoxy wherein more than half of the hydrogen atoms are replaced by fluorine atoms, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, -U-T3-N(R613)R614, -T4-Het3, or -V-T5-Het4, in which
T2 is a bond or 1-4C-alkylene,
R611 is hydrogen, 1-4C-alkyl, 3-7C-cycloalkyl, 3-7C-cycloalkylmethyl, hydroxy-2-4C-alkyl, 1-4C-alkoxy-2-4C-alkyl, 1-4C-alkylcarbonyl, or 1-4C-alkylsulphonyl,
R612 is hydrogen or 1-4C-alkyl,
or R611 and R612 together and with inclusion of the nitrogen atom, to which they are bonded, form a heterocyclic ring Het1, in which Het1 is morpholino, thiomorpholino, S-oxo-thiomorpholino, S,S-dioxo-thiomorpholino, piperidino, pyrrolidino, piperazino, or 4N-(1-4C-alkyl)-piperazino,
U is —O-(oxygen) or —C(O)NH—,
T3 is 2-4C-alkylene,
R613 is hydrogen, 1-4C-alkyl, 3-7C-cycloalkyl, 3-7C-cycloalkylmethyl, hydroxy-2-4C-alkyl or 1-4C-alkoxy-2-4C-alkyl, 1-4C-alkylcarbonyl, or 1-4C-alkylsulphonyl
R614 is hydrogen or 1-4C-alkyl,
or R613 and R614 together and with inclusion of the nitrogen atom, to which they are bonded, form a heterocyclic ring Het2, in which
Het2 is morpholino, thiomorpholino, S-oxo-thiomorpholino, S,S-dioxo-thiomorpholino, piperidino, pyrrolidino, piperazino, or 4N-(1-4C-alkyl)-piperazino,
T4 is a bond or 1-4C-alkylene,
Het3 is 1N-(1-4C-alkyl)-piperidinyl or 1N-(1-4C-alkyl)-pyrrolidinyl,
V is —O-(oxygen) or —C(O)NH—,
T5 is a bond or 1-4C-alkylene,
Het4 is 1N-(1-4C-alkyl)-piperidinyl or 1N-(1-4C-alkyl)-pyrrolidinyl,
R62 is 1-4C-alkyl, 1-4C-alkoxy or halogen,
Aa1 is a bisaryl radical made up of two aryl groups,
which are selected independently from a group consisting of phenyl and naphthyl, and
which are linked together via a single bond,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond,
Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, wherein said aryl and heteroaryl groups are linked together via a single bond, and wherein Ah1 is bonded via said heteroaryl moiety to the parent molecular group, Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, wherein said heteroaryl and aryl groups are linked together via a single bond, and wherein Ha1 is bonded via said aryl moiety to the to the parent molecular group, Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, wherein said heteroaryl and aryl groups are linked together via a single bond, and wherein Ha2 is bonded via said aryl moiety to the parent molecular group, Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, wherein said heteroaryl and aryl groups are linked together via a single bond, and wherein Ha3 is bonded via said aryl moiety to the to the parent molecular group, Ha4 is a heteroarylaryl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and an aryl group selected from a group consisting of phenyl and naphthyl, wherein said heteroaryl and aryl groups are linked together via a single bond, and wherein Ha4 is bonded via said aryl moiety to the to the parent molecular group, R7 is hydroxyl, or Cyc1, in which Cyc1 is a ring system of formula Ia

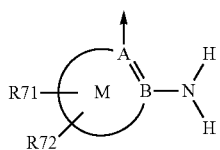

in which

A and B are C (carbon),

R71 and R72 are independently hydrogen, halogen, 1-4C-alkyl, or 1-4C-alkoxy,

M with inclusion of A and B is either a ring Ar2 or a ring Har2, in which Ar2 is a benzene ring, Har2 is a monocyclic 5- or 6-membered unsaturated heteroaromatic ring comprising one to three heteroatoms, each of which is selected from the group consisting of nitrogen, oxygen and sulfur.

2. A method according to claim 1, wherein the HDAC inhibitor is (E)-N-(2-aminophenyl)-3-(1-((4-(1-methyl-1H-pyrazol-4-yl)phenyl)sulfonyl)-1H-pyrrol-3-yl)acrylamide (also known as 4SC-202), or a salt or solvate thereof.

3. A method according to claim 1, wherein the HDAC inhibitor is 4SC-202 tosylate salt.

4. A method according to claim 1, wherein the CD137 agonist is selected from the group consisting of INBRX-105, ADG-106, FS-120, CB-307, STIM-41BBL, FS-222, PRS-344, GEN-1046, AGEN-2373, CD19-4-1BBL, AM-105, CTX-471, TM-123+UniCAR-T, RTX-240, CUE-201, RTX-224, Utomilumab, Urelumab, ABP-300, EU-101, ATOR-1016, PRS-343, PRS-342, ET-140 or lisocabtagene maraleucel, LOAd-703, KAHR-105 KAHR-107, SCB-333, MP-0310, ISAS-01 and Ultra-41BBL.

5. A method according to claim 1, wherein said cancer is selected from the group consisting of melanoma, head and neck cancer, renal cancer, Non-small cell lung cancer (NSCLC), microsatellite-instable carcinoma, lynch syndrome, urothelial carcinoma, merkel cell carcinoma, hodgkin lymphoma, gastric cancer, microsatellite stable gastrointestinal cancer, microsatellite instable gastrointestinal cancer, hepatocellular carcinoma (HCC), nasopharyngeal carcinoma, basal cell carcinoma, cervical cancer, anogenital cancers, Kaposi sarcoma, adult T-cell leukemia, primary effusion lymphoma; and Castlemann's disease.

6. A method according to claim 1, wherein said cancer is selected from the group consisting of breast cancer, oesophageal cancer, non-hodgkin lymphoma, small cell lung cancer (SCLC), sarcoma, mesothelioma, glioblastoma, microsatellite stable cancer, pancreas cancer, prostate cancer, cutaneous T-cell lymphoma (CTCL) and squamous cell carcinoma.

7. A method according to claim 1, wherein said cancer is ocular, uveal or skin melanoma or is gastroesophageal or colorectal lynch syndrome or is bladder cancer, colorectal cancer (CRC) or renal cell carcinoma (RCC).

8. A method according to claim 1, wherein said cancer is triple-negative breast cancer or gastroesophageal or colorectal microsatellite stable cancer.

9. A method according to claim 1, wherein an HDAC inhibitor of formula I or a salt thereof is administered.

10. A method according to claim 1, wherein the HDAC inhibitor is (E)-N-(2-aminophenyl)-3-(1-((4-(1-methyl-1H-pyrazol-4-yl)phenyl)sulfonyl)-1H-pyrrol-3-yl)acrylamide (also known as 4SC-202) or a salt thereof.

11. A method according to claim 4, wherein the HDAC inhibitor is 4SC-202 tosylate salt.

12. A method according to claim 5, wherein the HDAC inhibitor is 4SC-202 tosylate salt.

13. A method according to claim 6, wherein the HDAC inhibitor is 4SC-202 tosylate salt.

14. A method according to claim 7, wherein the HDAC inhibitor is 4SC-202 tosylate salt.

15. A method according to claim 8, wherein the HDAC inhibitor is 4SC-202 tosylate salt.

* * * * *